(12) United States Patent
Jaworski et al.

(10) Patent No.: US 7,350,720 B2
(45) Date of Patent: Apr. 1, 2008

(54) ACTIVE MATERIAL EMITTING DEVICE

(75) Inventors: Thomas Jaworski, Racine, WI (US);
Steven B. Mineau, Racine, WI (US);
David J. Schram, Waterford, WI (US);
Scott W. Demarest, Caledonia, WI (US); Dean Holzberger, Belgium, WI (US); Jeffrey J. Wolf, Racine, WI (US); Mark Niederberger, Einsiedeln (CH); Thomas Froehlich, Zurich (CH)

(73) Assignee: S.C. Johnson & Son, Inc., Racine, WI (US)

( * ) Notice: Subject to any disclaimer, the term of this patent is extended or adjusted under 35 U.S.C. 154(b) by 173 days.

(21) Appl. No.: 11/140,329

(22) Filed: May 27, 2005

(65) Prior Publication Data

US 2005/0285538 A1   Dec. 29, 2005

Related U.S. Application Data

(63) Continuation-in-part of application No. 11/050,242, filed on Feb. 3, 2005, and a continuation-in-part of application No. 11/050,169, filed on Feb. 3, 2005.

(60) Provisional application No. 60/541,067, filed on Feb. 3, 2004.

(51) Int. Cl.
*F21L 19/00* (2006.01)

(52) U.S. Cl. .......................... 239/55; 239/34; 422/123; 362/161; 362/253; 362/810

(58) Field of Classification Search ................ 362/161, 362/157, 643, 810; 431/289; 422/123–126, 422/120, 305, 306; 239/34, 55
See application file for complete search history.

(56) References Cited

U.S. PATENT DOCUMENTS

| 240,764 | A | 4/1881 | Reynolds |
| D27,883 | S | 11/1897 | Noke |
| 606,850 | A | 7/1898 | Wallace et al. |
| 738,999 | A | 9/1903 | Higgins |
| 937,836 | A | 10/1909 | Matthai |
| D42,648 | S | 6/1912 | Sanford |
| D55,864 | S | 7/1920 | Jenkins |
| 1,648,748 | A | 11/1927 | Traub |
| 1,665,412 | A | 4/1928 | Hall |
| D75,124 | S | 5/1928 | Jenkins |

(Continued)

FOREIGN PATENT DOCUMENTS

AU          4932300          11/2000

(Continued)

OTHER PUBLICATIONS

Candle Impressions® Website (Formerly Candles of Paradise) at http://www.candleimpressions.net/cgi-ole/cs.waframe.homepage dated Nov. 14, 2005 (1 page).

(Continued)

*Primary Examiner*—Ali Alavi
*Assistant Examiner*—Evan Dzierzynski

(57) ABSTRACT

An active material cartridge comprises a frame and an active material refill. The active material refill comprises at least one reservoir having an active material therein and a protrusion extending from a first end thereof. The active material refill is disposed on and attached to the frame.

15 Claims, 50 Drawing Sheets

U.S. PATENT DOCUMENTS

| | | |
|---|---|---|
| 1,806,046 A | 5/1931 | Deeter |
| 1,947,806 A | 2/1934 | Smith |
| 1,975,496 A | 10/1934 | Barrett, Jr. |
| 2,014,217 A | 9/1935 | Williamson |
| D103,209 S | 2/1937 | Beiser |
| 2,080,259 A | 5/1937 | Frei, Jr. |
| RE20,434 E | 7/1937 | Barrett, Jr. |
| 2,102,224 A | 12/1937 | Ruppel |
| 2,111,642 A | 3/1938 | Saier |
| 2,124,009 A | 7/1938 | Schneider |
| D128,935 S | 8/1941 | Derham et al. |
| 2,254,134 A | 8/1941 | Berry |
| 2,360,603 A | 10/1944 | Ward |
| 2,437,809 A | 3/1948 | Engelbrecht |
| 2,459,898 A | 1/1949 | Stiffel |
| 2,494,995 A | 1/1950 | Gardner |
| 2,523,818 A | 9/1950 | Cortes |
| 2,525,464 A | 10/1950 | Springer |
| 2,567,780 A | 9/1951 | Oppelt |
| 2,608,645 A | 8/1952 | Hines |
| 2,611,068 A | 9/1952 | Wellens |
| 2,632,098 A | 3/1953 | Marchese |
| 2,691,548 A | 10/1954 | Feucht et al. |
| 2,721,244 A | 10/1955 | Seekins |
| D180,916 S | 9/1957 | Perlman |
| 2,807,691 A | 9/1957 | Sorenson |
| 2,863,547 A | 12/1958 | Cavalleri |
| 2,935,608 A | 5/1960 | Mirzwinski |
| 2,954,771 A | 10/1960 | Boyan |
| 2,984,724 A | 5/1961 | Merz |
| D191,396 S | 9/1961 | Weber, III |
| 3,045,878 A | 7/1962 | Blanford et al. |
| 3,145,323 A | 8/1964 | Klotz |
| 3,149,761 A | 9/1964 | Harris et al. |
| 3,153,123 A | 10/1964 | Harman |
| 3,174,659 A | 3/1965 | Sorber et al. |
| 3,209,949 A | 10/1965 | Gurtler |
| 3,233,093 A | 2/1966 | Gerlat |
| D205,556 S | 8/1966 | Plochman, Jr. |
| 3,428,224 A | 2/1969 | Eberhardt et al. |
| 3,429,484 A | 2/1969 | Baldwin |
| 3,435,286 A | 3/1969 | Kayatt |
| D214,831 S | 8/1969 | Lomont et al. |
| 3,473,014 A | 10/1969 | Kayne |
| 3,500,126 A | 3/1970 | Ford |
| 3,506,876 A | 4/1970 | Antonich |
| D217,719 S | 6/1970 | McNair et al. |
| D218,145 S | 7/1970 | Doblin |
| 3,531,637 A | 9/1970 | Nathanson |
| 3,580,432 A | 5/1971 | Brooks |
| D221,891 S | 9/1971 | Douglas |
| 3,604,920 A | 9/1971 | Niles |
| 3,648,905 A | 3/1972 | Kauder |
| 3,710,182 A | 1/1973 | Van Reenen |
| 3,789,211 A | 1/1974 | Kramer |
| 3,860,847 A | 1/1975 | Carley |
| 3,890,085 A | 6/1975 | Andeweg |
| 3,893,041 A | 7/1975 | Foster et al. |
| 3,926,655 A | 12/1975 | Miles |
| 3,934,105 A | 1/1976 | Lockard |
| 3,943,352 A | 3/1976 | Pena May |
| 3,944,806 A | 3/1976 | Jones et al. |
| 3,946,173 A | 3/1976 | Haber |
| 3,948,445 A | 4/1976 | Andeweg |
| 3,987,942 A | 10/1976 | Morane et al. |
| 3,990,848 A | 11/1976 | Corris |
| D243,017 S | 1/1977 | Fossella |
| 4,017,729 A | 4/1977 | Frazier, Jr. |
| 4,035,451 A | 7/1977 | Tringali |
| 4,038,561 A | 7/1977 | Lorenz |
| 4,052,622 A | 10/1977 | Lorenz |
| 4,064,414 A | 12/1977 | Bergeson et al. |
| 4,071,805 A | 1/1978 | Brock |
| 4,077,549 A | 3/1978 | Beard |
| 4,111,655 A | 9/1978 | Quincey |
| 4,132,359 A | 1/1979 | Nozawa |
| 4,159,442 A | 6/1979 | Komatsu |
| 4,177,407 A | 12/1979 | Goldstein et al. |
| 4,187,532 A | 2/1980 | Naffier |
| 4,228,885 A | 10/1980 | Cavalleri |
| 4,253,045 A | 2/1981 | Weber |
| 4,264,037 A | 4/1981 | Nozawa |
| 4,276,236 A | 6/1981 | Sullivan et al. |
| 4,283,661 A | 8/1981 | Doty |
| 4,307,460 A | 12/1981 | Polonsky |
| 4,325,110 A | 4/1982 | Tang |
| 4,328,534 A | 5/1982 | Abe |
| 4,346,059 A | 8/1982 | Spector |
| 4,413,779 A | 11/1983 | Santini |
| 4,417,182 A | 11/1983 | Weber |
| 4,477,249 A | 10/1984 | Ruzek et al. |
| 4,492,896 A | 1/1985 | Jullien |
| 4,500,795 A | 2/1985 | Hochstein et al. |
| 4,502,630 A | 3/1985 | Haworth et al. |
| 4,508,520 A | 4/1985 | Sellers et al. |
| 4,510,556 A | 4/1985 | Johnson |
| 4,540,984 A | 9/1985 | Waldman |
| 4,550,363 A | 10/1985 | Sandell |
| 4,558,820 A | 12/1985 | Harris, Jr. |
| D282,152 S | 1/1986 | Mendenhall |
| 4,568,269 A | 2/1986 | Lin |
| 4,583,686 A | 4/1986 | Martens et al. |
| 4,588,874 A | 5/1986 | Napierski |
| 4,593,232 A | 6/1986 | McEdwards |
| 4,617,614 A | 10/1986 | Lederer |
| 4,621,768 A | 11/1986 | Lhoste et al. |
| 4,629,604 A | 12/1986 | Spector |
| D287,885 S | 1/1987 | Bolduc |
| D288,856 S | 3/1987 | Owen et al. |
| 4,660,763 A | 4/1987 | Gutkowski et al. |
| 4,660,764 A | 4/1987 | Joyaux et al. |
| 4,666,638 A | 5/1987 | Baker et al. |
| 4,675,578 A | 6/1987 | Mitchell et al. |
| D291,242 S | 8/1987 | Harden et al. |
| 4,693,681 A | 9/1987 | Comstock |
| 4,695,434 A | 9/1987 | Spector |
| 4,695,435 A | 9/1987 | Spector |
| 4,707,338 A | 11/1987 | Spector |
| 4,714,984 A | 12/1987 | Spector |
| 4,739,928 A | 4/1988 | O'Neil |
| 4,743,406 A | 5/1988 | Steiner et al. |
| 4,768,393 A | 9/1988 | Beaman |
| 4,771,769 A | 9/1988 | Hegemann et al. |
| 4,773,571 A | 9/1988 | Hagan et al. |
| 4,777,345 A | 10/1988 | Manchester |
| 4,779,734 A | 10/1988 | Kydonieus |
| 4,781,895 A | 11/1988 | Spector |
| 4,804,323 A | 2/1989 | Kim |
| 4,804,821 A | 2/1989 | Glucksman |
| 4,805,839 A | 2/1989 | Malek |
| D300,107 S | 3/1989 | Trombly |
| D301,205 S | 5/1989 | Joyaux et al. |
| 4,826,054 A | 5/1989 | Frutin |
| 4,830,791 A | 5/1989 | Muderlak et al. |
| 4,837,421 A | 6/1989 | Luthy |
| 4,839,780 A | 6/1989 | Chuan et al. |
| 4,840,770 A | 6/1989 | Walz et al. |
| 4,849,606 A | 7/1989 | Martens, III et al. |
| 4,855,580 A | 8/1989 | Van Maanen, Jr. |
| 4,857,240 A | 8/1989 | Kearnes et al. |
| 4,865,816 A | 9/1989 | Walz et al. |
| 4,866,580 A | 9/1989 | Blackerby |
| 4,870,325 A | 9/1989 | Kazar |
| 4,895,512 A | 1/1990 | Sullivan et al. |

| | | | | | |
|---|---|---|---|---|---|
| 4,901,891 A | 2/1990 | Gonclaves | 5,647,053 A | 7/1997 | Schroeder et al. |
| 4,913,350 A | 4/1990 | Purzycki | 5,651,942 A | 7/1997 | Christensen |
| 4,926,298 A | 5/1990 | Zimmerman | 5,662,835 A | 9/1997 | Collingwood |
| 4,931,224 A | 6/1990 | Holzner, Sr. | D386,974 S | 12/1997 | Wefler |
| 4,960,240 A | 10/1990 | McElfresh | D387,447 S | 12/1997 | Hollington |
| 4,963,939 A | 10/1990 | Kurando et al. | 5,697,695 A | 12/1997 | Lin et al. |
| 4,968,487 A | 11/1990 | Yamamoto et al. | D388,892 S | 1/1998 | Ratia |
| D314,237 S | 1/1991 | Blumanthal, Jr. | D390,941 S | 2/1998 | Cessaroni et al. |
| 4,983,119 A | 1/1991 | Lin | D392,032 S | 3/1998 | Zaragoza et al. |
| 4,992,912 A | 2/1991 | Lee | 5,725,152 A | 3/1998 | Akyu |
| D317,059 S | 5/1991 | Menter | 5,782,553 A | 7/1998 | McDermott |
| 5,013,972 A | 5/1991 | Malkieli et al. | 5,788,061 A | 8/1998 | Hammond |
| 5,015,175 A | 5/1991 | Lee | 5,788,155 A | 8/1998 | Martin et al. |
| 5,018,647 A | 5/1991 | Abplanalf | 5,788,931 A | 8/1998 | Munoz Quintana |
| 5,032,766 A | 7/1991 | Gundlach et al. | 5,791,774 A | 8/1998 | Briles |
| 5,034,658 A | 7/1991 | Hiering et al. | 5,805,768 A | 9/1998 | Schwarz et al. |
| 5,035,728 A | 7/1991 | Fang | 5,847,512 A | 12/1998 | Baba et al. |
| 5,038,972 A | 8/1991 | Muderlak et al. | 5,853,672 A | 12/1998 | Lorman et al. |
| 5,040,705 A | 8/1991 | Snell | 5,863,108 A | 1/1999 | Lederer |
| 5,050,798 A | 9/1991 | Sullivan | D406,365 S | 3/1999 | Furner |
| 5,057,003 A | 10/1991 | Yang | 5,884,808 A | 3/1999 | Muderlak et al. |
| D321,476 S | 11/1991 | Alcover | 5,890,633 A * | 4/1999 | Skillin et al. ............... 222/523 |
| 5,069,876 A | 12/1991 | Oshinsky | 5,891,400 A | 4/1999 | Ansari et al. |
| 5,091,678 A | 2/1992 | Chin-Song | 5,894,201 A | 4/1999 | Wong |
| RE33,864 E | 3/1992 | Steiner et al. | 5,909,845 A | 6/1999 | Greatbatch et al. |
| 5,097,180 A | 3/1992 | Ignon et al. | 5,909,954 A | 6/1999 | Thomas |
| D326,168 S | 5/1992 | Smith | 5,924,784 A | 7/1999 | Chliwnyj et al. |
| 5,111,477 A | 5/1992 | Muderlak | 5,950,922 A | 9/1999 | Flinn |
| 5,114,625 A | 5/1992 | Gibson | 5,961,043 A | 10/1999 | Samuelson et al. |
| 5,115,975 A | 5/1992 | Shilling | 5,964,519 A | 10/1999 | Chun-Ying |
| 5,126,078 A | 6/1992 | Steiner et al. | 5,969,479 A | 10/1999 | Wong |
| 5,133,042 A | 7/1992 | Pelonis | 5,970,643 A | 10/1999 | Gawel, Jr. |
| 5,138,538 A | 8/1992 | Sperling | 5,972,290 A | 10/1999 | De Sousa |
| 5,147,582 A | 9/1992 | Holzner, Sr. et al. | D416,098 S | 11/1999 | Sher |
| 5,148,984 A | 9/1992 | Bryson, Jr. et al. | 5,975,427 A | 11/1999 | Harries |
| 5,152,602 A | 10/1992 | Boschetto | 5,980,064 A | 11/1999 | Metroyanis |
| 5,164,636 A | 11/1992 | Allaire | 5,992,707 A | 11/1999 | Gaichuk |
| 5,174,645 A | 12/1992 | Chung | 6,017,139 A | 1/2000 | Lederer |
| 5,175,791 A | 12/1992 | Muderlak et al. | D420,754 S | 2/2000 | Huang |
| 5,178,450 A | 1/1993 | Zelensky et al. | D422,101 S | 3/2000 | Barraclogh et al. |
| 5,187,655 A | 2/1993 | Post et al. | 6,050,551 A | 4/2000 | Anderson |
| D333,778 S | 3/1993 | Magidson et al. | 6,066,924 A | 5/2000 | Lederer |
| 5,212,672 A | 5/1993 | Loisch et al. | D426,667 S | 6/2000 | Kaviani |
| 5,217,696 A | 6/1993 | Wolverton et al. | 6,104,866 A | 8/2000 | DeWitt et al. |
| 5,223,182 A * | 6/1993 | Steiner et al. ............... 261/26 | 6,104,867 A | 8/2000 | Stathakis et al. |
| 5,228,771 A | 7/1993 | Zimmerman | 6,106,786 A | 8/2000 | Akahoshi |
| 5,234,162 A | 8/1993 | Sullivan | 6,135,612 A | 10/2000 | Clore |
| 5,249,713 A | 10/1993 | Reich et al. | 6,152,568 A | 11/2000 | Baba et al. |
| 5,316,185 A | 5/1994 | Meenan | 6,153,981 A | 11/2000 | Thomas et al. |
| D349,642 S | 8/1994 | Abfier | D436,038 S | 1/2001 | Ruiz de Gopegui |
| 5,342,584 A | 8/1994 | Fritz et al. | D437,040 S | 1/2001 | Soller et al. |
| 5,364,027 A | 11/1994 | Kuhn | D437,064 S | 1/2001 | Boss |
| D353,194 S | 12/1994 | Walton et al. | 6,196,706 B1 | 3/2001 | Cutts |
| 5,370,313 A | 12/1994 | Beard | RE37,168 E | 5/2001 | St. Louis |
| 5,370,829 A | 12/1994 | Kunze | 6,241,362 B1 | 6/2001 | Morrison |
| 5,376,338 A | 12/1994 | Zlotnik | D448,097 S | 9/2001 | Bodum |
| RE34,847 E | 2/1995 | Muderlak et al. | D448,535 S | 9/2001 | Delmerico |
| 5,388,714 A | 2/1995 | Zutler | 6,288,498 B1 | 9/2001 | Cheng |
| 5,392,379 A | 2/1995 | Fussell | 6,293,474 B1 | 9/2001 | Helf et al. |
| D356,523 S | 3/1995 | Rahr | D449,877 S | 10/2001 | Delmenico et al. |
| D357,085 S | 4/1995 | Ratia | 6,296,196 B1 | 10/2001 | Denen et al. |
| D357,531 S | 4/1995 | Weick | 6,302,559 B1 | 10/2001 | Warren |
| D359,346 S | 6/1995 | Martin | 6,305,820 B1 | 10/2001 | Poon |
| 5,460,787 A | 10/1995 | Colon | D450,862 S | 11/2001 | Alcedo |
| 5,498,397 A | 3/1996 | Horng | D451,183 S | 11/2001 | Hirano et al. |
| 5,547,616 A | 8/1996 | Dancs et al. | 6,325,256 B1 | 12/2001 | Liljeqvist et al. |
| 5,564,665 A | 10/1996 | Resnick | 6,341,732 B1 | 1/2002 | Martin et al. |
| 5,600,209 A | 2/1997 | St. Louis | 6,351,079 B1 | 2/2002 | Willis |
| 5,611,486 A | 3/1997 | Paul | D454,190 S | 3/2002 | Trocola |
| D378,802 S | 4/1997 | Corcoran | 6,354,710 B1 | 3/2002 | Nacouzi |
| D380,257 S | 6/1997 | Ganor | 6,357,726 B1 | 3/2002 | Watkins |
| D380,821 S | 7/1997 | Chen | 6,361,192 B1 | 3/2002 | Fussell et al. |
| D381,561 S | 7/1997 | Manca | 6,361,752 B1 | 3/2002 | Demarest et al. |

| | | | | | | |
|---|---|---|---|---|---|---|
| 6,371,450 B1 | 4/2002 | Davis et al. | | D497,808 S | 11/2004 | Morris et al. |
| 6,382,522 B2 | 5/2002 | Tomkins et al. | | 6,820,777 B2 | 11/2004 | Frutin |
| 6,394,630 B1 | 5/2002 | Skidmore et al. | | 6,834,847 B2 | 12/2004 | Bartsch et al. |
| D460,894 S | 7/2002 | Ziegenfus et al. | | 6,843,430 B2 | 1/2005 | Boticki et al. |
| 6,446,583 B2 | 9/2002 | Vieira | | 6,854,208 B1 | 2/2005 | Chuang et al. |
| 6,450,419 B1 | 9/2002 | Martens, III et al. | | 6,880,958 B2 | 4/2005 | Swarovski |
| 6,454,425 B1 | 9/2002 | Lin | | 6,906,472 B2 | 6/2005 | Wong |
| 6,474,510 B2 | 11/2002 | Frutin | | 6,926,423 B2 | 8/2005 | Bucher et al. |
| 6,481,639 B1 | 11/2002 | Pozzo | | 6,932,496 B2 | 8/2005 | Rizkin et al. |
| 6,486,726 B1 | 11/2002 | Worley, Sr. et al. | | D509,893 S | 9/2005 | Sevy |
| 6,487,367 B2 | 11/2002 | Vieira | | 6,957,779 B2 | 10/2005 | Joshi et al. |
| 6,494,349 B1 | 12/2002 | Thompson et al. | | 6,963,180 B2 | 11/2005 | Rose |
| 6,501,906 B2 | 12/2002 | Vieira | | 7,011,426 B2 | 3/2006 | Gabor |
| D470,077 S | 2/2003 | Osawa | | 2001/0032655 A1 | 10/2001 | Gindi |
| D470,433 S | 2/2003 | Osawa | | 2002/0030067 A1 | 3/2002 | Frutin |
| 6,525,487 B2 | 2/2003 | Wei | | 2002/0066798 A1 | 6/2002 | Laudamiel-Pellet et al. |
| 6,533,828 B1 | 3/2003 | Calzada | | 2002/0068009 A1 | 6/2002 | Laudamiel-Pellet et al. |
| 6,536,746 B2 | 3/2003 | Watkins | | 2002/0068010 A1 | 6/2002 | Laudamiel-Pallet et al. |
| 6,555,068 B2 | 4/2003 | Smith | | 2002/0080601 A1 | 6/2002 | Meltzer |
| 6,556,147 B1 | 4/2003 | Fisher et al. | | 2002/0093834 A1 | 7/2002 | Yu et al. |
| D474,854 S | 5/2003 | Lam | | 2002/0136886 A1 | 9/2002 | He et al. |
| 6,563,091 B2 | 5/2003 | Vieira | | 2002/0158351 A1 | 10/2002 | Wohrle |
| 6,569,387 B1 | 5/2003 | Furner et al. | | 2002/0172512 A1 | 11/2002 | Stathakis et al. |
| D476,070 S | 6/2003 | Millan | | 2003/0007887 A1 | 1/2003 | Roumpos et al. |
| 6,572,365 B1 | 6/2003 | Byxbe | | 2003/0052137 A1 | 3/2003 | Frutin |
| 6,575,613 B2 | 6/2003 | Brown et al. | | 2003/0053305 A1 | 3/2003 | Lin |
| 6,581,915 B2 | 6/2003 | Bartsch et al. | | 2003/0075571 A1 | 4/2003 | Thompson et al. |
| D477,095 S | 7/2003 | Avital | | 2003/0081420 A1 | 5/2003 | Jensen et al. |
| D477,424 S | 7/2003 | Avital | | 2003/0094503 A1 * | 5/2003 | Rymer et al. .................. 239/34 |
| 6,584,986 B2 | 7/2003 | Gindi | | 2003/0094504 A1 | 5/2003 | Rymer et al. |
| 6,592,104 B2 | 7/2003 | Cox | | 2003/0137258 A1 | 7/2003 | Piepgras et al. |
| 6,595,676 B2 | 7/2003 | Starry | | 2003/0162142 A1 | 8/2003 | Bennetts et al. |
| 6,602,466 B2 * | 8/2003 | Hamilton et al. .............. 422/37 | | 2003/0168751 A1 | 9/2003 | Bartsch et al. |
| 6,610,121 B2 | 8/2003 | Chasen | | 2003/0175148 A1 | 9/2003 | Kvietok et al. |
| 6,610,254 B1 | 8/2003 | Furner et al. | | 2003/0179581 A1 | 9/2003 | Swarovski |
| 6,616,308 B2 | 9/2003 | Jensen et al. | | 2003/0189022 A1 | 10/2003 | Fellows et al. |
| 6,631,852 B1 | 10/2003 | O'Leary | | 2003/0189825 A1 | 10/2003 | Tauch et al. |
| 6,631,888 B1 | 10/2003 | Prueter | | 2003/0198045 A1 | 10/2003 | Kitchen |
| 6,637,627 B1 | 10/2003 | Liljeqvist et al. | | 2003/0210555 A1 | 11/2003 | Cicero et al. |
| D482,465 S | 11/2003 | Slomowitz | | 2003/0214259 A9 | 11/2003 | Dowling et al. |
| 6,646,491 B2 | 11/2003 | Worley, Sr. et al. | | 2003/0227265 A1 | 12/2003 | Biebl |
| 6,655,604 B2 | 12/2003 | Tuttobene, Jr. | | 2004/0007787 A1 | 1/2004 | Kvietok et al. |
| 6,659,301 B2 | 12/2003 | Fellows et al. | | 2004/0009103 A1 | 1/2004 | Westring |
| 6,661,967 B2 | 12/2003 | Levine et al. | | 2004/0016818 A1 | 1/2004 | Murdell et al. |
| D485,624 S | 1/2004 | Kitamura | | 2004/0028551 A1 | 2/2004 | Kvietok et al. |
| 6,672,742 B2 | 1/2004 | Alley | | 2004/0032733 A1 | 2/2004 | Gabriel et al. |
| 6,685,064 B2 | 2/2004 | Frutin | | 2004/0033171 A1 | 2/2004 | Kvietok et al. |
| 6,685,335 B1 | 2/2004 | Yeh et al. | | 2004/0037069 A1 | 2/2004 | Blackbourn |
| 6,685,345 B1 | 2/2004 | Velasquez | | 2004/0051474 A1 | 3/2004 | Wong |
| 6,688,752 B2 | 2/2004 | Moore | | 2004/0094636 A1 | 5/2004 | Channer |
| 6,705,494 B2 | 3/2004 | Thompson et al. | | 2004/0141315 A1 | 7/2004 | Sherburne |
| 6,705,541 B2 | 3/2004 | Schuehrer et al. | | 2004/0160196 A1 | 8/2004 | Wong |
| 6,706,988 B1 | 3/2004 | Helf et al. | | 2004/0179355 A1 | 9/2004 | Gabor |
| 6,712,493 B2 | 3/2004 | Tell et al. | | 2004/0196658 A1 | 10/2004 | Fung |
| D488,582 S | 4/2004 | Connelly et al. | | 2004/0212322 A1 | 10/2004 | Rose |
| 6,719,217 B1 | 4/2004 | Tawara et al. | | 2004/0222245 A1 | 11/2004 | Marroncles |
| 6,719,443 B2 | 4/2004 | Gutstein et al. | | 2004/0222246 A1 | 11/2004 | Bates et al. |
| 6,728,478 B2 | 4/2004 | Cox et al. | | 2004/0246711 A1 | 12/2004 | Brenchley et al. |
| D489,970 S | 5/2004 | Nelson et al. | | 2004/0252498 A1 | 12/2004 | Gutstein et al. |
| 6,729,748 B2 | 5/2004 | Reilly | | 2004/0257798 A1 * | 12/2004 | Hart et al. .................... 362/96 |
| 6,741,042 B1 | 5/2004 | Tang | | 2004/0262418 A1 | 12/2004 | Smith et al. |
| D490,699 S | 6/2004 | Nelson et al. | | 2004/0262421 A1 | 12/2004 | Hurry et al. |
| D492,443 S | 6/2004 | Smith et al. | | 2004/0264169 A1 | 12/2004 | Limburg et al. |
| 6,768,865 B2 | 7/2004 | Stathakis et al. | | 2005/0045664 A1 | 3/2005 | Taylor |
| 6,779,905 B1 | 8/2004 | Mazursky et al. | | 2005/0047127 A1 | 3/2005 | Tutman |
| 6,783,081 B2 * | 8/2004 | Pedrotti et al. .............. 239/136 | | 2005/0053368 A1 | 3/2005 | Pesu et al. |
| 6,783,117 B2 | 8/2004 | Wohrle | | 2005/0074358 A1 | 4/2005 | Hart et al. |
| D495,819 S | 9/2004 | Krieger et al. | | 2005/0110417 A1 | 5/2005 | Li et al. |
| 6,790,408 B2 | 9/2004 | Whitby et al. | | 2005/0111217 A1 | 5/2005 | Feng |
| 6,792,199 B2 | 9/2004 | Levine et al. | | 2005/0169666 A1 | 8/2005 | Porchia et al. |
| 6,793,149 B2 | 9/2004 | Schramm et al. | | 2005/0169812 A1 | 8/2005 | Helf et al. |
| 6,801,003 B2 | 10/2004 | Schanberger et al. | | 2005/0184045 A1 | 8/2005 | Shimizu et al. |
| 6,808,297 B2 | 10/2004 | Jensen et al. | | 2005/0185392 A1 | 8/2005 | Walter et al. |

| | | | |
|---|---|---|---|
| 2005/0196716 | A1 | 9/2005 | Haab et al. |
| 2005/0254248 | A1 | 11/2005 | Lederer |
| 2007/0053181 | A1 | 3/2007 | Urkumyan |
| 2007/0177393 | A1 | 8/2007 | Hirata |

FOREIGN PATENT DOCUMENTS

| | | |
|---|---|---|
| DE | 297 13 945 | 11/1997 |
| DE | 201 03 621 | 6/2001 |
| EP | 252 642 | 1/1988 |
| EP | 321 729 | 6/1989 |
| EP | 722 743 | 7/1996 |
| EP | 1281406 | 2/2003 |
| FR | 2628825 | 9/1989 |
| GB | 2 347 563 | 9/2000 |
| GB | 2 388 653 | 11/2003 |
| GB | 2 398 627 | 8/2004 |
| JP | 5 408 2864 | 7/1979 |
| JP | 01-243483 | 9/1989 |
| JP | 4 122 415 | 4/1992 |
| JP | 06052709 | 2/1994 |
| JP | 09106890 | 4/1997 |
| JP | 9-244575 | 9/1997 |
| JP | 9-007411 | 10/1997 |
| JP | 11086602 | 3/1999 |
| JP | 2000245617 | 9/2000 |
| JP | 2002270013 | 9/2002 |
| JP | 2003187615 | 7/2003 |
| WO | WO 98/00179 | 1/1998 |
| WO | WO 99/17717 | 4/1999 |
| WO | WO 00/64498 | 11/2000 |
| WO | WO 03/098971 | 11/2003 |
| WO | WO 2005/097348 | 10/2005 |
| WO | WO 2005/098982 | 10/2005 |

OTHER PUBLICATIONS

Webpage http://www.candleimpressions.net/cgi-cs/cs.waframe.menu?lang=1&topic=19189&click=... dated Nov. 14, 2005 (1 page).

Webpage http://www.candleimpressions.net/cgi-cs/cs.waframe.submenu?topic=19189&img_num=... dated Nov. 14, 2005 (1 page).

"Welcome to our Candles of Paradise Web Site," at http://www.candleimpressions.net/cgi-cs/cs.waframe.content?topic=19189img_num=&... dated Nov. 14, 2005 (1 page).

"Battery Operated Flickering Wax Candles," at http://www.candleimpressions.net/cgi-cs/cs.waframe.content?topic=19538&lang=1 dated Nov. 14, 2005 (3 pages).

"Battery Operated Flickering Wax Candles with Candle Holders," at http://www.candleimpressions.net/cgi-cs/cs.waframe.content?topic=26227&lang=1 dated Nov. 14, 2005 (3 pages).

"Battery Operated Wall Sconces with Flameless Wax Candles," at http://www.candleimpressions.net/cgi-cs/cs.waframe.content?topic=26221&lang=1 dated Nov. 14, 2005 (2 pages).

"Battery Operated Flickering Candle Light Fixtures," at http://www.candleimpressions.net/cgi-cs.waframe.content?19541&lang=1 dated Nov. 14, 2005 (5 pages).

"Solar Operated Flickering Candle Light Fixtures," at http://www.candleimpressions.net/cgi-cs/cs.waframe.content?topic=19542&lang=1 dated Nov. 14, 2005 (1 page).

"Candle Fire Safety," at http://www.candleimpressions.net/cgi-cs/cs.waframe.content?topic=19530&img_num=2 dated Nov. 14, 2005 (1 page).

Web Page http://www.nam.lighting.philips.com/us/led/ dated Oct. 21, 2005 (1 page).

Web Page http://www.nam.lighting.philips.com/us/led/features_specs.php?mode=1 dated Oct. 21, 2005 (2 pages).

Web Page http://www.nam.lighting.philips.com/us/led/features_specs.php?mode=2 dated Oct. 21, 2005 (2 pages).

Web Page http://www.amazon.com/exec/obidos/tg/detail/-/B0009WRJ58/103-3573233-1695062?v=glance&s=home-...dated Oct. 21, 2005 (3 pages).

Web Page http://www.amazon.com/exec/obidos/tg/detail/-/B0009WRJ58/103-3573233-1695062?v=glance&s=home-...dated Oct. 21, 2005 (3 pages).

Photographs of "Everlasting Tealights" packaging and device—Made in China, designed and imported by the Gerson Company—Olathe, KS, (5 pages).

International Search Report in PCT/US2006/042971 dated Mar. 22, 2007.

Written Opinion in PCT/US2006/042971 dated Mar. 22, 2007.

International Search Report and Written Opinion in PCT/US2006/042919 dated Apr. 20, 2007.

International Search Report and Written Opinion in PCT/US2006/020127 dated Sep. 11, 2007.

* cited by examiner

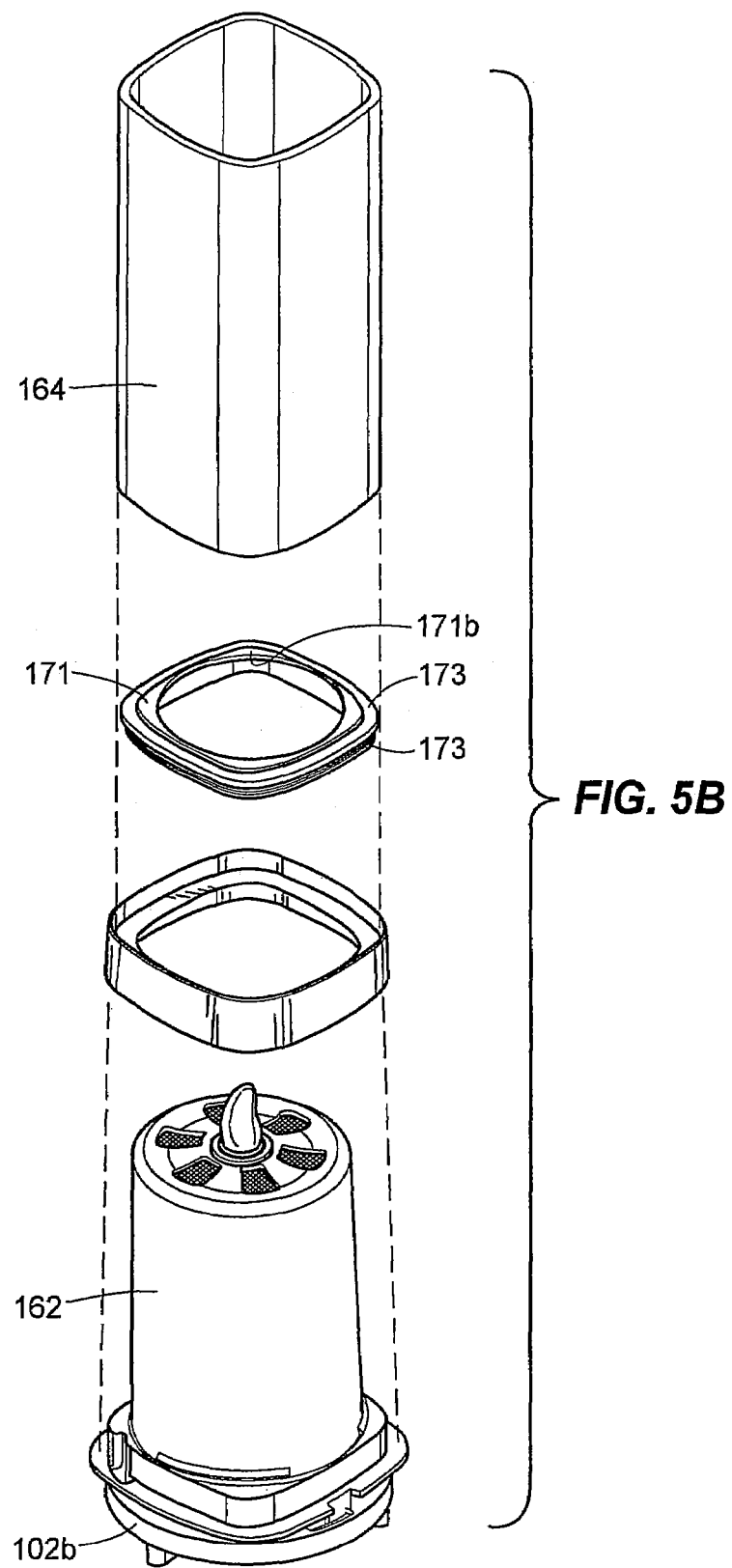

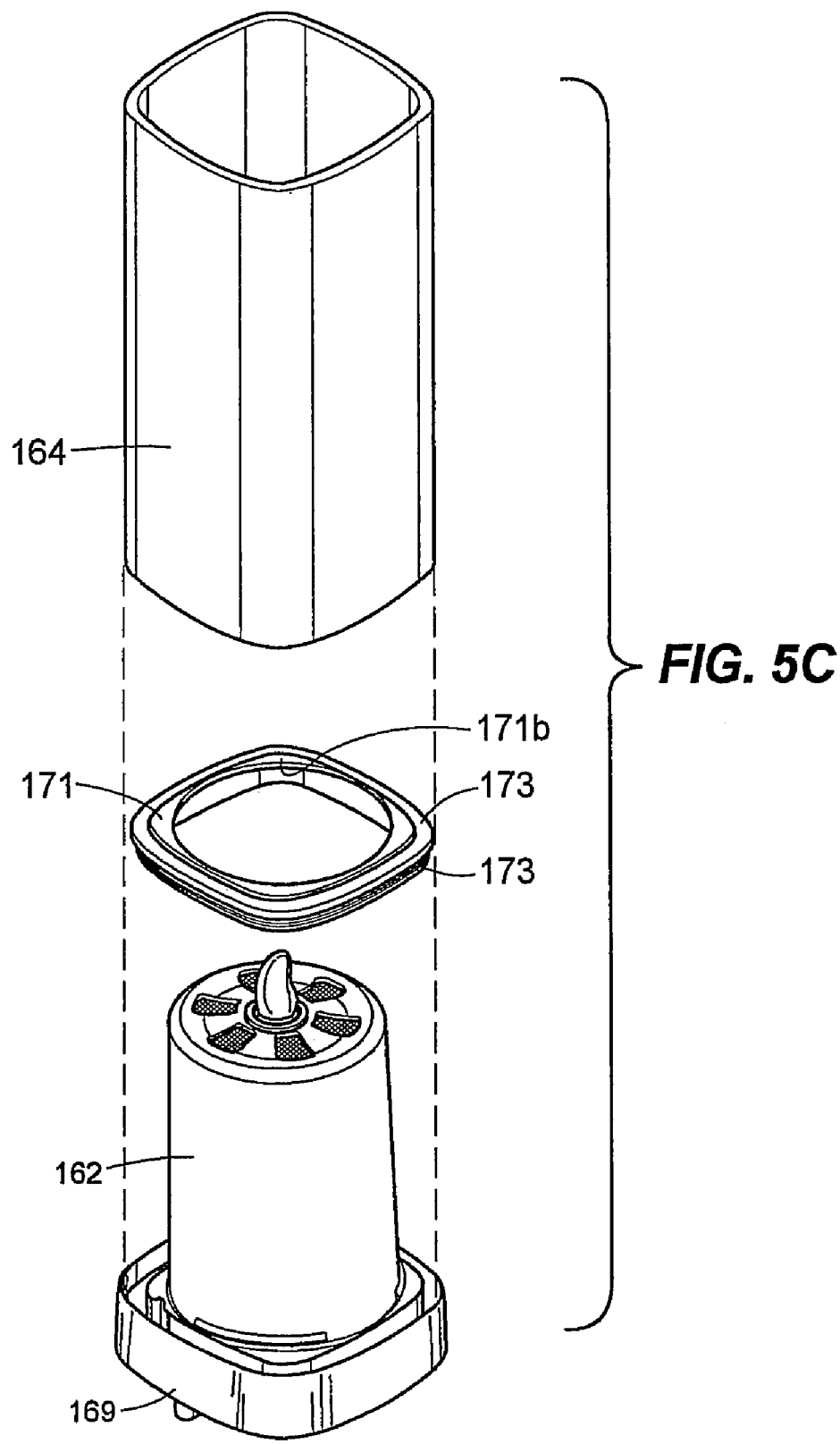

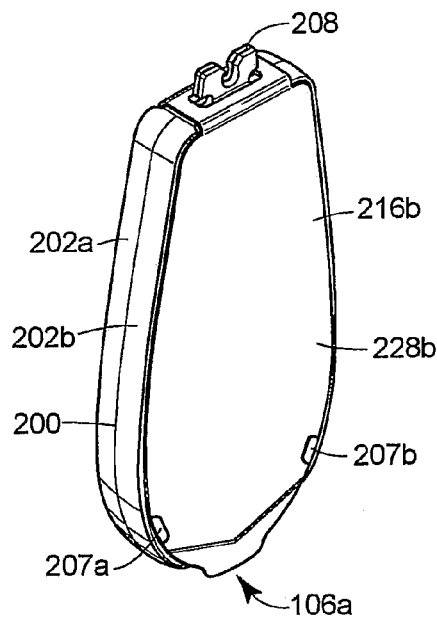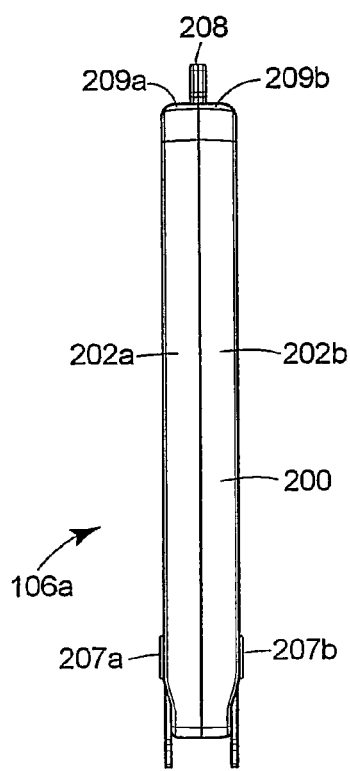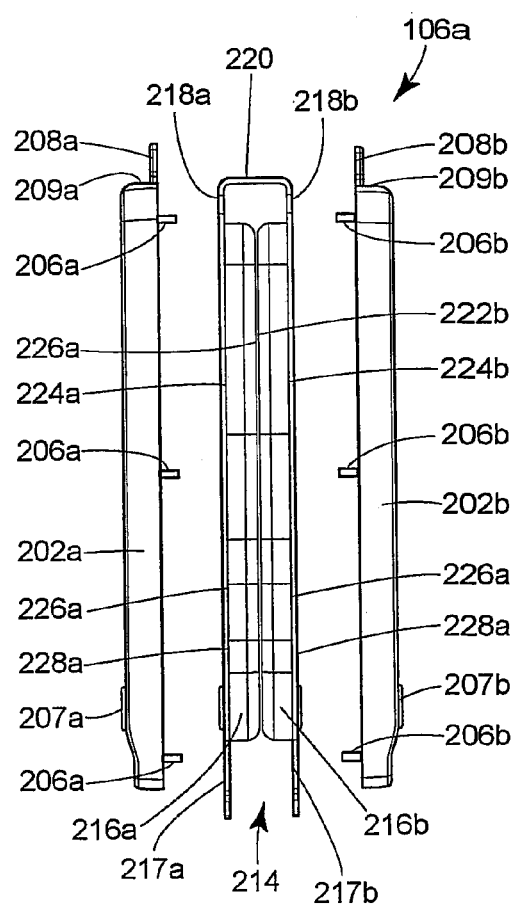

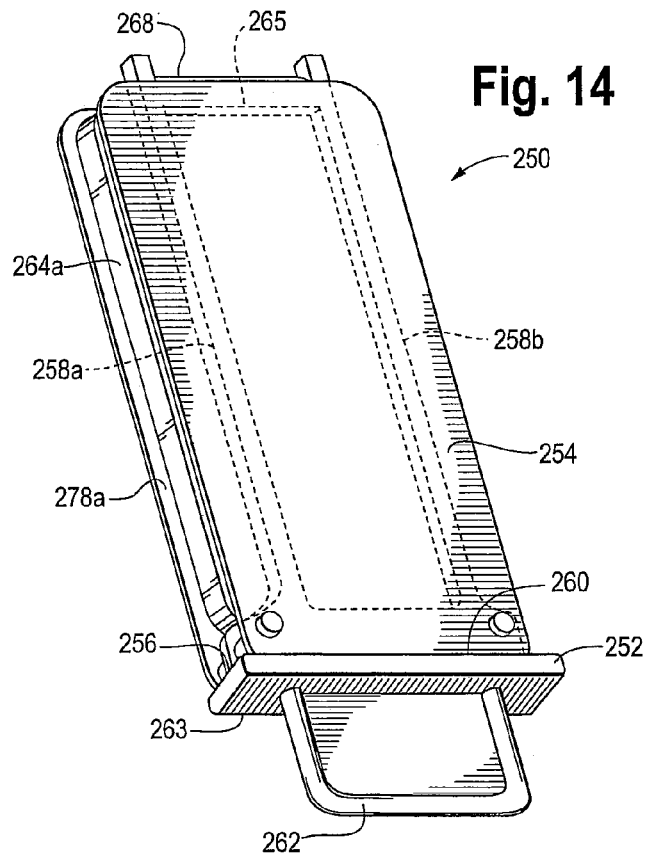
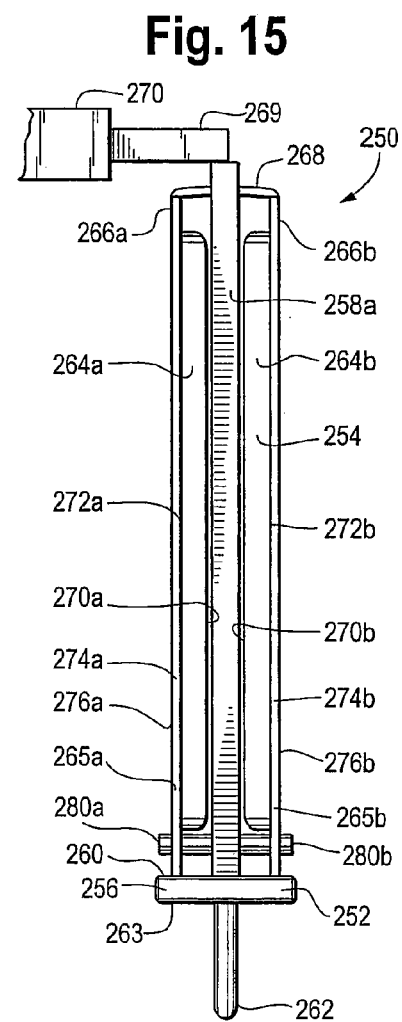

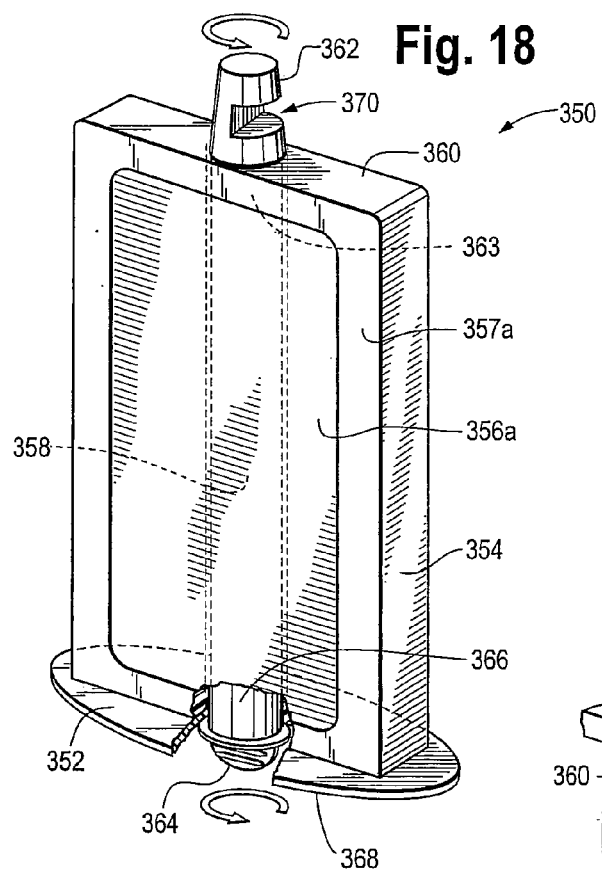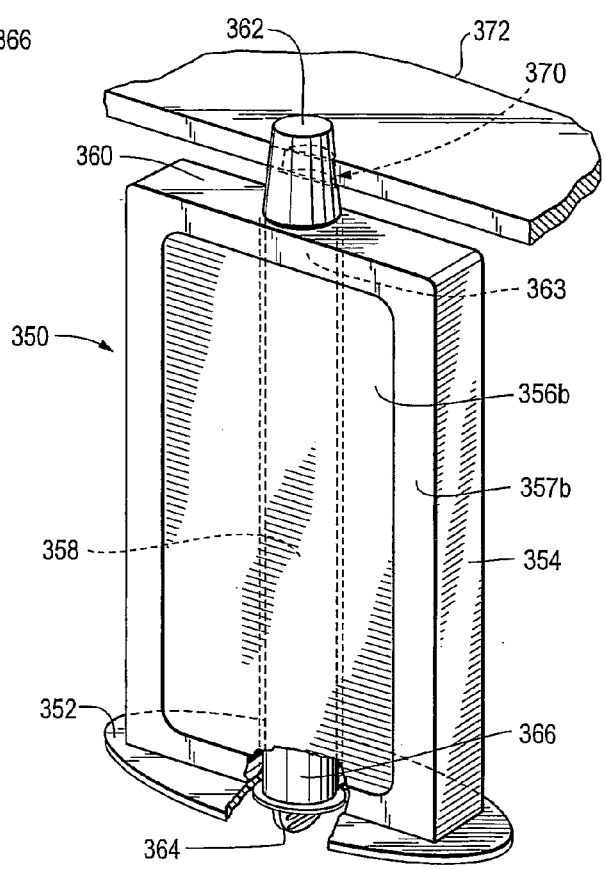

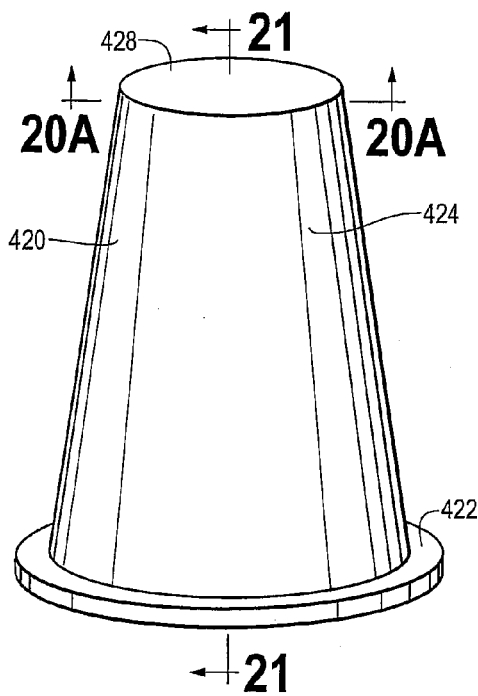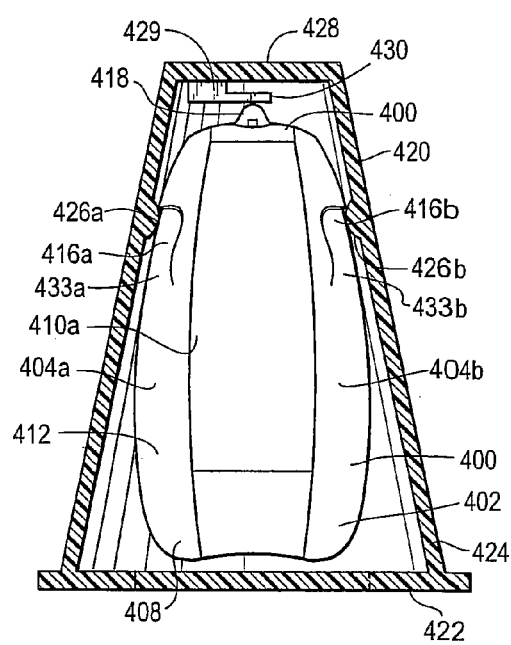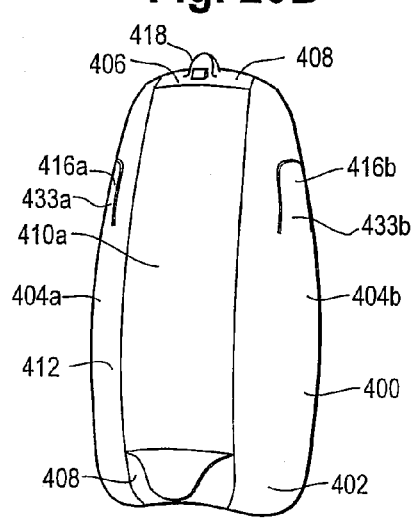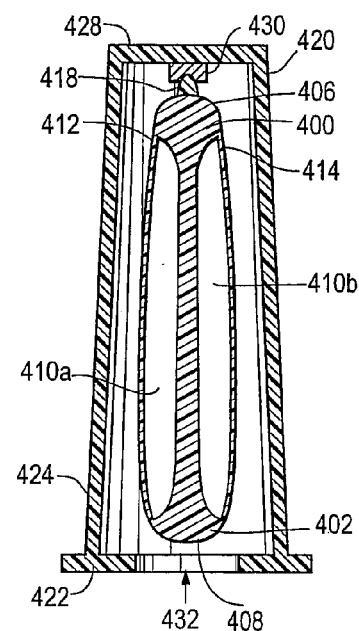

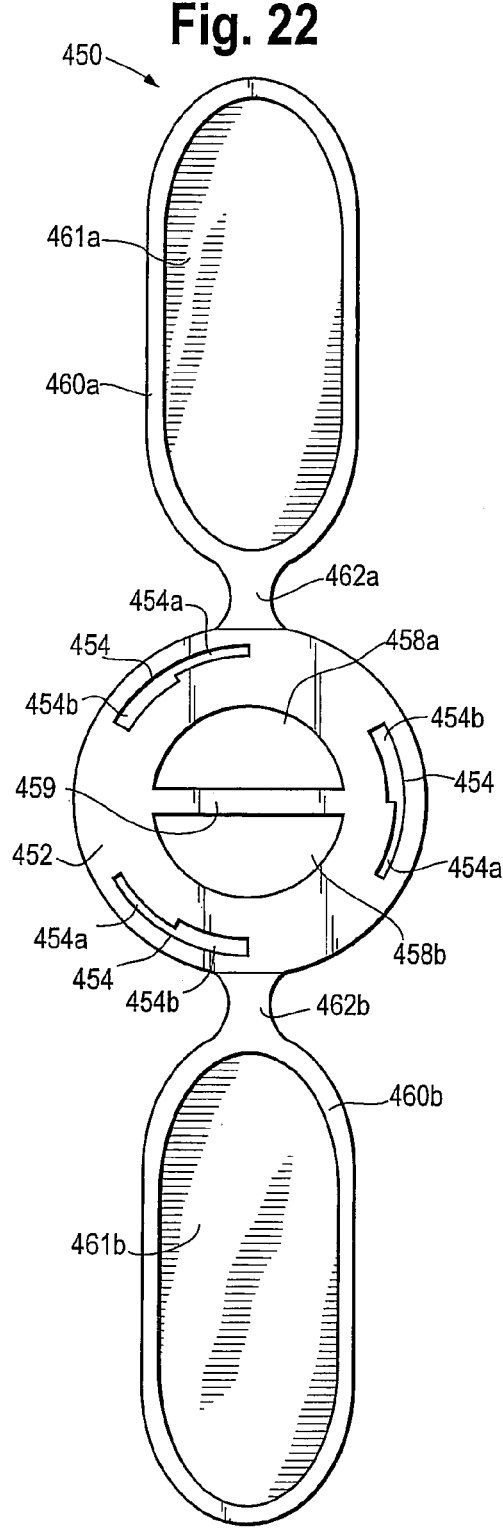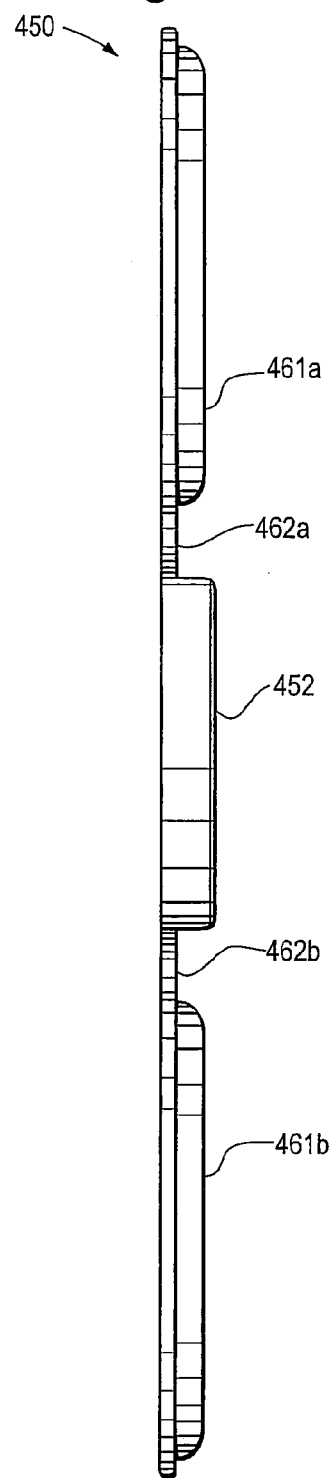

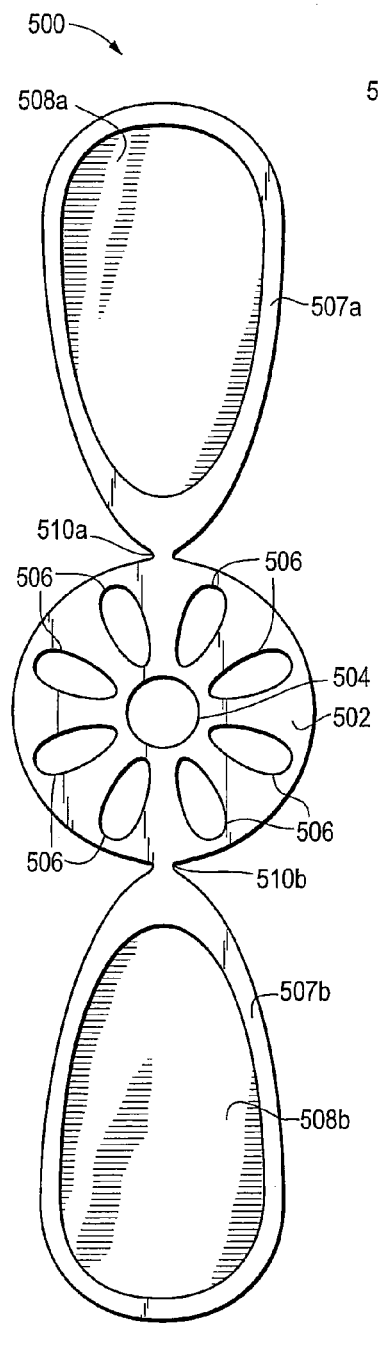
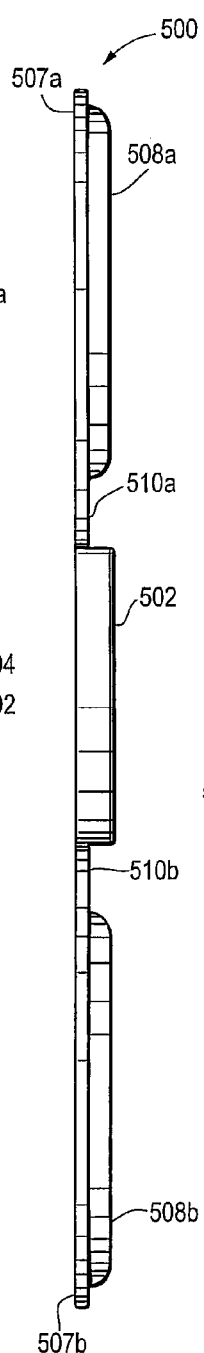
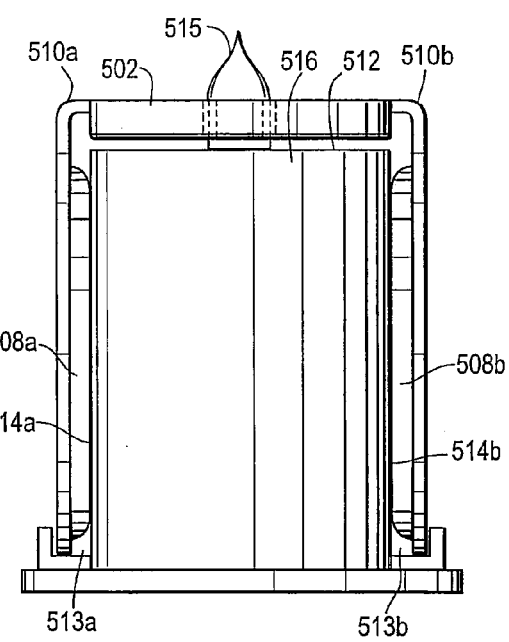
Fig. 25
Fig. 26
Fig. 27

ACTIVE MATERIAL EMITTING DEVICE

CROSS REFERENCE TO RELATED APPLICATIONS

This application is a continuation-in-part of U.S. application Ser. No. 11/050,242, filed Feb. 3, 2005, entitled "Device Providing Coordinated Emission of Light and Volatile Active", which claims the benefit of U.S. Provisional Application No. 60/541,067, filed Feb. 3, 2004, and a continuation-in-part of U.S. application Ser. No. 11/050,169, filed Feb. 3, 2005, entitled "Device Providing Coordinated Emission of Light and Volatile Active", which claims the benefit of U.S. Provisional Application No. 60/541,067, filed Feb. 3, 2004.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to active material emitting devices, and more particularly, to active material emitting devices and components thereof.

2. Description of the Background of the Invention

A multitude of active material emitting devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing active materials from active material emitting devices are also known in the art. For example, some devices include a heating element for heating an active material to promote vaporization thereof. Other devices employ a fan or blower to generate air flow to direct active material out of the diffusion device into the surrounding environment. In another type of device, active material may be emitted from the device using a bolus generator that delivers a pulse of air to eject a scent ring. Still other diffusion devices dispense active materials utilize ultrasonic means to dispense active materials therefrom.

In one example an active material emitting device includes two heaters for dispersion of fragrances. The device includes a housing, a plug extending from the housing for insertion into an outlet, and two containers having fragrances therein and wicks extending therefrom to absorb fragrances from the containers. Each of the heaters is disposed adjacent one of the wicks to heat the respective wick to vaporize the fragrances therein. Optionally, a CPU controlled by internal software may activate a first of the two heaters for a predetermined period of time. After the period of time expires, the CPU deactivates the first heater and thereafter activates the second heater.

Other active material emitting devices include a housing having a cavity for receiving a cartridge. The cartridge generally has a plurality of scent elements disposed on a rotatable disk. A blower is mounted in the housing to generate airflow by passing air across a scent element and out an aperture in the housing. The housing further includes rotating means that rotate the rotatable disk, thereby rotating the scent elements thereon. The device diffuses a first scent for a predetermined time period and thereafter rotates the disk to a second scent and diffuses the second scent for the predetermined time period. This process repeats itself until the last scent element is diffused for the time period and then the disk is rotated to a home position.

Piezoelectrically actuated vibratory type liquid atomization apparatuses are described in Helf et al. U.S. Pat. No. 6,293,474, Martin et al. U.S. Pat. No. 6,341,732, Tomkins et al. U.S. Pat. No. 6,382,522, Martens, III et al. U.S. Pat. No. 6,450,419, Helf et al. U.S. Pat. No. 6,706,988, and Boticki et al. U.S. Pat. No. 6,843,430, all of which are assigned to the assignee of the present application and which are hereby incorporated by reference herein. These patents describe an apparatus comprising a piezoelectric actuating element coupled to a liquid atomization plate. The piezoelectric actuating element vibrates the liquid atomization plate in response to alternating electrical voltages applied to the actuating element. The vibration of the plate causes atomization of a liquid supplied to it by a liquid delivery system. An electrical circuit is provided to supply the alternating electrical voltages to conductive elements that are in electrical contact with opposite sides of the actuating element. The conductive elements may also serve to support the actuating element and the liquid atomization plate in a housing that contains the device.

Various types of active material cartridges have been utilized both for solid, semi-solid, gel-like, and liquid active materials. For example, one type of cartridge for use with a heated device includes a reservoir with active material therein, a vapor permeable layer covering the reservoir for dispersion of vapor therethrough, and a vapor-impermeable layer disposed atop the vapor-permeable layer. The vapor-impermeable layer is peeled away from the vapor-permeable layer when it is desired to use the cartridge. The reservoir includes a centrally-disposed free-standing rib extending upwardly from a bottom surface of the reservoir and terminating slightly below the vapor-permeable layer so as to not interfere with the vapor-permeable layer.

Another cartridge for use in a passive device includes two reservoirs for active material, wherein each of the reservoirs includes a vapor permeable layer covering the reservoir for dispersion of vapor therethrough and a removable vapor-impermeable layer disposed atop the vapor-permeable layer. Removal of one or both of the vapor-impermeable layers allows dispersion of the active material into the surrounding environment. The two reservoirs are connected to one another by a flexible hinge.

Another cartridge for use in various active material emitting devices includes a rigid cylindrical body having a cylindrical inner compartment and a cylindrical outer compartment that surrounds the inner compartment. The inner compartment preferably includes a battery disposed therein for providing power to a fan and/or other components within an active material emitting device. The outer compartment includes a vaporizable material usually in the form of a packet having a semi-permeable covering.

A free-standing cartridge for emission of one or more fragrances includes one or more reservoirs for holding the one or more fragrances therein. The reservoir(s) may have the shape of a bottle or the like, and further include a dispensing opening that is preferably designed as a snap-off opening.

Another cartridge includes a cylindrical housing which is made of any suitable imperforate material. The housing includes an apertured top and bottom made of a rigid material such as plastic or metal. A battery is mounted in a central portion of the cylindrical housing, wherein an annular space is defined between the housing and an outer surface of the battery. A support strip material impregnated with an active material is mounted in the annular space, wherein the support strip material takes the form of an accordion pleat having folds, thereby forming air passageways between sections of the support strip material.

SUMMARY OF THE INVENTION

According to one aspect of the present invention, an active material cartridge comprises a frame and an active material refill. The active material refill comprises at least one reservoir having an active material therein And a protrusion extending from a first end thereof. The active material refill is disposed on and attached to the frame.

According to another aspect of the present invention, an active material cartridge comprises a frame and an active material refill. The refill comprises first and second reservoirs having active materials therein and joined to one another by a flexible connecting portion, wherein the refill is attached to the frame by flexing the refill about the connecting portion.

According to yet another aspect of the present invention, a holder for a light and active material emitting device comprises an inner shell and a skirt disposed over a bottom portion of the inner shell. The holder further includes an attachment structure secured to the inner shell such that the attachment structure secures the skirt in position. Still further, the holder includes an outer shell secured to the inner shell via the attachment structure.

According to still another aspect of the present invention, an active material and light emitting device comprises a base and a column extending upwardly from the base. The device further includes at least one LED that emits a flickering light that emulates a flame of a candle, wherein the LED is supported by the column. Still further, the device includes an active material cartridge attached to the column, an aperture disposed in the device for insertion of the cartridge into the device and for allowing air flow into the device, and attachment means for securing the cartridge to the column.

Other aspects and advantages of the present invention will become apparent upon consideration of the following detailed description.

BRIEF DESCRIPTION OF THE DRAWINGS

FIGS. 5B-5D are isometric exploded views of the active material emitting device of FIG. 3 during assembly thereof;

FIG. 8 is a top isometric view of the first embodiment of an active material cartridge;

FIG. 9 is a side elevational view of the cartridge of FIG. 8;

FIG. 10 is an exploded side elevational view of the cartridge of FIG. 9;

FIG. 14 is a bottom isometric view of a second embodiment of an active material cartridge;

FIG. 15 is a side elevational view of the cartridge of FIG. 14;

FIG. 18 is a top isometric view of a fourth embodiment of an active material cartridge a portion of the cartridge removed and in cross-section;

FIG. 19 is a top isometric view of the cartridge of FIG. 18 in a locked position with a portion of the cartridge removed and in cross-section;

FIG. 20 is a top isometric view of an active material emitting device;

FIG. 20A is a cross-sectional view taken generally along the lines 20A-20A of FIG. 20 showing a fifth embodiment of a cartridge in elevation;

FIG. 20B is a top isometric view of the cartridge of FIG. 20A;

FIG. 21 is a cross-sectional view taken generally along the lines 21-21 of FIG. 20 illustrating the cartridge of FIG. 20B;

FIG. 22 is a plan view of a sixth embodiment of an active material cartridge;

FIG. 23 is a side view of the cartridge of FIG. 22;

FIG. 25 is a plan view of a seventh embodiment of an active material cartridge;

FIG. 26 is a side elevational view of the cartridge of FIG. 25;

FIG. 27 is a front elevational view of an active material emitting device with the cartridge of FIG. 25 inserted therein;

DETAILED DESCRIPTION OF THE PREFERRED EMBODIMENTS

Figure 1:
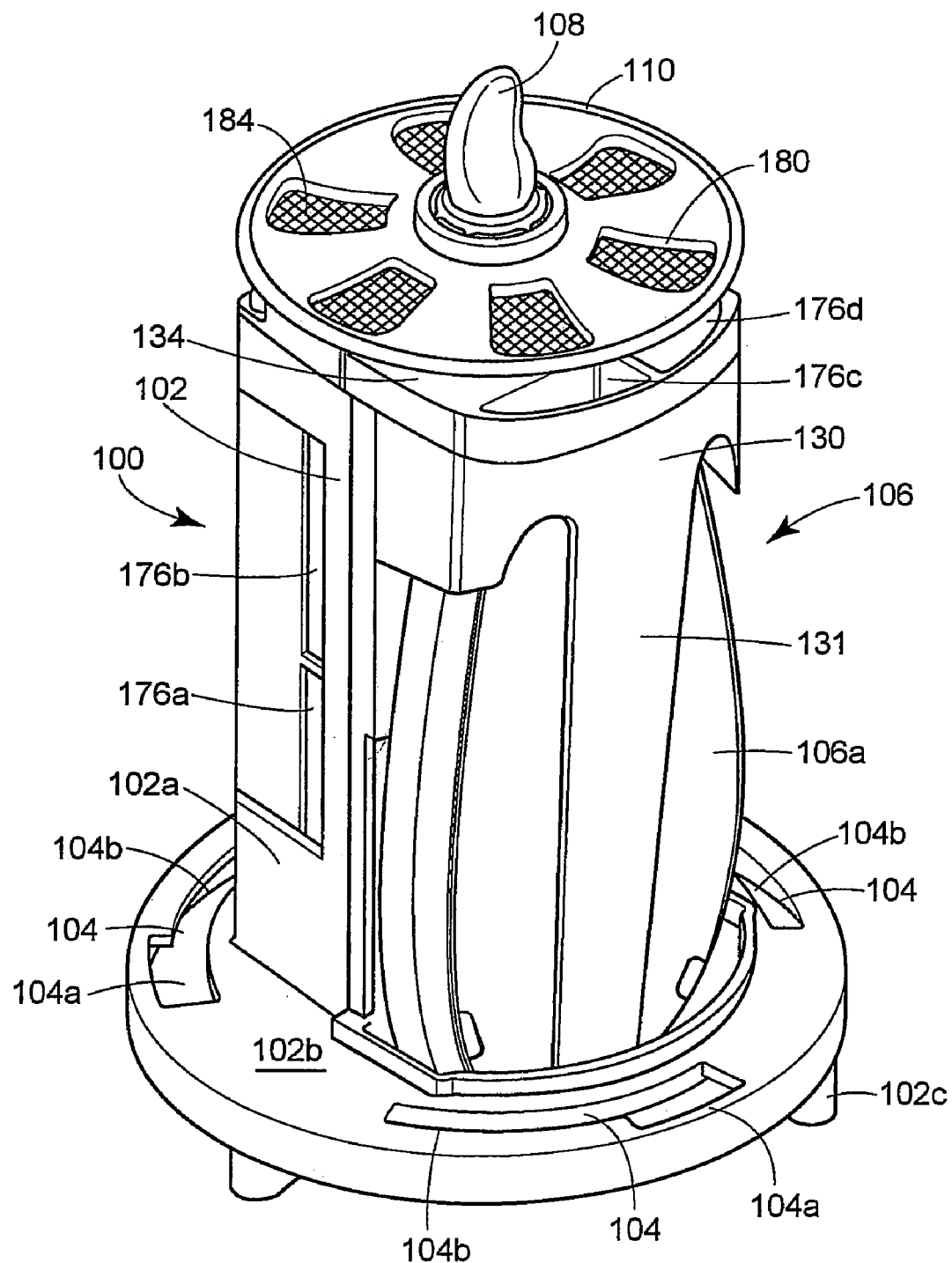
FIG. 1 is a top isometric view of an active material emitting device comprising a first embodiment of an active material cartridge.

The present invention comprises a device that emits both light and an active material. Preferably, the present invention comprises a single device that mimics both the visual and olfactory aesthetics of a scented candle, without an open flame and with an improved active material delivery system.

While a preferred embodiment of the present invention comprises emission of an active material, preferably a fragrance, we also contemplate that the dispenser of the present invention may alternatively dispense other active materials. Such alternate active materials may include, for example, disinfectants, sanitizers, insecticides, insect repellants, insect attractants, medicaments, air purifiers, aromatherapy scents, antiseptics, odor eliminators, air-fresheners, deodorizers, and such other active ingredients that are usefully dispersed into the air. As will be recognized by one of ordinary skill in the art, other active materials may also be introduced to the ambient environment via dispensers in much the same way as fragrances.

As generally seen in the figures, a device preferably emits both light and an active material. The device preferably includes an electrically-powered light source, an active material emitter, a power source, control circuitry, and a support structure. All of these components work together to preferably provide a fragrant aroma and the appearance of a flickering flame, the flickering effect being provided by the electrically-powered light source.

Light Source

The light source is an electrically-powered light emitting device. While the light source may comprise any number of conventional lighting devices (including, for example, incandescent, halogen, fluorescent, etc.), in preferred arrangements, the light source comprises one or more light emitting diodes (LED's). Preferably, the light source preferably includes two LED's.

An LED emits light of a dominant wavelength, or a very narrow range of wavelengths. (For purposes of simplicity, although we will refer to the dominant wavelength of the LED, that term should be interpreted to include a narrow range of wavelengths.) For instance, a blue LED will emit a dominant wavelength of light in the blue range of the color spectrum. This dominant wavelength is not substantially controllable for a given LED (although the dominant wavelength and intensity can drift slightly with temperature fluctuations, for instance). The intensity of the light, however, can be controlled for a given LED. For instance, LED's can be controlled by altering the applied current so as to vary the intensity of the light of the LED's dominant wavelength. This can be achieved by a number of means; however, pulse width modulation (PWM) is preferred. Preferably, a controller receives instructions from a memory or an outside source regarding the operation of the LED's. With PWM, the controller sets a duty cycle for each of the LED's, thus defining the ON times and the OFF times of the LED. During the ON times, i.e., during the pulse width, a current is supplied to the LED, and the LED emits light. Accordingly, altering the pulse width will alter the amount of time that the LED emits light. Thus, the diode flickers on and off as the duty cycle is repeated over time. When this repetition is accomplished at a relatively high frequency, the on and off of the diode is imperceptible to an observer. Thus, the light will be perceived by the observer to be constantly emitted. When such is the case, a flicker effect can be achieved by altering the duty cycles over time to increase and decrease the intensity of the emitted light. Alternatively, the flicker effect can be achieved when the frequency of the duty cycles is relatively lower, in which case the on and off times of the diode are perceptible to the observer, thus providing the flicker. Of course, combinations of these flicker methods are also possible. Thus, greater control can be achieved than in conventional lights which cannot be turned on and off as rapidly due to the time it takes to reach full intensity (e.g., heat the filament in an incandescent bulb) and cease light emission (e.g., wait until the filament cools). It would be recognized by one of ordinary skill in the art that, when using pulse width modulation to control one or more LED's, LED's that appear to be operating at substantially constant intensity and LED's that are flickering may both be flickering at a high frequency imperceptible to an observer. Thus, flickering and constant intensity light should be understood herein to refer to perceived effects.

Instead of altering the duty cycles, the controller may alternatively otherwise adjust how the current is supplied, thus altering the light emission properties of the LED's. For example, methods utilizing an analog sine wave or a digital potentiometer are generally known in the art.

Consequently, in LED lighting, an observer will observe a color corresponding to the dominant wavelength for the LED, and the variation in the pulse width will have a dimming effect. This method of controlling LED's is known in the art, and thus will not be discussed in more detail. Other methods of operating LED's are also known, and the use thereof would be obvious to one of ordinary skill in the art.

Figure 4:
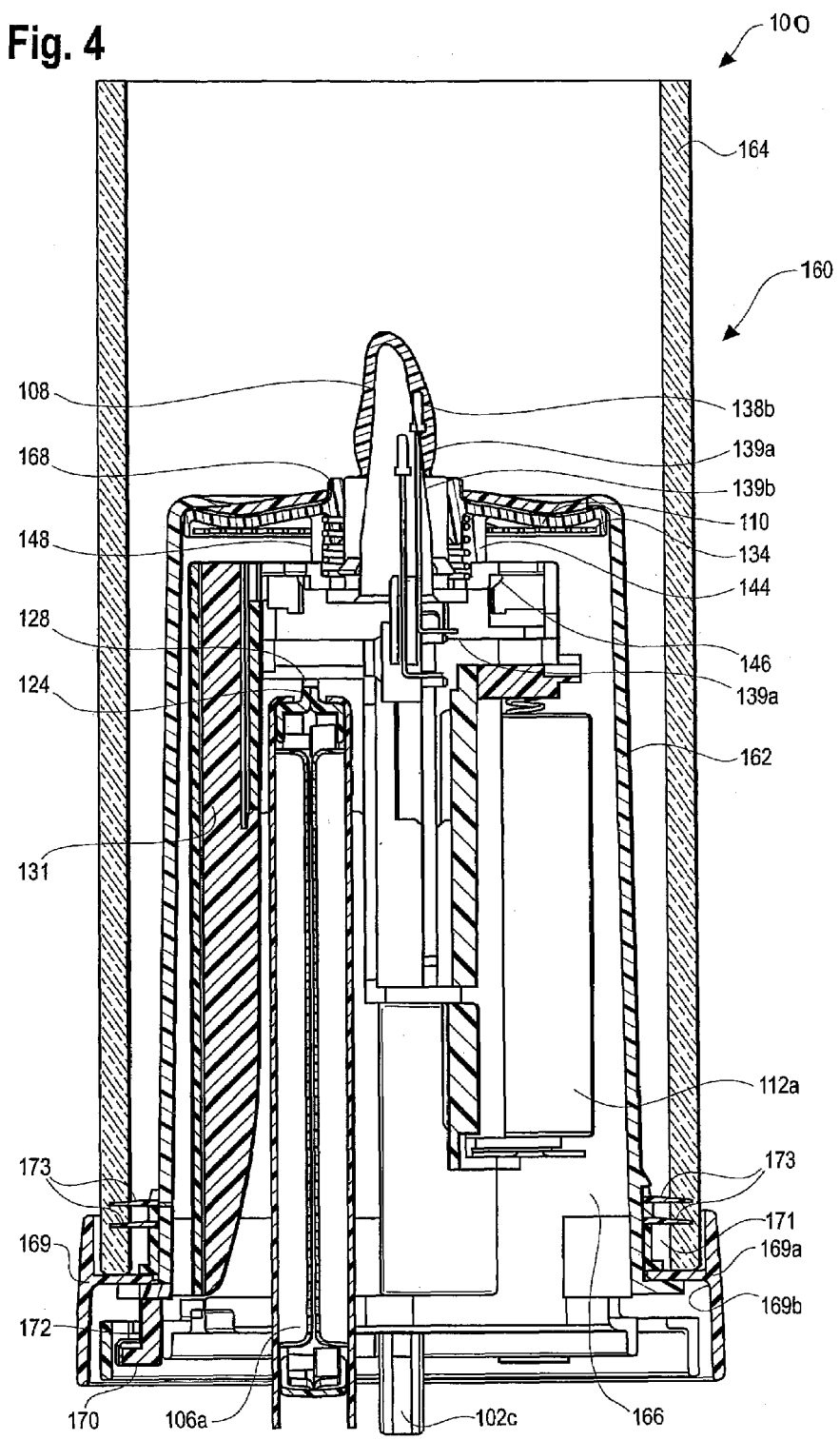
FIG. 4 is a cross-sectional view of the device of FIG. 3, taken generally along the lines 4-4 of FIG. 3.

When two LED's are used, the two LED's are preferably arranged one above the other (as best seen in FIG. 4), i.e., an upper LED is disposed on a side of a lower LED opposite to a base of the light and an active material emitting device. Preferably, the upper LED is controlled to emit light at a perceivable intermittence and/or varying intensity. For example, the pulse width of the LED may be adjusted over time to vary the perceived intensity or to provide perceivable intermittent on and off times for the LED. Thus, the flicker may be obtained by providing a constant (perceived) light emission of varying intensity, by providing an (perceived) intermittent light emission, or a combination of the two. In contrast to the upper LED, the lower LED is controlled such that light is perceived to be emitted substantially continuously and/or of a substantially constant intensity. This "continuous" light may be the result of a constant current being supplied to the LED or by providing a substantially constant pulse width over time, which gives the observer the perception of constant light when that LED is viewed on its own. Alternatively, the pulse width may be adjusted slightly over time to provide subtle intensity variations.

In this fashion, the LED's work to create a flicker effect. For example, when a conventional candle is lit, the base of the flame appears substantially steady, while the portion of the flame farther from the base of the wick flickers more apparently. The above-described arrangement of the LED's mimics this visual characteristic. It is preferred that LED's having a yellowish or amber hue be used. Specifically, it is preferred that the LED's used have a wavelength of emission in the range of from approximately 580 nanometers to approximately 600 nanometers, and it is even more preferred that the LED's used have a wavelength of emission in the range of from approximately 585 nanometers to approximately 595 nanometers.

Of course, modifications to the light source are possible. For example, a single LED may be used that is controlled to have a varying intensity and/or perceivable intermittence, thereby providing a flickering effect. A device using a single LED results in a lower cost apparatus that consumes less power. Alternatively, more than two LED's can be used, perhaps, to create the perception of a larger flame. Also, LED's of many colors are known and may be used, for example, to more closely resemble a flame by using hues that are reddish, orangish, and/or yellowish. The colors can also be made to change, for example, using RGB LED's (i.e., an array of red, green, blue LED's). By so varying the types of LED's used, as well as their arrangement, numerous aesthetics can be obtained, including varied colored shows, colored flames, and/or colored flickers. And, by adjusting the duty cycles of the LED's, the brightness of the light may also be reduced or intensified, as dictated by design preference. Optionally, colored LED's may be utilized in addition to or in lieu of creating a flicker effect with the LED's.

Moreover, when multiple LED's are used, it is not required that one LED provide a light emission of substantially constant intensity while the other LED provides a flicker effect. One or both may be held at a substantially constant intensity and one or both may emit flickering light.

Active Material Emitter

An active material emitter is preferably provided integrally with an active material emitting device. The active material emitter preferably includes a replaceable cartridge, having an active material in any one of a number of conventional forms, including gel and liquid forms. In such gel and liquid forms, the active material is generally incorporated with a carrier substance, for example, by impregnation, intermixture, coating, solubilization, or other means. The active material and carrier are disposed in a container, for example, a cartridge, a pouch, a bladder, a reservoir, or the like, and a portion of the container is formed such that the active material can permeate therethrough. For example, the active material may be emanated through the permeable portion when air passes thereover, or the active material may be vaporized by the application of heat to increase convection and emanated from the cartridge. In such a case, the dispenser may have a controllable heating device to vary the rate at which the volatile is released from the cartridge or a mechanical controller for controlling the airflow around the active material to be vaporized (such as a shield or fan).

The emission of the active material may also be enhanced or accelerated in various other manners. For example, the reservoir in which the active material resides may be formed of a metal material. Due to the heat conductive nature of the metal, the metal reservoir provides ambient heat to the active material, thereby enhancing vaporization of the active material. Further, a removable foil material may be disposed over a reservoir containing active material, wherein the foil may have printed ink or a resistor disposed thereon. When the foil material is removed from the reservoir, portions of the foil material may remain on a lip portion surrounding the reservoir. As with the metal reservoir, the heat conductive nature of the printed ink or resistor provides ambient heat to the active material therein.

Another type of active material emitter is a wick-based emanator, in which a liquid is drawn from a container, such as a reservoir, by a wick, via capillary action, and dispersed into the atmosphere. Additionally, the active material dispenser may use an atomizer to emanate the active material from the wick.

Specifically, this atomizer-type active material dispenser uses a wick to draw a liquid from a reservoir. An orifice plate, having minute tapered orifices therethrough is disposed in contact with the wick. Preferably, an actuator element made of, for example, a piezoelectric ceramic material is secured to the orifice plate. The actuator element is preferably annularly shaped and the orifice plate is preferably circular. Electrical power, in the form of a high frequency alternating voltage, is applied to the opposite upper and lower sides of the actuator element to produce electrical fields across the actuator element. These fields cause the actuator element to expand and contract in radial directions, causing the orifice plate to flex, such that a center region thereof vibrates in an axial direction (e.g., up and down). As a result of this vibration, the liquid passes through the orifices of the orifice plate, and is ejected from the upper surface of the orifice plate in the form of small droplets.

A more detailed explanation of this sort of atomization device may be found in commonly assigned copending U.S. patent application Ser. No. 10/412,911, filed Apr. 14, 2003, (published as U.S. Publication No. 2004/0200907), the disclosure of which is hereby incorporated by reference herein. In addition, a more detailed explanation of a support structure for the atomizing device may be found in commonly assigned copending U.S. patent application Ser. No. 10/241,215, filed Nov. 26, 2002, (published as U.S. Publication No. 2003/0069471), the disclosure of which is also hereby incorporated by reference herein.

Of course, other active material emitting devices may be substituted as desired in consideration of design choices, manufacturing costs, etc. Moreover, even within each type of dispenser, variations are possible, as would be appreciated by one of ordinary skill in the art.

Power Source

The power source supplies power to light the light source, and if required, to the active material emitter to aid in release of active material. For example, the power supply will supply voltages to the upper and lower surfaces of the actuator plate in the atomization-type active material dispenser discussed above. Additionally, the power source may be used to power additional components, for example, a fan, heater, or an sound component.

The power source may be a direct current (DC) power source that receives power from batteries of a transformer, or alternatively may be an alternating current (AC) power source. In a preferred embodiment, the power source comprises one or more batteries. When one battery is used, a voltage step-up or a charge pump (described in more detail below) may be used to ensure sufficient power to the components. The batteries may be replaceable, or they may be rechargeable. If rechargeable batteries are used, they may be removed for recharging, or an adapter may be provided on the device such that the batteries can be charged without being removed from the device. For instance, a receptacle may be incorporated into the device to receive a plug that supplies power from an electrical outlet.

It is not required, however, that the power source comprise batteries. For example, power for the device may be derived directly from an electrical outlet. As will be appreciated by one of ordinary skill, however, the use of alternate power sources may require that the device further include an AC to DC or an AC to AC converter.

Control Circuitry

As used throughout, the term "control circuitry" is intended to be a representative term that encompasses all controls that can be used with an active material emitting device. For example, the preferred embodiments are discussed below with reference to microcontrollers and/or circuit boards, which all constitute control circuitry. Further contemplated examples of control circuitry that may be used to embody the active material emitting device are an Application Specific Integrated Circuit (ASIC), a microprocessor, and an arrangement of one or more resistors, capacitors, and/or other components. Control circuitry may or may not include software. These examples of control circuitry are not limiting, however. Other control circuitry may also be used.

The control circuitry is generally used to control the operation of the device and is powered by the batteries. Specifically, the control circuitry is designed to provide the signals for controlling the operation of the light source. When one or more LED's are provided as the light source, the microcontroller may alter the duty cycles of the LED's to control the perceived intensity of the emitted light, thereby creating the candle-like flicker effect.

When at least two LED's are used, and one LED receives a constant current to emit light perceived to be substantially constant in intensity, that LED can be controlled separately from a circuit board, either to receive a power supply from the power source, when the device is turned on, or to not receive power, when the device is turned off. In other words, when one LED emits constant intensity light, it is not necessary to provide means for adjusting the pulse width within a duty cycle thereof (such as the microcontroller). In this case, the microcontroller may adjust the operation of only the LED's that flicker. In other embodiments, the constant emission LED may be controlled by pulse width modulation set by the controller such that the frequency of the pulse width is imperceptible to an observer. In this manner, the intensity of the constant emission LED may be varied slightly to add to the overall flicker presentation.

Also, when an active material emitting dispenser including an atomizer is used, the control circuitry may include circuits for converting power from the batteries to the high-frequency alternating voltage required to expand and to contract the actuator member, thereby emitting active material from the dispenser. In addition, the microcontroller may control a fan, a heating element, a sound component, or the like, to aid in dispersion of the active material. Furthermore, the microcontroller may include controls for automatically turning on and/or off one or all of the light source, the active material dispenser, and/or the sound component. For example, a timer may be included, and upon a predetermined elapsed time, some or all of the components will shut off. The sound component, as discussed above, may be any device which emits sound. Such sounds that may be emitted include, but are not limited to, music, the seashore, rain, animals, a waterfall, and the like.

The control circuitry may also serve other functions. For example, when batteries are used as the power source, it may be desirable to incorporate a charge pump. As is understood, LED's require a forward voltage to operate. While this forward voltage may vary depending on, for example, the color of the light emitted by the LED, the preferred LED's may require anywhere from approximately 1.8 volts to approximately 2.5 volts as a forward voltage, but typically require in the range of from approximately 2.0 to approximately 2.1 volts. The charge pump ensures that a supply voltage to the LED's exceeds the forward voltage of the LED's, when the voltage supplied by the batteries lessens, over time, to a voltage below the forward voltage. The charge pump uses one or more capacitors to store power in order to generate a voltage level greater than that supplied by the battery. Thus, the charge pump can boost the voltage level to greater than the forward voltage. In this manner, the LED's will continue to operate, even though the batteries are depleted to a point at which they are outputting a lower voltage. Consequently, a single set of batteries can power the device for a longer period of time than if no charge pump were used.

In addition, the control circuitry may incorporate a constant current source, which ensures that a constant current is applied to the LED's, regardless of the battery voltage. Otherwise, a higher voltage and corresponding LED current would be supplied at the beginning of the life of the batteries, which would trail off as the batteries are used. This would lead to an observer perceiving a brighter flicker when a new set of batteries is installed, and having that intensity wither as the battery output decreased to the forward voltage or below, at which point the charge pump would activate. Thus, by providing a constant current source, the LED's can emit a light having a constant intensity over time, which prevents a noticeable dimming as the batteries begin to lose power. When a charge pump is used, however, current is not constantly supplied to the LED's. Because there must be a time interval during which the charge pump charges, the power provided through the charge pump is by its nature intermittent. Therefore, a constant current is not supplied to the LED's, and thus the constant current source would not function properly, when a charge pump is operating.

However, it is possible to supply a constant average current to the LED's, via a constant average current source. In a constant average current source, a current is supplied during a portion of a cycle to achieve an average current over the cycle that would equate to the constant current that would otherwise be provided. Specifically, where a constant current source supplies a constant current to each of the two LED's, a constant average current source supplies (i) a current (typically constant) to the first LED for a portion of a cycle (the cycle is set based on preferred design aspects and is not the same as the duty cycle referred to with respect to the light intensity modulation of the LED's), (ii) a current (typically constant) to the second LED for another portion of the cycle, and no current to either LED during a final portion of the cycle. For instance, when two LED's are provided, a constant current source would supply a constant current of, for example, 15 mA to the first LED and 15 mA to the second LED when the LED's are enabled. However, for example, a constant average current source supplies 45 mA to the first LED for one-third of a cycle and 45 mA to the second LED for another one-third of the cycle, with no current being supplied during the final one-third of the cycle. Alternatively, because the voltage may slightly decline over the two-thirds of the cycle in which the LED's are enabled, the LED enabled directly after charging may appear slightly more intense than the second LED enabled. Accordingly, an alternative cycle for driving the LED's could consist of, in order, a first one-sixth in which neither LED is enabled, a second one-sixth in which the first LED is enabled, a third one-sixth in which the second LED is enabled, a fourth one-sixth in which neither LED is enabled, a fifth one-sixth in which the second LED is enabled, and a final one-sixth, in which the first LED is enabled. In this manner, the first LED is enabled directly after charging half of the time, and the second LED is enabled directly after charging the other half of the time. Thus, in both examples, the average current supplied to the LED's is the same as that provided by the constant current source; however, in this manner, no current is provided to either LED during a portion of the cycle, thus reserving a time gap for the charge pump to operate. Consequently, when the charge pump is activated, there is no change in operation since the charge time is already a dedicated part of the cycle. As would be understood by one of ordinary skill, the cycle used by the average current source should be of a sufficiently high frequency that the LED's will be perceived to be constantly emitting light (or to be emitting a perceived flicker, as discussed above).

Many combinations of one or more of the charge pump, the constant current source, and the constant average current source may be used. For example, a constant current source may be used until such time that the charge pump is activated, and thereafter a constant average current source may be used. For the sake of convenience, the term current source controller will be used herein to refer to a mechanism for providing a constant current or a constant average current. This may be achieved with a constant current source, a constant average current source, or a combination thereof.

The control circuitry may also include controls to shut the device down when the batteries discharge to a point below a certain voltage. In this way, the device will not continue to draw power from batteries that are dying, thus lessening the risk that the batteries will leak battery acid. Additionally, the control circuitry may be designed, in conjunction with sensors and/or switches to allow only operation of the LED's when an active material emitter is disposed in the device.

Support Structure

The active material emitting device also includes a support structure, provided to support the light source, the active material emitter, the power source, and the control circuitry, or some combination thereof. The term "support structure" is intended to encompass any and all of a chassis, a housing, a holder, and a base, as those terms are used in the description, as well as similar structures used to support or contain the features of the active material emitting device.

Active Material Emitting Device

Having generally described the components of active material emitting device above, discussion will now be made of specifics of a light and active material emitting device including various novel arrangements of the above-described components, as well as additional features.

An active material emitting device 100 is depicted in FIGS. 1-7. Although the devices herein are referred to as active material emitting devices, any of such devices may also emit light therefrom. The device 100 includes a chassis 102 comprising a chassis base 102b and a chassis column 102a extending upwardly from the chassis base 102b. The chassis base 102b and chassis column 102a may be formed integrally or as separate, attachable pieces. The chassis 102 may also include additional components. For example, one or more feet 102c may depend from the chassis base 102b, the feet 102c being attachable to the chassis base 102b, or formed integrally therewith. Additionally, as shown in FIG. 1, one or more apertures or slots 104 are formed through the chassis base 102b. As illustrated, the slots 104 preferably accommodate a bayonet-type connection and comprise a wider portion 104a and a narrower portion 104b. The slots 104 will be described in more detail below.

Figure 2:
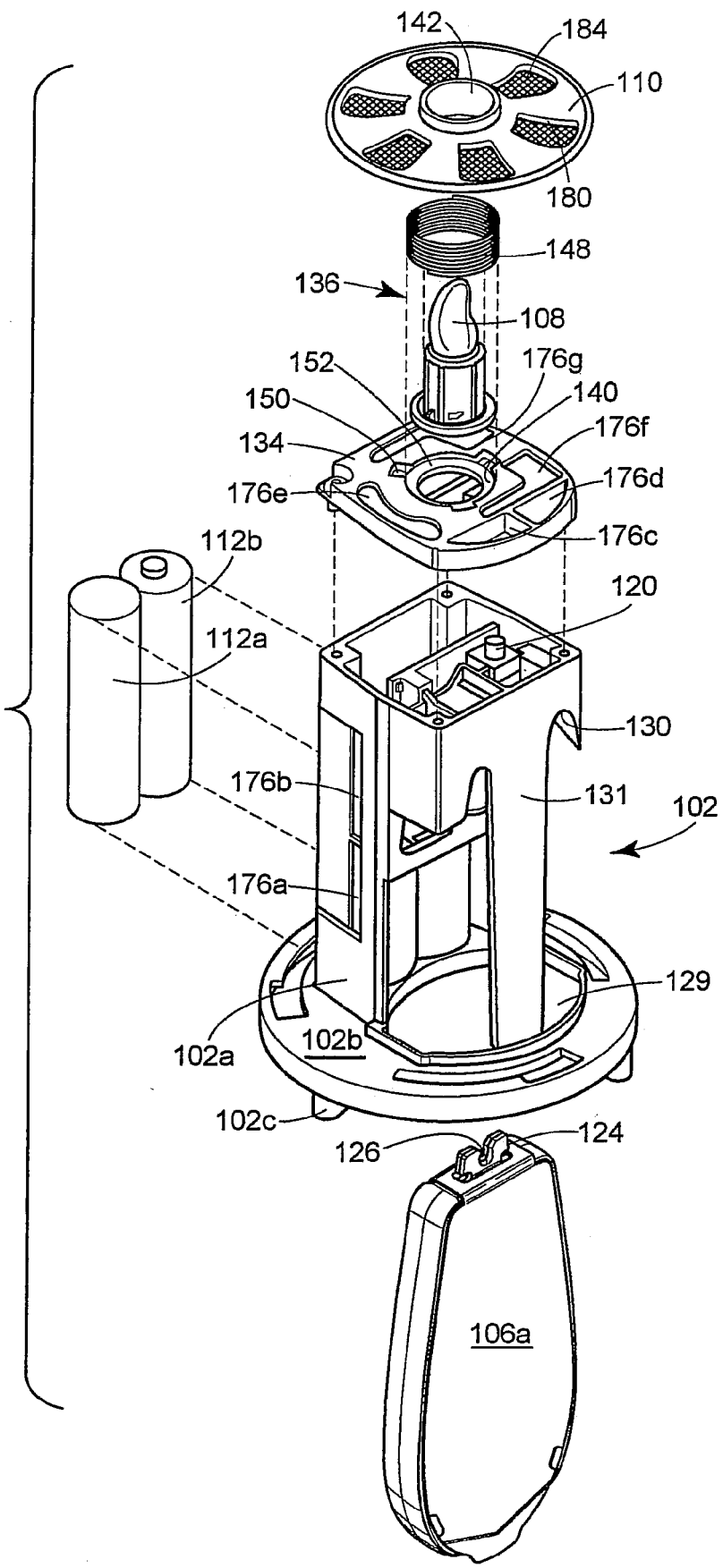
FIG. 2 is an exploded view of the device of FIG. 1.
Figure 5:
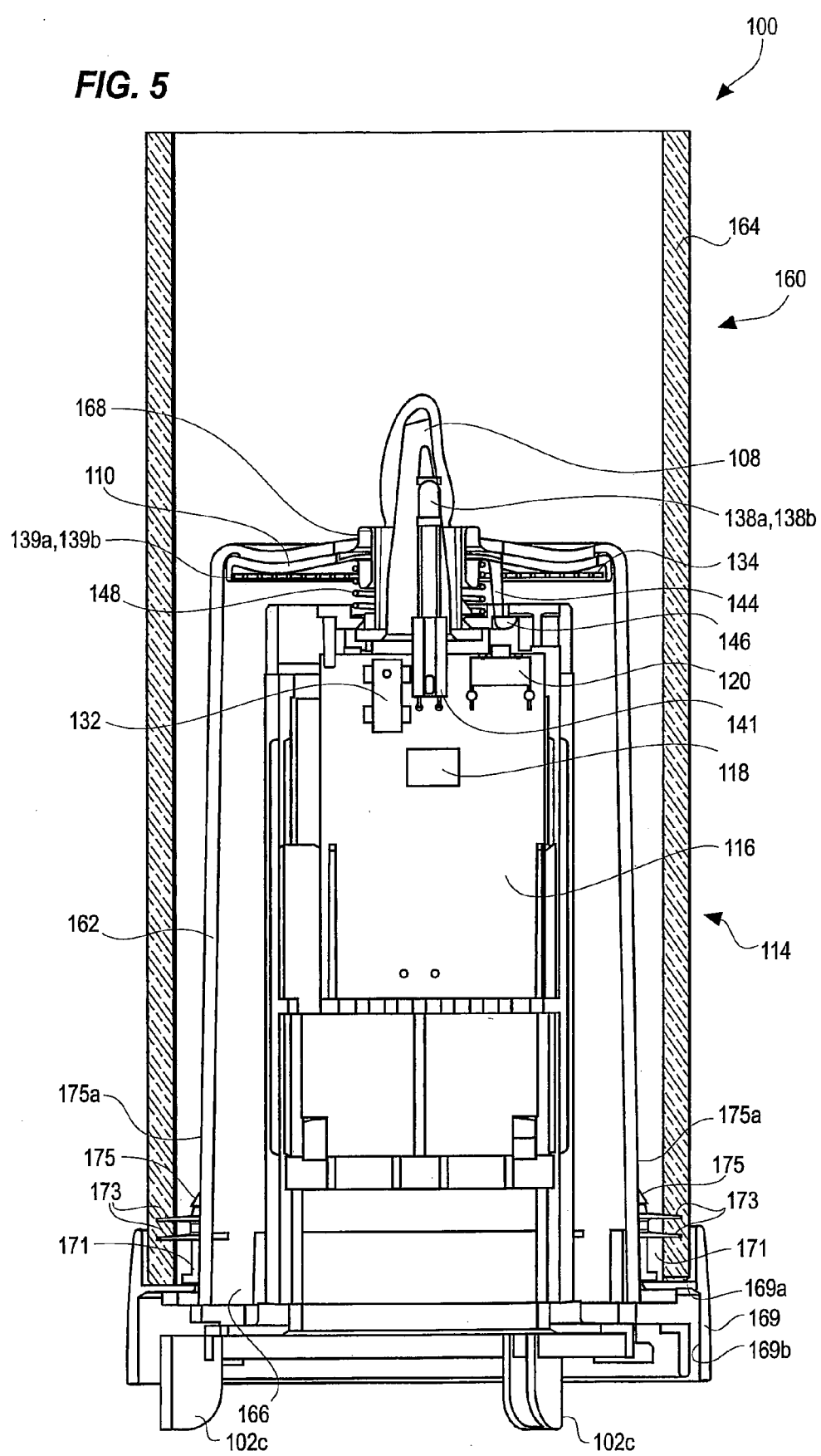
FIG. 5 is a cross-sectional view of the device of FIG. 3, taken generally along the lines 5-5 of FIG. 3.

Referring to FIGS. 1 and 2, an active material emitter 106, a light-emitting tip 108, a collar 110, two batteries 112a, 112b, and controls 114 (FIG. 5) are preferably disposed on the chassis 102. The batteries 112a, 112b are preferably removably detachable from the chassis 102, so they may be replaced and/or recharged as necessary. As seen in FIG. 5, the controls 114 preferably include a printed circuit board (PCB) 116, a controller 118 (e.g., an ASIC, a microcontroller, or the like), and two switches 120, 132, which act in conjunction with power supplied from the batteries 112a, 112b (FIG. 2) to operate the device 100.

In this embodiment, the active material emitter 106 is preferably a replaceable active material cartridge 106a that is removably securable to a cartridge mount disposed on the chassis 102. The active material cartridge 106a is preferably a passive active material emitter, but may alternatively be any other type of active material cartridge that dispenses active material in any other fashion known in the art. More specifically, the releasable active material is preferably contained within a gel or liquid and is emitted into the air over time. Accordingly, active material is emitted as a result of airflow over the cartridge 106a, and no power is needed to emit the active material into the air. As discussed above, however, an emission accelerator, such as a fan or heater may also be used in conjunction with the device 100 to increase the rate at which active material is emitted.

Figure 6:
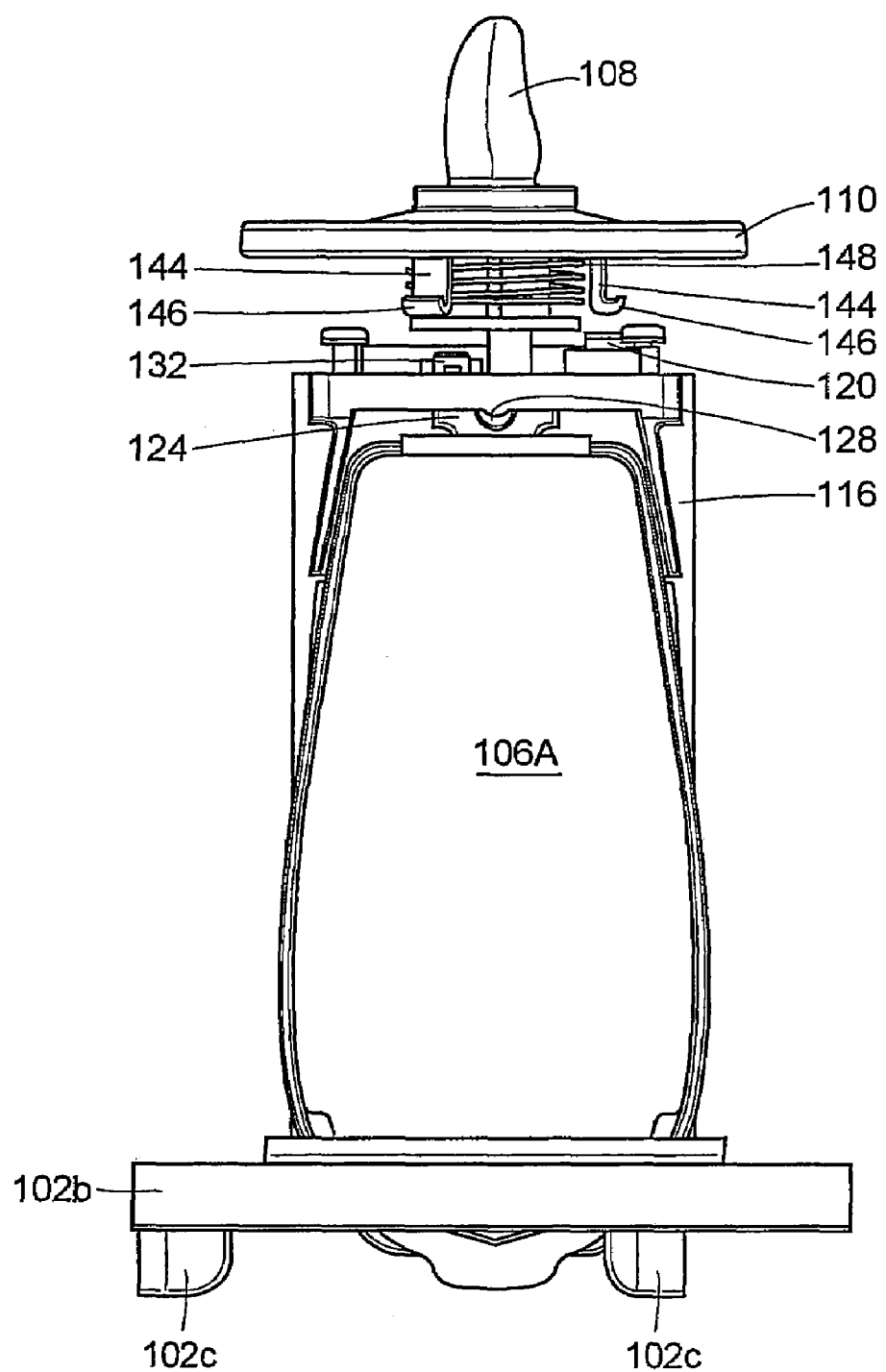
FIG. 6 is a front elevational view of the device of FIG. 1 illustrating of an active material cartridge.

As shown in FIGS. 2 and 6, the cartridge 106a includes a protrusion 124 in which a substantially U-shaped opening 126 is formed. The chassis column 102a has disposed thereon, or formed integrally therewith, a post 128 (FIGS. 4 and 6), which serves as the cartridge mount. Specifically, the opening 126 formed on the cartridge 106a and the post 128 are designed such that the post 128 snap-fits within the opening 126, thereby attaching the active material cartridge 106a to the chassis 102. In this embodiment, the cartridge 106a is introduced and removed from the chassis 102 through an opening 129 (FIG. 2) formed through the chassis base 102b. This opening 129 also allows for airflow around the cartridge 106a to aid in release of the active material from the cartridge 106a, as will be discussed in more detail below. As the cartridge 106a is inserted into the device 100, a guidance structure 130 having a support post 131 (FIGS. 1, 2, and 4) that extends from the chassis column 102a to the chassis base 102b guides the cartridge 106a into engagement with the post 128 such that walls defining the opening 126 on the cartridge 106a engage the post 128 in a snap-fit fashion. Downward force on the cartridge 106a disengages the walls defining the opening 126 from the post 128 such that the cartridge 106a may be removed from the device 100. The specific components of the cartridge 106a will be discussed in detail hereinafter.

Alternative methods are contemplated for securing/removing the active material cartridge 106a to/from the chassis 102. For example, the cartridge 106a may be attached and removed from a side of the chassis 102, in which case the U-shaped opening 126 may not be necessary. Instead, a circular opening may be sufficient to receive the post 128 therein. Additionally, the post 128 and opening 126 may not be provided at all. In such case, a circular opening in the cartridge 106a may receive a barbed post protruding from the chassis 102. Optionally, the chassis 102 and cartridge 106a may be designed so that an interference fit is formed therebetween to secure the cartridge 106a to the chassis 102. These examples are given only by way of example. Numerous cartridge mounts and cartridge configurations are contemplated, and would be known to one of ordinary skill in the art. Any means by which a replaceable active material cartridge may be removably attached to the chassis are contemplated. Preferably, the active material emitting device utilizes a mechanism for engaging and retaining the cartridge 106a in a snap-fit fashion.

Figure 7:
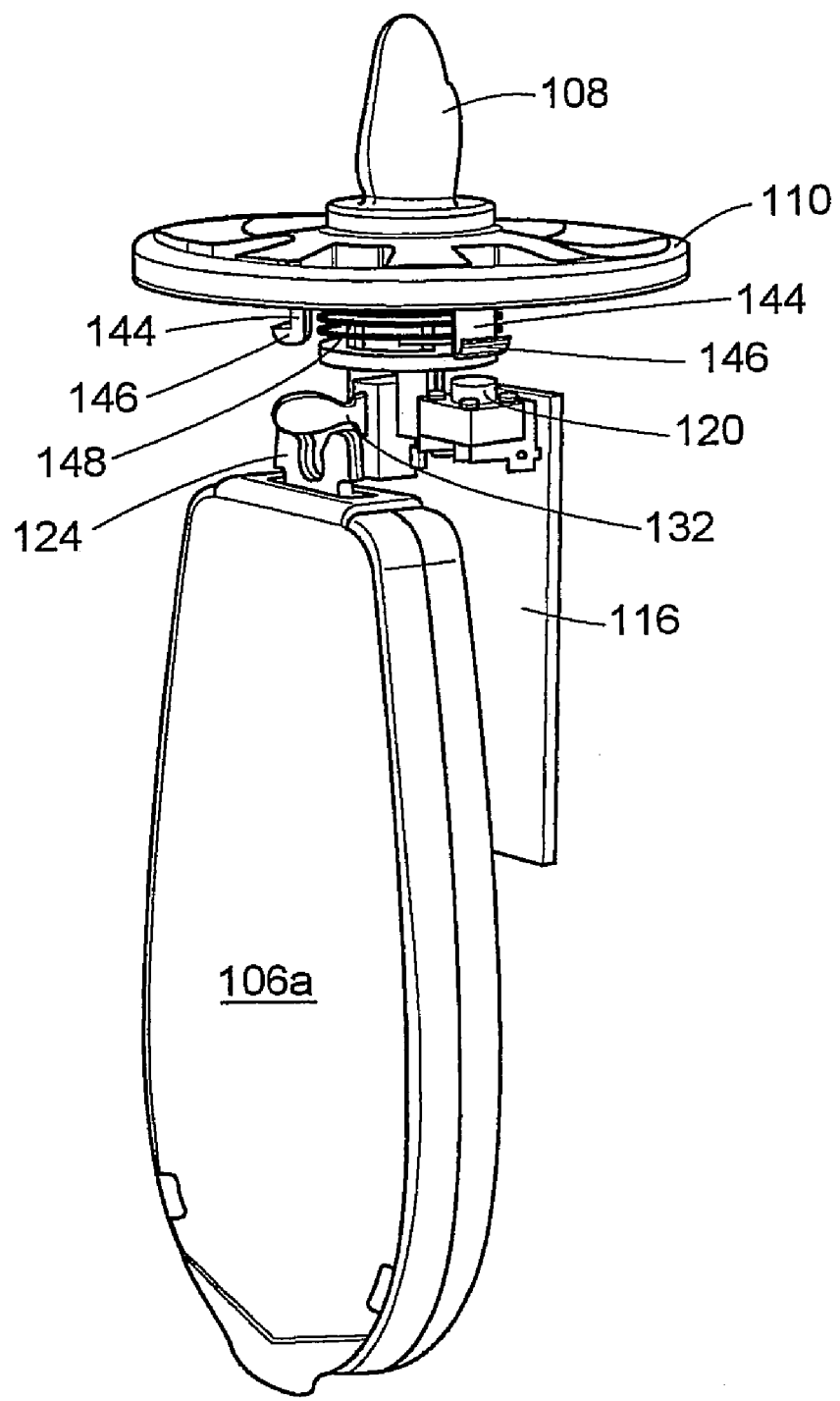
FIG. 7 is a top isometric view of the device of FIG. 1 illustrating an interaction between the active material cartridge and a lever.
Figure 11:
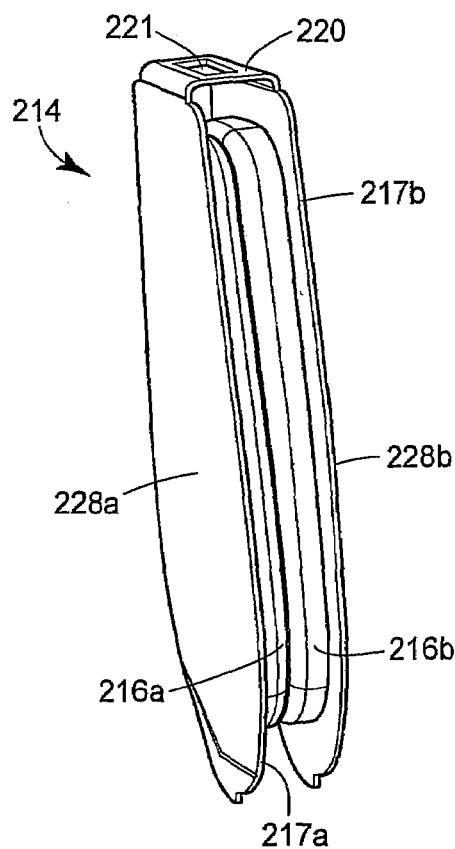
FIG. 11 is a top isometric view of the cartridge of FIG. 8 with a frame removed therefrom.
Figure 12:
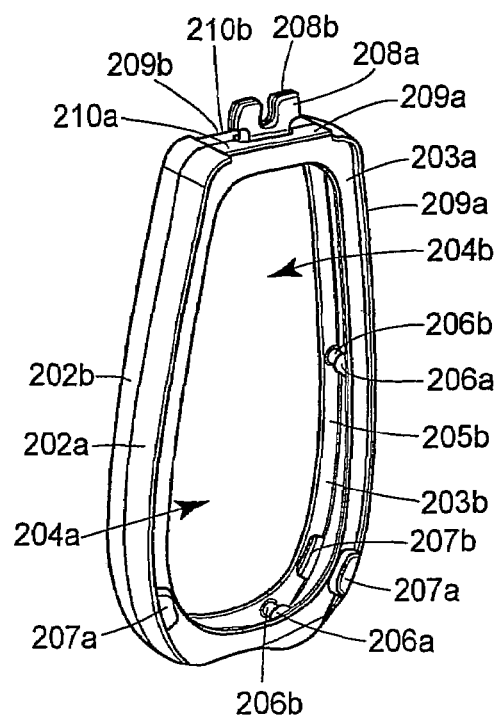
FIG. 12 is a top isometric view of the cartridge of FIG. 9 with active material reservoirs removed therefrom.
Figure 12A:
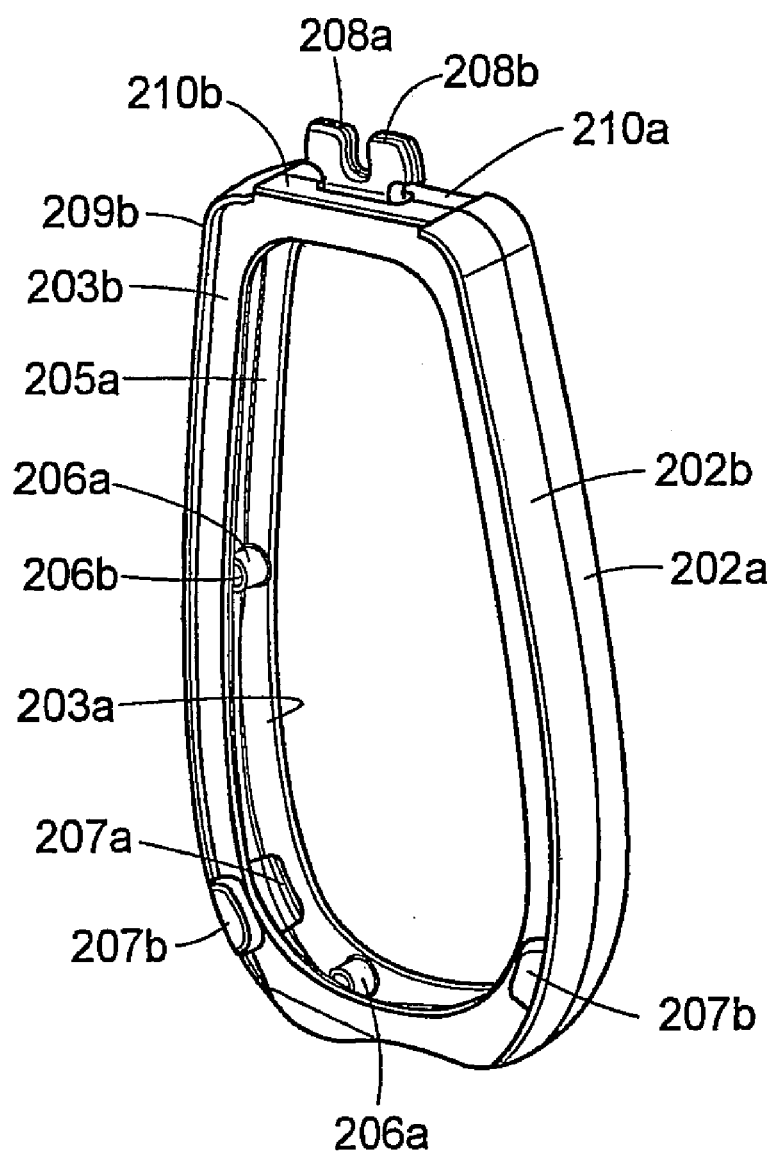
FIG. 12A is a top isometric view of the cartridge of FIG. 9 with active material reservoirs removed therefrom.

As a further feature of this embodiment, means are also provided for detecting the presence of the active material cartridge 106a. For example, the device 100 may be controlled such that the LED's will only emit light when an active material cartridge 106a is inserted into the device 100. As shown in FIGS. 5 and 7, a cartridge detector switch 132 is disposed on the chassis 102, wherein the cartridge detector switch 132 extends outwardly from the PCB 116. The cartridge detector switch 132 is movable between a normal position and an actuated position, and only when the cartridge detector switch 132 is in the actuated position will the LED's emit light. For example, the normal position of the cartridge detector switch 132 may be at an angle of less than 90 degrees to the PCB 116. An actuated position may be perpendicular to the PCB 116 (FIG. 7). Thus, as the active material cartridge 106a is attached to the chassis 102, a portion of the cartridge 106a, preferably the post 128, will contact the cartridge detector switch 132 and move it in the direction of insertion to the actuated position, thereby actuating the cartridge detector switch 132. This mechanical switch is provided only by way of example. One of ordinary skill in the art would recognize that other types of switches and/or sensors could similarly be used to detect the presence of the active material cartridge 106a.

Referring now to FIGS. 4 and 5, the tip 108 is preferably disposed at a top portion 134 of the chassis 102, and disposed therein is a light source 136. Preferably, two LED's 138a, 138b, as discussed above, are arranged one above the other within the tip 108. Light emitted from the LED's 138a, 138b is diffused by, and transmitted through, the tip 108. As depicted in FIG. 2, the tip 108 is a separate component of the device 100 that is disposed within a bore 140 formed in the top portion 134 of the chassis 102. The tip 108 may also be formed integrally with the chassis 102. By making the tip 108 a separate piece, however, the tip 108 may be replaceable, e.g., with other differently constructed, or colored, tips. Also, a separate tip 108 may be formed of a material other than that used for the chassis 102. Preferably, the tip 108 may be formed of one or more of plastic, glass, wax, and the like. Additionally, the tip 108 may be formed of a glow-in-the-dark material or of a material that continues to glow for a time after the LED's 138a, 138b are shut off.

The LED's 138a, 138b each include leads 139a, 139b extending therefrom, as seen in FIGS. 4 and 5. Preferably, the leads 139a, 139b extend from the LED's 138a, 138b into a spacer device 141 (FIG. 5), which is attached to the PCB 116 by any known means, that spaces the leads 139a, 139b from one another. This spacing prevents the LED's 138a, 138b from shorting out, thereby increasing the life of the LED's 138a, 138b.

As further seen in FIGS. 2, 4, and 5, the collar 110 is preferably disposed at the top portion 134 of the chassis 102. The collar 110, while shown as a separate component, may also be integral with the chassis 102. The collar 110 has an aperture 142 (FIG. 2) formed axially through the center thereof, and a portion of the tip 108 is preferably disposed within the aperture 142. The collar 110 is preferably actuable with respect to the chassis 102. Preferably, a user actuates the collar 110 from a home position to turn the LED's 138*a*, 138*b* on and off. For example, as shown in FIGS. 4, 5, and 7, the collar 110 may have one or more tines 144 extending downwardly therefrom, and a lip 146 that extends outwardly from a distal end of each of the tines 144. A spring 148 is disposed between the chassis 102 and the collar 110 inside the tines 144 to bias the collar 110 away from the chassis 102. As shown in FIG. 2, a plurality of tine-receiving bores 150 (one for each of the tines 144) is formed in the top portion 134 of the chassis 102, wherein each bore 150 includes a shoulder 152. The tines 144 of the collar 110 are received within the bores 150, and the lip 146 of each of the tines 144 contacts the shoulder 152 to maintain attachment of the collar 110 to the chassis 102. Thus, when the collar 110 is actuated downwardly against the bias of the spring 148, the tines 144 slide downwardly within the bores 150. When pressure on the collar 110 is released, the bias of the spring 148 returns the collar 110 to the normal, or rest position. As seen in FIGS. 6 and 7, the switch 120, which is preferably an on/off switch, is preferably disposed beneath one of the tines 144, such that actuation of the collar 110 causes one of the tines 144 to actuate an actuator arm of the on/off switch 120, thereby turning the LED's 138*a*, 138*b* on or off.

Figure 3:
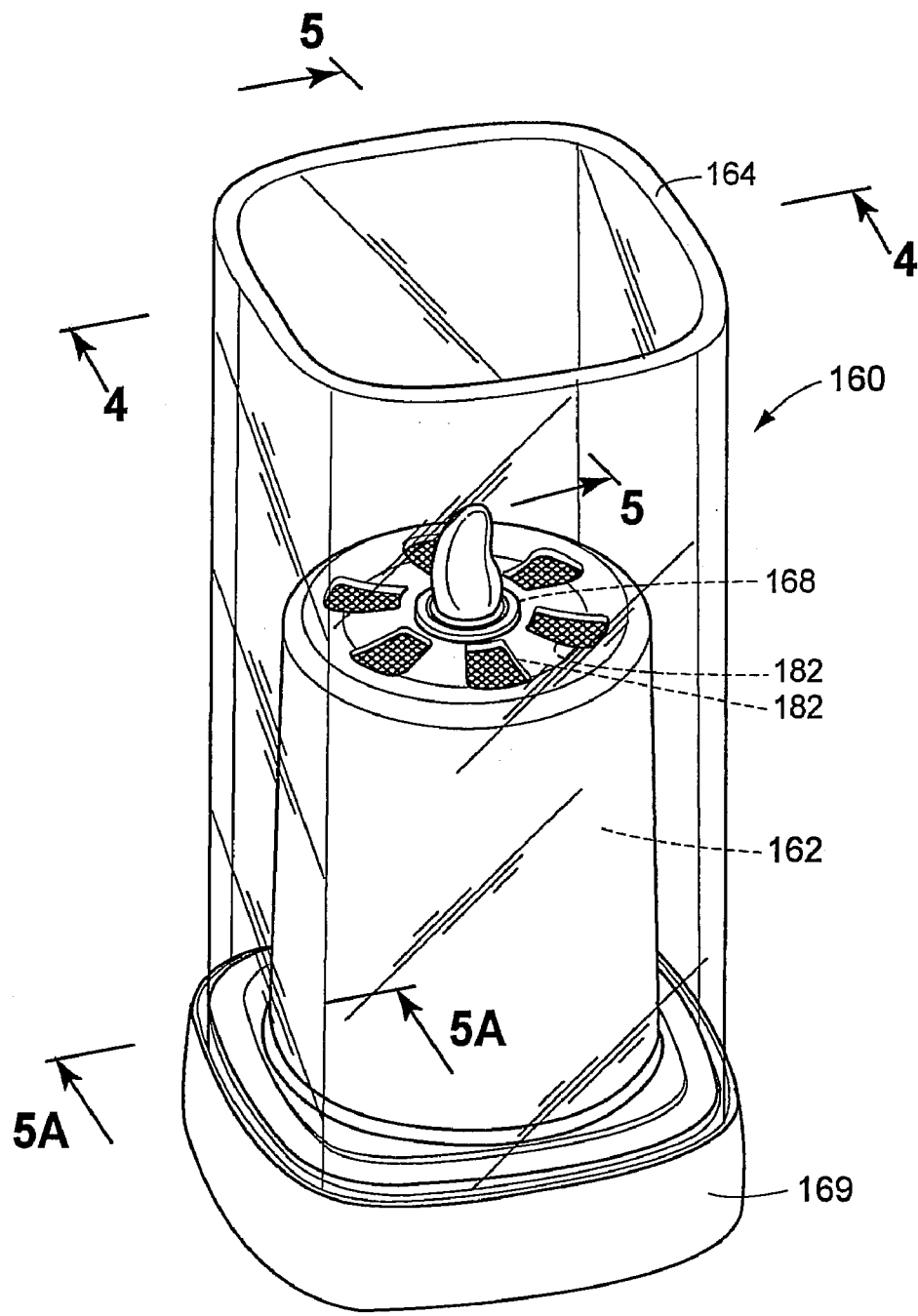
FIG. 3 is a top isometric view of the device of FIG. 1 in combination with a holder.

The device 100 shown in FIG. 1 and described to this point is a unitary device 100 that emits both a flickering light and an active material, preferably a fragrance. While this device 100 could be used as a stand-alone device 100, it is preferably used with a holder 160, as shown in FIGS. 3, 4, and 5.

The holder 160 preferably includes an inner shell 162 and an outer shell 164. The inner shell 162 preferably includes an open bottom end 166 and an aperture 168 formed centrally through a top thereof. When the holder 160 is lowered onto the unitary device 100, the tip 108 passes through the aperture 168, and an underside of the top of the inner shell 162 contacts the collar 110. In this manner, the holder 160 is rotatable with respect to the unitary device 100, i.e., the unitary device 100 remains stationary while the inner shell 162 (and the remainder of the holder 160) rotate on the collar 110.

As seen in FIG. 4, one or more feet 170 extend radially outwardly from downwardly-extending legs 172 depending downwardly from the open bottom end 166 of the inner shell 162. The feet 170 are sized to pass through the wider portion 104*a* of the slots 104 formed in the chassis base 102*b* when the holder 160 is placed on the unitary device 100, but will not pass through the narrower portion 104*b* of the slots 104. The thickness of the legs 172, however, is less than the width of both the wider portion 104*a* and the narrower portion 104*b* of the slots 104. Thus, the holder 160 is attachable and removable from the unitary device 100 only when the feet 170 are aligned with the wider portions 104*a* of the slots 104. Once the feet 170 and legs 172 have been aligned with and are inserted through the wider portion 104*a* of the slots 104, the inner shell 162 and the chassis base 102*b* are rotated relative to one another, thereby securing the inner shell 162 to the chassis base 102*b*. When the holder 160 is lowered completely onto the unitary device 100, the feet 170 are situated below the chassis base 102*b*, such that the legs 172 are disposed in the slots 104. In this position, the holder 160 may rotate upon counter-rotation of the holder 160 and the unitary device 100, with the rotation being constrained by the slots 104.

The outer shell 164 is preferably made of material through which the light emitted by the LED's 138*a*, 138*b* will pass. Although the outer shell 164 is depicted as being made of glass, the outer shell 164 may optionally be made of plastic, wax, or the like. Additionally, the outer shell 164 may diffuse the light emitted by the LED's 138*a*, 138*b*. This diffusion may be in addition to the diffusion accomplished by the tip 108, or the tip 108 may not diffuse the emitted light (or may not be included), and only the outer shell 164 diffuses the light. The outer shell 164 may also be made of various colors, and may have formed thereon various colors, patterns, designs, and the like, depending upon the desired aesthetic.

Figure 5A:
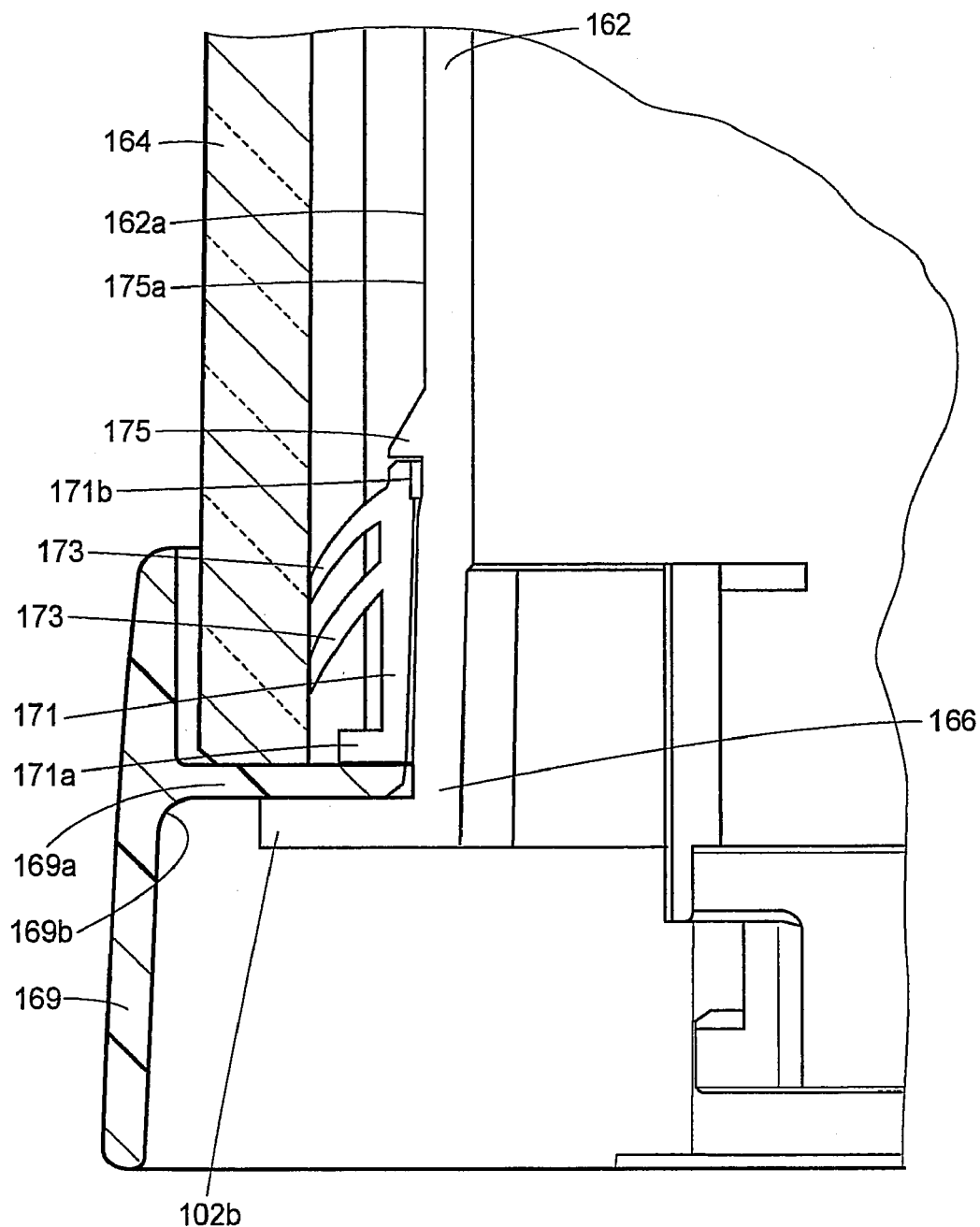
FIG. 5A is an enlarged fragmentary cross-sectional view taken generally along the lines 5A-5A of FIG. 3.

As seen in FIGS. 4, 5, and 5A the holder 160 also includes a skirt 169 having a continuous inwardly directed projection 169*a* extending from an inside surface 169*b* of the skirt 169. The holder 160 also preferably includes a flexible attachment structure 171 made of any suitable elastomeric or thermoplastic material that aids in connecting the outer shell 164, inner shell 162, and skirt 169. Referring to FIGS. 5A-5C, the attachment structure preferably includes a foot portion 171*a*, a circular inner peripheral flange 171*b*, and continuous outer peripheral flexible outer flanges 173.

Figure 5D:
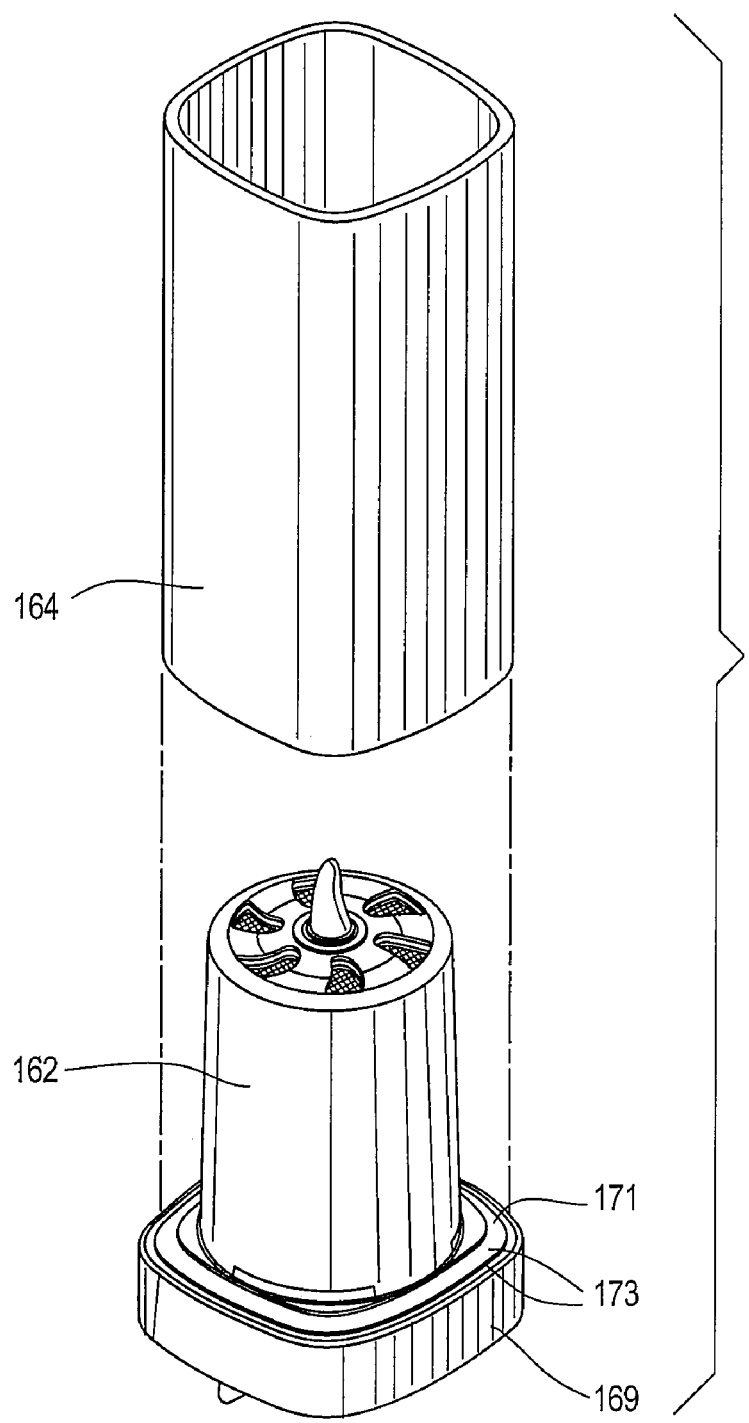

FIGS. 5B-5D depict the assembly of the device 100. Preferably, the inner shell 162 is attached to the chassis base 102*b* by a bayonet-type connection, as described in greater detail hereinbefore. Thereafter, the skirt 169 is inserted over the inner shell 162 as seen in FIG. 5B such that the inwardly directed projection 169*a* of the skirt 169 rests upon the chassis base 102*b*, as seen in FIG. 5A. Preferably, the inner shell 162 has one or more rigid barbs 175 disposed about an outer surface 162*a* of the inner shell 162. As best seen in FIGS. 5A and 5C, the flexible attachment structure 171 is inserted over and is slid down the outer surface 162*a* of the inner shell 162 such that the inner peripheral flange 171*b* is inserted over the rigid barbs 175. The attachment structure 171 is placed in a recess 174 such that a foot portion 171*a* of the attachment structure 171 rests against the projection 169*a* of the skirt 169 and such that the inner peripheral flange 171*b* of the attachment structure 171 abuts the barbs 175. In this position, the foot portion 171*a* of the attachment structure 171 aids in retaining the skirt 169 in its position against the chassis base 102*b* and the interference between the barbs 175 and the inner peripheral flange 171*b* retains the attachment structure 171 on the inner shell 162. Although the barbs 175 are depicted as being discontinuous, the barbs 175 may be replaced by a single annular shoulder that extends fully around the outer surface 162*a* of the inner shell 162.

Once the skirt 169 and attachment structure 171 are inserted over the inner shell 162, the outer shell 164 is inserted over the inner shell 162 as seen in FIG. 5D. As the outer shell 164 is inserted thereover, the outer peripheral flanges 173 flex downwardly within a gap between the inner and outer shells 162, 164, thereby creating a frictional fit between the inner and outer shells 162, 164. Optionally, although not preferred, the outer shell 164 may be manually removed from the inner shell 162 by pulling the chassis base 102*b* (if fully assembled) and outer shell 164 relative to one another, thereby overcoming the frictional fit. The outer peripheral flanges 173 may extend fully and continuously about an outer surface 171*c* of the attachment structure 171 or may discontinuously extend about one or more portions thereof. Optionally, peripheral flanges may be disposed in a continuous or discontinuous manner on an inner surface of the outer shell 164 and may engage a portion of the inner shell 162, or a structure secured to the inner shell 162, to create a similar interference fit. Still optionally, any other known attachment structures or means known in the art are contemplated.

The inner shell 162 and the outer shell 164 may be formed as a unitary holder 160, or may be individual components that are assembled after manufacturing. Furthermore, the skirt 169 of the holder 160 may be purely decorative, and/or it may be used as a means for securing the inner shell 162 and the outer shell 164 together. As should be understood, when the holder 160 is situated on the unitary device 100, because the top of the inner shell 162 is in contact with the actuatable collar 110, downward actuation of the holder 160 will result in downward actuation of the collar 110, thus turning the LED's 138a, 138b on and off, as described above.

As can also be seen in FIGS. 4 and 5, when the holder 160 is placed on the unitary device 100, the inner shell 162 and the chassis base 102b define a substantially enclosed cavity in which the active material cartridge 106a, batteries 112a, 112b, and controls 114 are disposed. The tip 108 extends upwardly from the substantially enclosed cavity, through the central aperture 168 in the inner shell 162. As described above, however, the preferred active material cartridge 106a is a passive release system that requires airflow thereacross to release the active material into the air. Accordingly, it is necessary to allow for airflow through the cavity and across the active material cartridge 106a. Preferably, this airflow is achieved through convection. In particular, apertures are formed through the top and bottom of the substantially enclosed cavity. For example, various vent holes 176a-176g (FIGS. 1 and 2) are created throughout the chassis column 102a and chassis base 102b. As described above, an aperture 129 through which the active material cartridge 106a is inserted and removed is formed through the chassis base 102b. Additionally, as shown in FIGS. 1 and 2, collar apertures 180 are formed through the collar 110 to allow passage of air, and venting apertures 182 (FIG. 3) are formed through the top of the inner shell 162. Thus, when a portion of the collar apertures 180 is aligned with a portion of the venting apertures 182, a passageway is formed through which air can flow between the ambient environment and the substantially enclosed inner cavity. In addition, as should be understood, rotating the holder 160 with respect to the unitary device 100, i.e., rotating the holder 160 within the slots 104, controls airflow through the collar apertures 180 and the venting apertures 182 by exposing more or less of the collar apertures 180 vis a vis the overlaying venting apertures 182. With this arrangement, ambient air preferably enters the device 100 through the aperture 129 formed through the chassis base 102b, and leaves through the collar apertures 180 and venting apertures 182, as well as other vent holes 176a-176g throughout the device 100. Still further, a porous media 184 preferably in the form of a screen is disposed below and secured to the collar 100. The porous media 184 is preferably visually obscuring in order to conceal the components of the device 100, but is also extremely porous in order to limit the obstruction of air flow through the media 184 and collar apertures 180. The porous media 184 is preferably formed of a spunbonded polypropylene, but alternatively may be formed of any polymeric material, metal, or any other known porous media, and combinations thereof. Optionally, the porous media 184 may be molded integrally with the collar 110. Preferably, the porous media 184 makes the device 100 more aesthetically pleasing by hiding the inner components of the device 100. Although the porous media 184 is depicted as a single unitary porous media 184, the porous media 184 may also be formed of multiple portions that are disposed below each of the collar apertures 180.

Modifications to this embodiment are contemplated. For example, providing differently patterned apertures, more or fewer apertures, and/or larger or smaller apertures can alter airflow through the device. For example, apertures may be provided through the sides of the inner shell 162 of the holder, in addition to, or instead of, the venting apertures 182 provided on the top of the inner shell 162. Also, the collar apertures 180 and/or the venting apertures 182 may be made larger or smaller.

Additionally, while the collar 110 is described as being movable up and down with respect to the chassis 102 to turn the LED's 138a, 138b on and off, the collar 110 may alternatively be rotatable with respect to the chassis 102, to turn the LED's 138a, 138b on and off. Optionally, the collar 110 may not be actuatable at all, and one or more switches may be provided on an exterior of the device to turn the LED's 138a, 138b on and off. Additional switches may also be provided to control lighting characteristics of the device 100. For example, switches may be provided to switch between different light shows, or different color LED's 138a, 138b.

Two or more of the same or different active material emitting devices as discussed hereinabove may be incorporated into a combination device. Illustratively, two of the active material emitting devices as seen in FIG. 3 may be incorporated into a combination device, wherein a first active material emitting device has a first height or other dimension and a second active material emitting device has a second height or other dimension less than the first height or other dimension. Various other combination devices may be created by using any number of active material emitting devices having any combination of heights.

Active Material Cartridges

The active material cartridge 106a is seen in further detail in FIGS. 8-12A. The active material cartridge 106a includes a frame 200 having first and second frame portions 202a, 202b. The first frame portion 202a includes a ledge 203a extending inwardly from an inner periphery thereof and forming an aperture 204a extending through the first frame portion 202a. The first frame portion 202a further includes cylindrical sockets 206a extending from a back surface 205a of the ledge 203a and two tabs 207a extending inwardly from a flange 209a (FIG. 12) of the frame portion 202a. Still further, a protrusion portion 208a extends upwardly from a top portion 210a of the first frame portion 202a. Similarly, the second frame portion 202b includes a ledge 203a extending inwardly from an inner periphery thereof and forming an aperture 204b through the second frame portion 202b. The second frame portion 202b further includes pins 206b extending from a back surface 205a of the ledge 203b and two tabs 207b extending inwardly from a flange 209b (FIG. 12) of the frame portion 202b. Further, a protrusion portion 208b extends upwardly from a top portion 210b of the second frame portion 202b.

The first and second frame portions 202a, 202b are secured to one another in any suitable fashion such that the frame portions 202a, 202b form the integral frame 200 and the protrusion portions 208a, 208b form an integral protrusion 208. The pins 206b of the second frame portion 202b are press-fit within the sockets 206a of the first frame portion 202a. Optionally, the posts 206a, 206b may be secured by any other suitable fastening means, including, for example, heat staking, rivets, press fit, snap fit, ultrasonic welding, adhesives, or the like and combinations thereof.

The active material cartridge 106a includes an active material refill 214 having at least one reservoir 216b as shown of FIG. 8, but preferably includes first and second reservoirs 216a, 216b with first and second active materials, respectively, disposed therein, as seen in FIG. 10. The first and second active materials may be the same, or optionally, may be different. As seen in FIGS. 9-12A, each of the reservoirs 216a, 216b includes a lip portion 217a, 217b surrounding the respective reservoir 216a, 216b. The lip portions 217a, 217b are joined to one another in any suitable fashion at top portions 218a, 218b thereof by a connecting portion 220 having an aperture 221 therethrough, thereby forming the unitary refill 214. Each reservoir 216a, 216b includes an inner surface 222a, 222b and an outer surface 224a, 224b, respectively. The inner surfaces 222a, 222b of the reservoirs 216a, 216b preferably abut one another, but optionally may be spaced slightly from one another if desired. Each of the outer surfaces 224a, 224b of each reservoir 216a, 216b includes a non-removable vapor permeable thermoplastic layer 226a, 226b secured across the outer surface 224a, 224b of the respective reservoir 216a, 216b. Further, removable vapor impermeable foil layers 228a, 228b are disposed atop the respective vapor permeable sealing layers 226a, 226b. Before the cartridge 106a is inserted into the device 100, the vapor impermeable layers 228a, 228b are preferably removed from the reservoirs 216a, 216b to expose the vapor permeable layers 226a, 226b, thereby allowing the active materials therein to permeate through the vapor permeable layers 226a, 226b. Such reservoirs 216a, 216b, vapor permeable layers 226a, 226b, and vapor impermeable layers 228a, 228b are discussed in greater detail in Martens, III et al. U.S. Pat. No. 4,849,606, owned by the assignee of the present application, and hereby incorporated by reference herein.

When the active material cartridge 106a of FIGS. 8-12A is assembled, the frame portions 208a, 208b are joined at respective posts 206a, 206b and thereafter, the refill 214 is positioned within the frame portions 202a, 202b such that the lip portions 217a, 217b fo the reservoirs 216a, 216b, respectively, are retained between the respective ledge 203a, 203b and the respective tabs 207a, 207b. The reservoirs 216a, 216b extend into the respective aperture 204a, 204b such that the bottom surfaces 222a, 222b the reservoirs 216a, 216b either abut one another or are spaced slightly from one another, as noted above. Optionally, the reservoirs 216a, 216b may be secured within the frame portions 202a, 202b with an adhesive, the like, or any other attachment means known in the art may be utilized.

Figure 13:
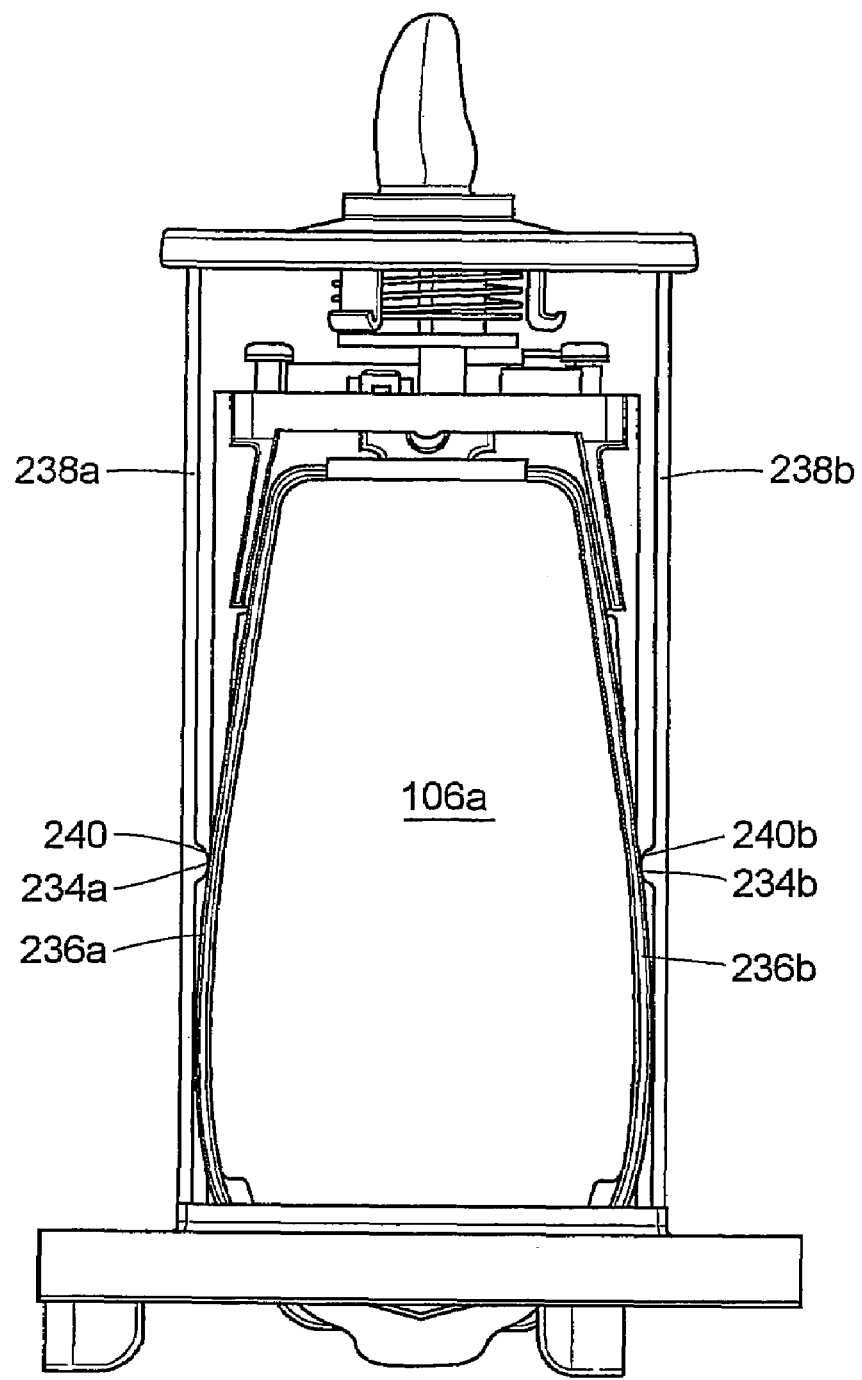
FIG. 13 is a front elevational view of the cartridge of FIG. 8 with detents.

As seen in FIG. 13, the cartridge 106a may optionally include first and second detents 234a, 234b formed in side portions 236a, 236b of the frame 200. If the detents 234a, 234b are utilized, a chassis, a column, a shell, or another component of the device 100 with opposing walls 238a, 238b may include tabs 240a, 240b extending therefrom so as to engage the detents 234a, 234b when the cartridge 106a is inserted into the device 100, thereby aiding in retaining the cartridge 106a in the device 100. As described above with respect to the device 100 of FIGS. 1-8, the cartridge 106a is inserted into an appropriately shaped recess within an active material emitting device (reference number 129 in FIG. 2).

The present invention may comprise a second embodiment of an active material cartridge 250 as seen in FIGS. 14 and 15. the cartridge 250 may be used with a modified version of the active material emitting device 100 as described in connection with FIGS. 1-7 or any other embodiment of an active material emitting device. The cartridge 250 includes a frame 252 and a refill 254, wherein the frame 252 includes a base portion 256 with first and second posts 258a, 258b extending from a top surface 260 of the base portion 256 and a handle 262 extending from a bottom surface 263 of the base portion 256. Preferably, a connecting post 265 is integral with and extends between the posts 258a, 258b, wherein the connecting post 265 is spaced from the base portion 256. The refill 254 is similar to the refill 214 of the embodiment of FIGS. 8-13 and includes first and second reservoirs 264a, 264b having active materials therein. A lip portion 265a, 265b surrounds the respective reservoir 264a, 264b, wherein the lip portions 265a, 265b are joined to one another at top portions 266a, 266b thereof by a connecting portion 268. Each reservoir 264a, 264b includes a bottom surface 270a, 270b and a top surface 272a, 272b, respectively, wherein the bottom surfaces 270a, 270b are preferably, although not necessarily, spaced slightly from one another. Each top surface 272a, 272b includes a non-removable vapor permeable sealing layer 274a, 274b and a removable vapor impermeable layer 276a, 276b disposed atop the vapor permeable sealing layer 274a, 274b, respectively, as discussed in detail above with respect to the embodiment of FIGS. 8-13.

When the embodiment of FIGS. 14 and 15 is assembled, the refill 254 is inserted over the frame 252 such that the connecting portion 268 of the refill 254 abuts the connecting post 265 of the frame 252 and the posts 258a, 258b are disposed between the bottom surfaces 270a, 270b of the reservoirs 264a, 264b. Preferably, one or more of the posts 258a, 258b extends beyond the connecting portion 268 when the cartridge 250 is assembled. The lip portion 265a, 265b surrounding each reservoir 264a, 264b is connected to the base portion 256 of the frame 252 by heat-staked posts 280a, 280b. Optionally, any other known fastening means may be utilized, including welding, press-fitting, adhesives, or combinations thereof. Preferably, the cartridge 250 is assembled during manufacture thereof.

The cartridge 250, as depicted in FIGS. 14 and 15, may be inserted into an appropriately shaped recess in an active material emitting device such as the device 100 of FIGS. 1-7, preferably by grasping the handle 262 of the cartridge 250. Also preferably, the cartridge 250 is inserted through a bottom portion of an active material emitting device 100, but may instead be inserted through a top or side portion of the device 100. As the cartridge 250 is inserted into the device 100, the one or more posts 258a, 258b that extend beyond the connecting portion 268 of the refill 254 may depress or actuate an actuator arm 269 of a switch 270 disposed in the device 100, as depicted in FIG. 15, thereby alerting the device 100 that the cartridge 250 has been inserted into the device 100. Any type of switch 270 known in the art may be utilized.

Figure 16:
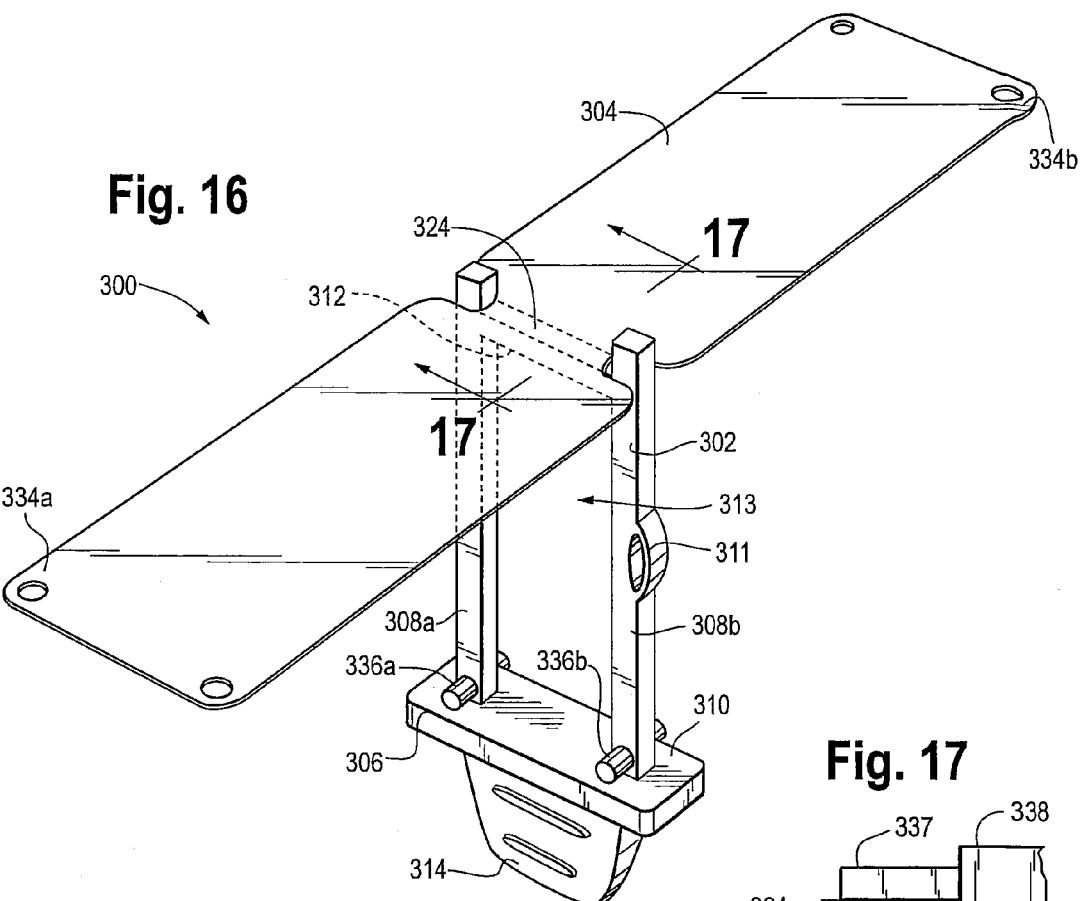
FIG. 16 is a top isometric view of a third embodiment of an active material cartridge illustrating the cartridge partially assembled.
Figure 17:
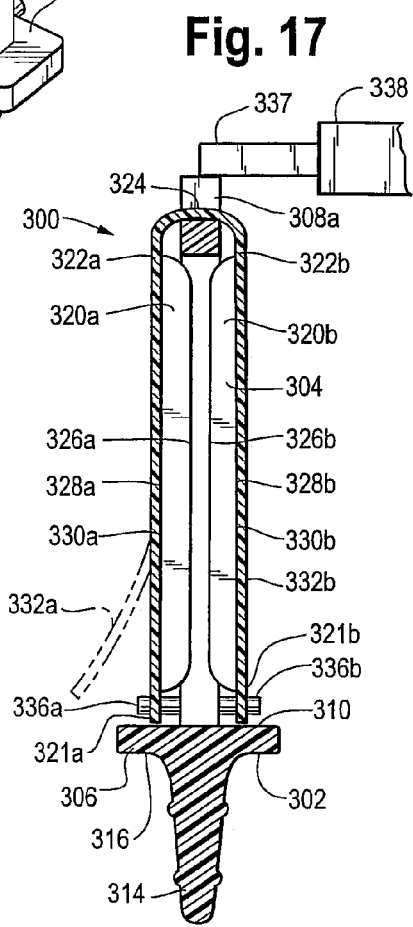
FIG. 17 is a cross-sectional view of the cartridge of FIG. 16 fully assembled, and taken generally along the lines 17-17 of FIG. 16.

A third embodiment of an active material cartridge 300 is depicted in FIGS. 16 and 17, wherein the cartridge 300 is similar to the embodiment of the cartridge 250 as depicted in FIGS. 14 and 15. The cartridge 300 includes a frame 302 and a refill 304, wherein the frame 302 includes a base portion 306 with first and second posts 308a, 308b extending from a top surface 310 of the base portion 306. One or more of the posts 308a, 308b includes a tab 311 extending therefrom, wherein the tab 311 is adapted to snap into a detent in an active material emitting device to aid in securing the cartridge 300 within the device. Preferably, a connecting post 312 is integral with and extends between the posts 308a, 308b near a top portion thereof, thereby forming an aperture 313 in the frame 302 defined by the posts 308a, 308b and the connecting post 312. A handle 314 extends from a bottom surface 316 of the base portion 306, wherein the handle 314 may be grasped by a user to guide the cartridge 300. The refill 304 is similar to the refill 254 of the embodiment of FIGS. 14 and 15 and includes first and second reservoirs 320a, 320b having active materials therein, wherein each reservoir 320a, 320b includes a lip portion 321a, 321b surrounding the respective reservoir 320a, 320b. The lip portions 321a, 321b are joined to one another at top portions 322a, 332b thereof by a connecting portion 324. Each of the reservoirs 320a, 320b includes a bottom surface 326a, 326b and a top surface 328a, 328b, respectively. The bottom surfaces 326a, 326b are preferably, although not necessarily, spaced slightly from one another when the cartridge 300 is assembled. As in previous embodiments, each of the top surfaces 328a, 328b includes a non-removable vapor permeable sealing layer 330a, 330b and a removable vapor impermeable layer 332a, 332b disposed atop the vapor permeable sealing layer 330a, 330b, respectively.

Referring to FIG. 16, the cartridge 300 is assembled by inserting the connecting portion 324 of the refill 304 over the connecting post 312 of the frame 302 and positioning the reservoirs 320a, 320b in the aperture 313 such that the bottom surfaces 326a, 326b of the reservoirs 320a, 320b, respectively, are in contact with one another or are spaced slightly from one another. Preferably, the lip portions 321a, 321b, abut the posts 308a, 308b. Also preferably, the lip portions 334a, 334b are joined to the posts 308a, 308b by heat-staked posts 336a, 336b adjacent the base portion 306, or optionally may be joined by any other means known in the art, including welding, press-fitting, adhesives, or combinations thereof. Still further, when assembled, one or more of the posts 308a, 308b preferably extends beyond the connecting portion 324 of the refill 304. Also preferably, although not necessarily, the cartridge 300 is assembled during manufacture thereof.

The cartridge 300 of FIGS. 16 and 17 may be grasped by the handle 314 and inserted into an appropriately shaped recess in an active material emitting device such as the device 100 of FIGS. 1-7. Preferably, the cartridge 300 is inserted through a bottom portion of the device 100, but may also be inserted through a top or side portion thereof. As the cartridge 300 is inserted into the device 100, the one or more posts 308a, 308b extending beyond the connecting portion 324 may actuate an actuator arm 337 of a switch 338 to indicate that a cartridge 300 has been inserted into the device 100.

As seen in FIGS. 18 and 19, a fourth embodiment of an active material cartridge 350 is depicted. The cartridge 350 includes a base portion 352 having a frame 354 extending upwardly therefrom. The frame 354 includes first and second reservoirs 356a, 356b of active material disposed within the frame 354 on first and second sides 357a, 357b thereof. The reservoirs 356a, 356b are similar to the reservoirs 216a, 216b as described in detail with respect to the embodiment of FIGS. 8-13. The frame 354 further includes a cylindrical post 358 extending through the frame 354 from the base portion 352 to a top portion 360 of the frame 354. A projection 362 is integral with a first end 363 of the cylindrical post 358 and is disposed atop the top portion 360 of the frame 354. A rotating tab 364 is integral with a second end 366 of the cylindrical post 358 and extends from a bottom surface 368 of the base portion 352. Optionally, as in any of the embodiments disclosed herein, the cartridge 350 of FIGS. 18 and 19 may only include a single reservoir 356a, 356b with active material therein.

The cartridge 350 of FIGS. 18 and 19, when in use, may be inserted into an appropriately shaped recess in an active material emitting device such as the device 100 of FIGS. 1-7. Once the cartridge 350 is inserted into the device 100, the tab 364 may be rotated in the direction of an arrow 369 (FIG. 18), thereby rotating the cylindrical post 358 and projection 362. As the projection 362 and a slot 370 disposed in a portion of the projection 362 rotate, walls defining the slot 370 engage a wall 372 or other structure of an active material emitting device 100, thereby locking the cartridge 350 in position. Thereafter, when it is desired to remove the cartridge 350 from the device 100, the tab 364 is counter-rotated opposite to the direction of the arrow 369 to cause the walls defining the slot 370 to move out of engagement with the structure of the device 100, thereby permitting withdrawal of the cartridge 350 from the device 100. Optionally, the tab 364 may originally be rotated in a direction opposite the arrow 369 to lock the cartridge 350 in position.

The present invention may comprise a fifth embodiment of an active material cartridge 400 as represented in FIGS. 20, 20A, 20B, and 21. The cartridge 400 includes a frame 402 with first and second opposing side portions 404a, 404b, a top portion 406, and a bottom portion 408. First and/or second reservoirs 410a, 410b having active materials therein may be disposed in a front portion 412 and/or a back portion 414 of the cartridge 400. The reservoirs 410a, 410b are similar to the reservoirs 216a, 216b as described in detail with respect to the embodiment of FIGS. 8-13. Preferably, the cartridge 400 includes first and second flexible fingers 416a, 416b disposed in the side portions 404a, 404b, respectively, thereof. Also preferably, a protrusion 418 extends from the top portion 406 of the cartridge 400.

As seen in FIGS. 20A and 21, the cartridge 400 may be utilized in combination with an active material emitting device 420. The active material device 420 comprises a base portion 422 having a body portion 424 integral therewith and extending upwardly therefrom. Preferably, the body portion 424 (or any other component of the device 420) includes first and second tabs 426a, 426b extending outwardly therefrom. A top wall 428 (or any other component of the device 420) also preferably includes a switch 429 having an actuator arm 430 extending downwardly therefrom. Before insertion of the cartridge 400 into the device 420, metal foil sections 431a, 431b are removed from the reservoir(s) 216a, 216b (as seen in FIG. 20A) so that active material can be emitted therefrom. Thereafter, the cartridge 400 is inserted into the device 420 through an appropriately sized aperture 432 in the base portion 422. As the cartridge 400 is inserted, the tabs 426a, 426b extending from the body portion 424 of the device 420 engage the flexible fingers 416a, 416b, respectively, whereby the flexible fingers 416a, 416b flex inwardly about hinges 433a, 433b thereby to retain the cartridge 400 in the device 420. Further, as the cartridge 400 is inserted, the protrusion 418 extending from the top portion 406 of the cartridge 400 depresses the actuator arm 430, thereby indicating to the device 420 that a cartridge 400 has been inserted therein.

Figure 24:
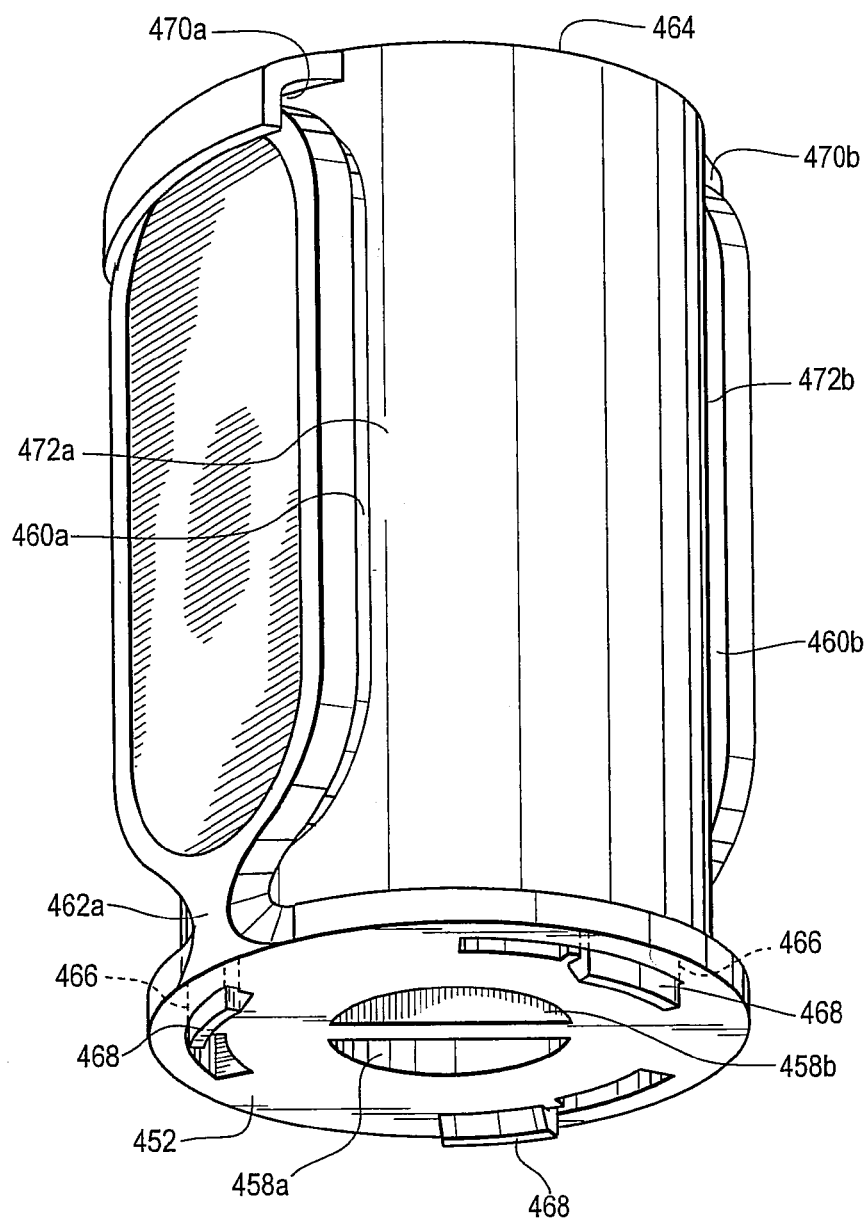
FIG. 24 a bottom isometric view of an active material emitting device assembled with the cartridge of FIG. 22.

A sixth embodiment of an active material cartridge 450 is illustrated in FIGS. 22-24. The active material cartridge 450 includes a circular central base portion 452 with slotted apertures 454. Each slotted aperture 454 accommodates a bayonet-type connection and preferably comprises a narrower portion 454a and a wider portion 454b, wherein the apertures 454 are spaced from one another adjacent an edge 456 of the base portion 452. The base portion 452 further includes two vent holes 458a, 458b disposed in a center 459 thereof. First and second lip portions 460a, 460b surrounding first and second reservoirs 461a, 461b having active materials therein are joined to the base portion 452 by first and second connecting portions 462a, 462b, respectively. The reservoirs 460a, 460b are similar or identical to the reservoirs 216a, 216b as described in detail with respect to the embodiment of FIGS. 8-13.

The cartridge 450 of FIGS. 22-24 is used in conjunction with an active material emitting device 464 having any number of downwardly-extending legs 466 having radially outwardly-extending feet 468. The device 464 further includes first and second slots 470a, 470b on first and second sides 472a, 472b, respectively thereof. When the cartridge 450 is inserted into the device 464, the legs 466 and feet 468 are inserted through the wider portions 454b of the apertures 454 and the device 464 and cartridge 450 are rotated relative to one another (as described in detail with respect to FIGS. 1-7), thereby securing the device 464 to the cartridge 450. As the legs 466 and feet 468 engage the base portion 452, the reservoirs 460a, 460b are inserted into the slots 470a, 470b (FIG. 24) to secure the reservoirs 460a, 460b in position. Although slots 470a, 470b are shown as securing the reservoirs 460a, 460b to the device 464, any securing means may be utilized.

An active material cartridge 500 of a seventh embodiment is depicted in FIGS. 25-27. The active material cartridge 500 includes a circular central vent portion 502 with a central aperture 504 therethrough and any number of vent holes 506 disposed therearound. The vent holes 506 may be of any shape or size and may be disposed at any location(s) within the vent portion 502. First and second lip portions 507a, 507b surrounding first and second reservoirs 508a, 508b having active material therein are connected to opposite sides 510a, 510b of the vent portion 502, wherein the connections between the reservoirs 508a, 508b and the sides 510a, 510b of the vent portion 502 are flexible. The reservoirs 508a, 508b are similar or identical to the reservoirs 216a, 216b as described in detail with respect to the embodiment of FIGS. 8-13.

As seen in FIG. 27, the cartridge 500 may be inserted into an active material emitting device 512 having first and second slots 513a, 513b on first and second sides 514a, 514b, respectively, thereof. The device 512 also preferably includes a light emitter 515 at a top portion 516 thereof. When the cartridge 500 is inserted into the device 512, the cartridge 500 is flexed at the connection between the lip portions 507a, 507b and the sides 510a, 510b of the vent portion 502. Thereafter, the reservoirs 508a, 508b are inserted into the slots 513a, 513b such that the vent portion 502 abuts the top portion 516 of the device 512 and the light emitter 515 extends through the central aperture 504. The vent holes 506 in the cartridge 500 are preferably aligned with vent holes in the top portion 516 to allow active material emissions to be circulated throughout the device 512. Although slots 513a, 513b are depicted for retaining the reservoirs 508a, 508b in the device 512, any means for retaining the reservoirs 508a, 508b in the device 512 may be utilized.

Figure 28:
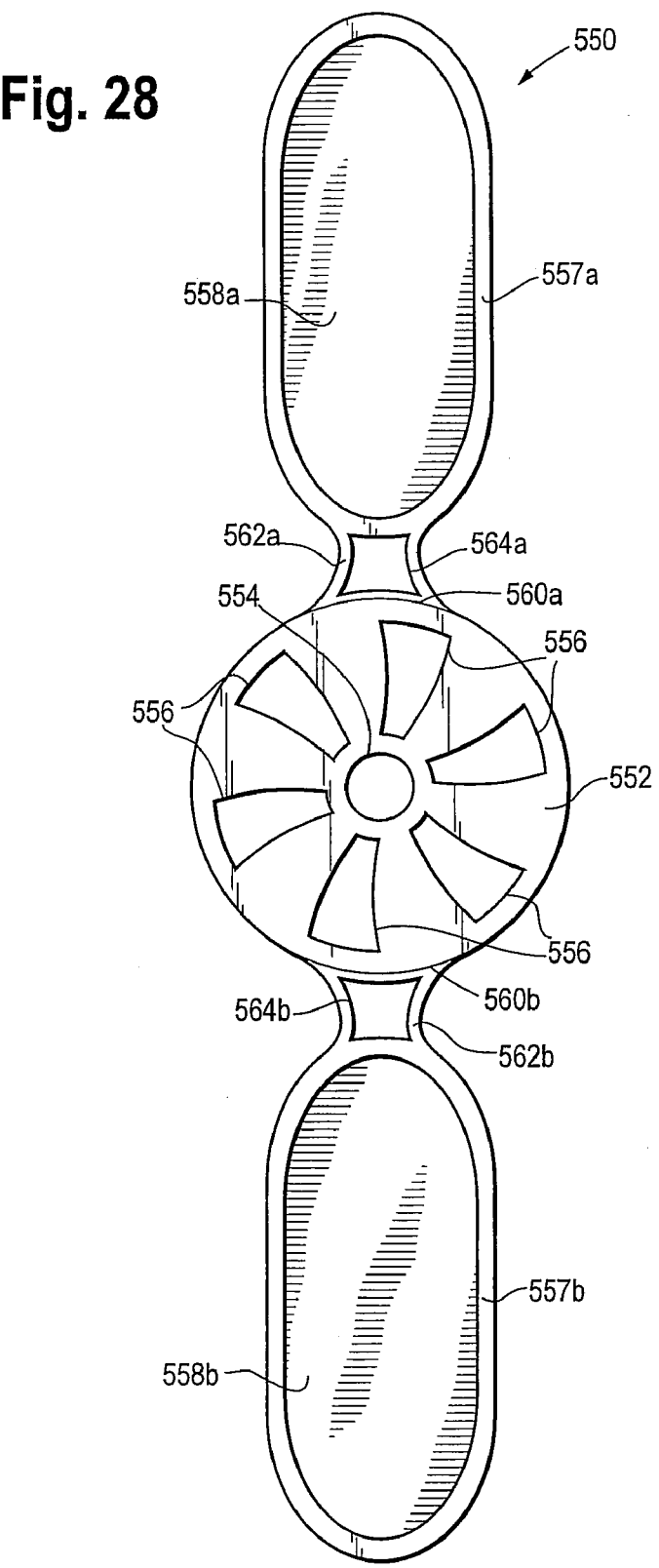
FIG. 28 is a plan view of an eighth embodiment of an active material cartridge.

The present invention may comprise an eighth embodiment of an active material cartridge 550 as illustrated in FIG. 28, which is similar to the cartridge 500 of FIGS. 25-27. The active material cartridge 550 includes a circular central vent portion 552 with a central aperture 554 therethrough and any number of vent holes 556 disposed therearound. The vent holes 556 may be any size or shape and may be disposed at any suitable location within the vent portion 552. First and second lip portions 557a, 557b surrounding first and second reservoirs 558a, 558b having active material therein are connected to opposite sides 560a, 560b of the vent portion 552 by flexible connecting portions 562a, 562b, respectively. Preferably, although not necessarily, the connecting portions 562a, 562b also have one or more vent holes 564a, 564b therethrough. The reservoirs 558a, 558b are similar to the reservoirs 216a, 216b as described in detail with respect to the embodiment of FIGS. 8-13. The active material cartridge 550 is preferably inserted into the active material emitting device 512 as shown and described with respect to FIG. 27.

Figure 29:
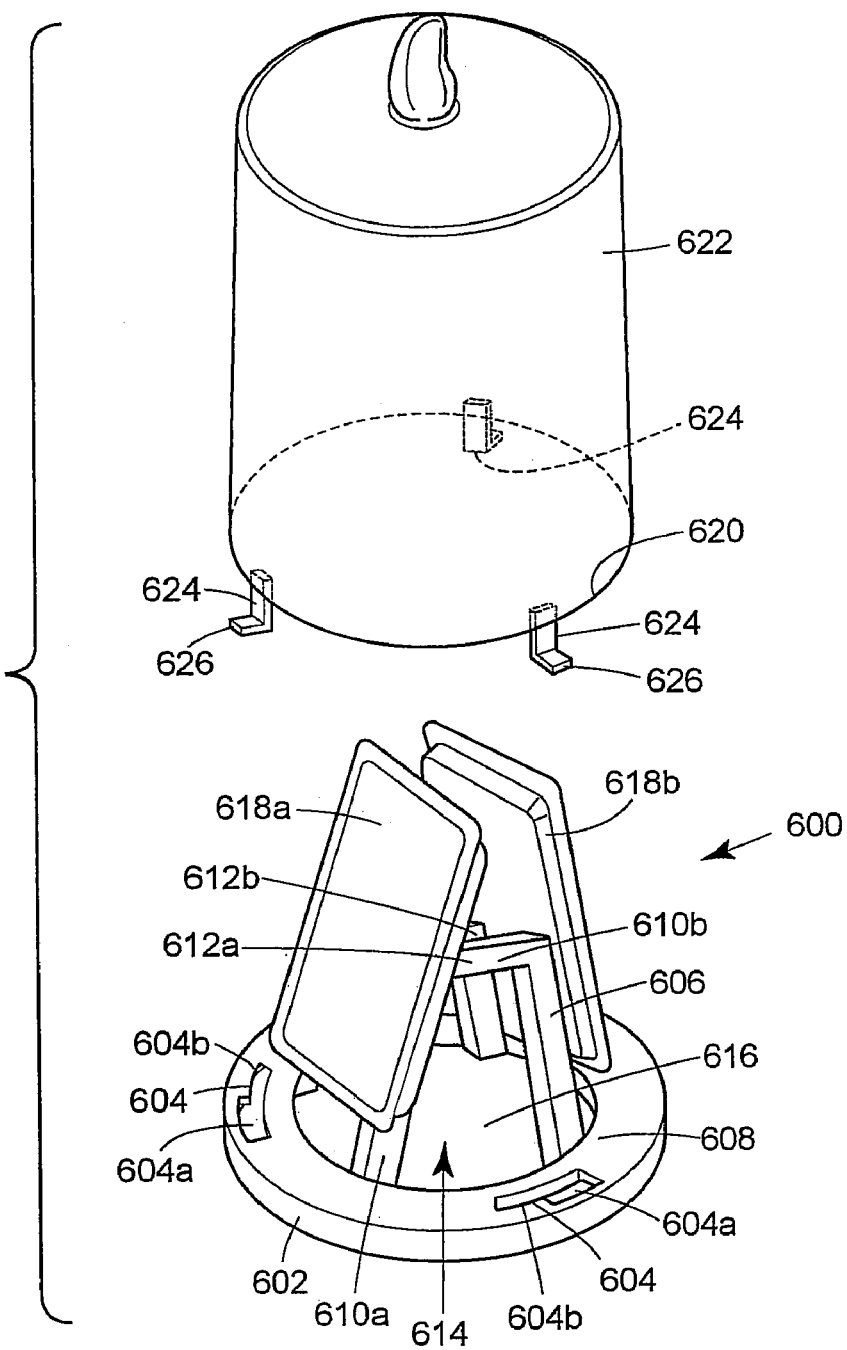
FIG. 29 is a top isometric view of a ninth embodiment of an active material cartridge.

FIG. 29 depicts a ninth embodiment of an active material cartridge 600, wherein the cartridge 600 includes a base portion 602 having one or more curved slots 604. Each slot 604 accommodates a bayonet-type connection and preferably comprises a wider portion 604a and a narrower portion 604b. The base portion 602 also includes a support structure 606 extending from a top surface 608 thereof. The support structure 606 includes first and second angled side portions 610a, 610b with one or more connecting portions 612a, 612b that join the side portions 610a, 610b. Preferably, the support structure 606 is situated atop the base portion 602 such that an air pathway 614 extends through a central portion 616 of the cartridge 600. The cartridge 600 further includes first and second reservoirs 618a, 618b having active material therein and as described in detail with respect to the embodiment of FIGS. 8-13, wherein the reservoirs 618a, 618b are attached to the first and second side portions 610a, 610b. The reservoirs 618a, 618b may be attached to the side portions 610a, 610b in any known manner.

As further seen in FIG. 29, the cartridge 600 is preferably inserted through a bottom portion 620 of an active material emitting device 622. The device 622 preferably includes two or more downwardly-extending legs 624 extending from the bottom portion 620 thereof, wherein the legs 624 include radially outwardly-extending feet 626. As the cartridge 600 is inserted into the bottom portion 620, the legs 624 and feet 626 are inserted through the wider portions 604a of the slots 604 and the device 622 and the cartridge 600 are rotated relative to one another (as described in detail with respect to the device of FIGS. 1-7), thereby securing the cartridge 600 in the device 622. Optionally, the device 622 may include any number of vent holes therein to circulate volatilized active material.

Figure 30:
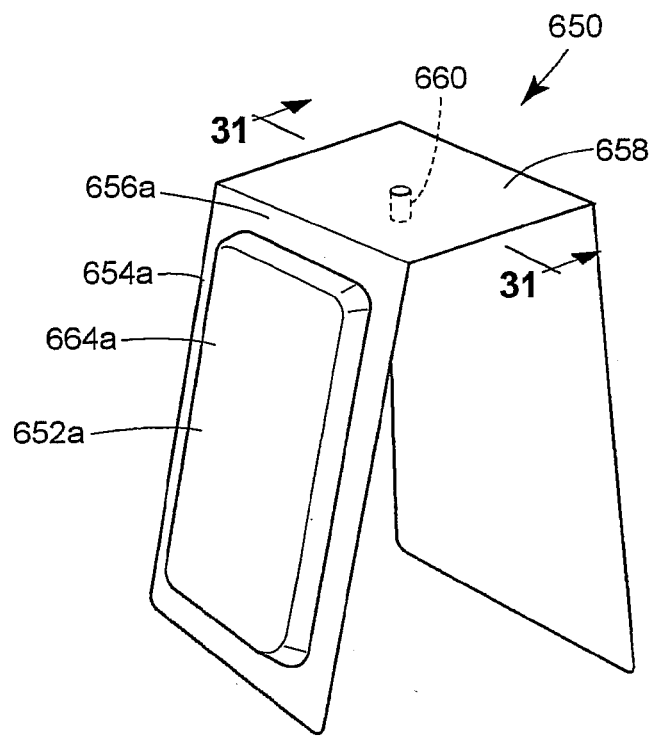
FIG. 30 is a top isometric view of a tenth embodiment of an active material cartridge.
Figure 31:
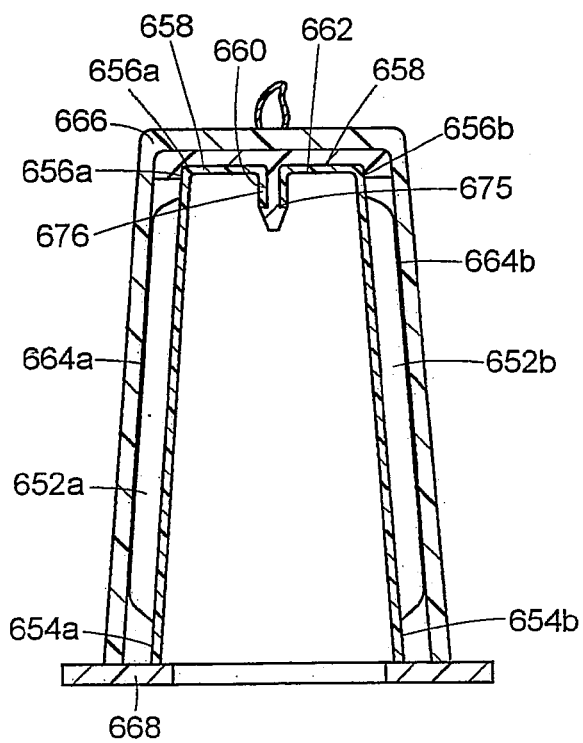
FIG. 31 is cross-sectional view taken generally along the lines 31-31 of FIG. 30, illustrating the cartridge of FIG. 30 inserted into an active material emitting device.

The present invention may comprise a tenth embodiment of a cartridge 650 as represented in FIGS. 30 and 31. The cartridge 650 includes first and second reservoirs 652a, 652b having active materials therein, wherein each of the reservoirs 652a, 652b includes a lip portion 654a, 654b surrounding the respective reservoir 652a, 652b. The reservoirs are similar or identical to the reservoirs 216a, 216b as described in detail with respect to the embodiment of FIGS. 8-13. The lip portions 654a, 654b are connected at top portions 656a, 656b thereof by a connecting portion 658. The connecting portion 658 includes a flexible downwardly projecting collar 660 extending from a lower surface 662 thereof. Although the reservoirs 652a, 652b are depicted as having bottom surfaces 664a, 664b that face away from one another, the cartridge 650 may be modified such that the bottom surfaces 664a, 664b may optionally face toward one another.

The cartridge 650 may be inserted into an active material emitting device 666, as seen in FIG. 31. The device 666 generally includes a base portion 668 having first and second upstanding walls 670a, 670b and a top wall 672 connecting the upstanding walls 670a, 670b. A barb element 674 is attached to and extends from the top wall 672. Although the barb element 674 is depicted as an element separate from the top wall 672 of the device 666, the barb element 674 may also be integral with and extend downwardly directly from the top wall 672. The cartridge 650 is inserted into the device 666 through an aperture 673 in the base portion 668 by grasping the lip portions 654a, 654b, pressing them together, and inserting the connecting portion 658 through the aperture far enough so that the barb element 674 extends into the collar 660 of the connecting portion 658 and a shoulder 675 of the barb element 674 is engaged by a lower lip 676 of the collar 660, thereby retaining the cartridge 650 in the device 666. Thereafter, the lip portions 654a, 654b may be released so the lip portions 654 may flex outwardly against the walls 670a, 670b of the device 666. As should be apparent, the aperture 673 need only be large enough to accommodate the connecting portion 658 of the cartridge 650. A user may remove the cartridge 650 from the device 666 by grasping the lip portions 654a, 654b of the cartridge 650, moving same toward one another, and pulling the cartridge 650 downwardly to overcome the engagement of the barb element 674 with the collar 660 so that the cartridge 650 can be moved downwardly and out through the aperture 673.

Figure 32:
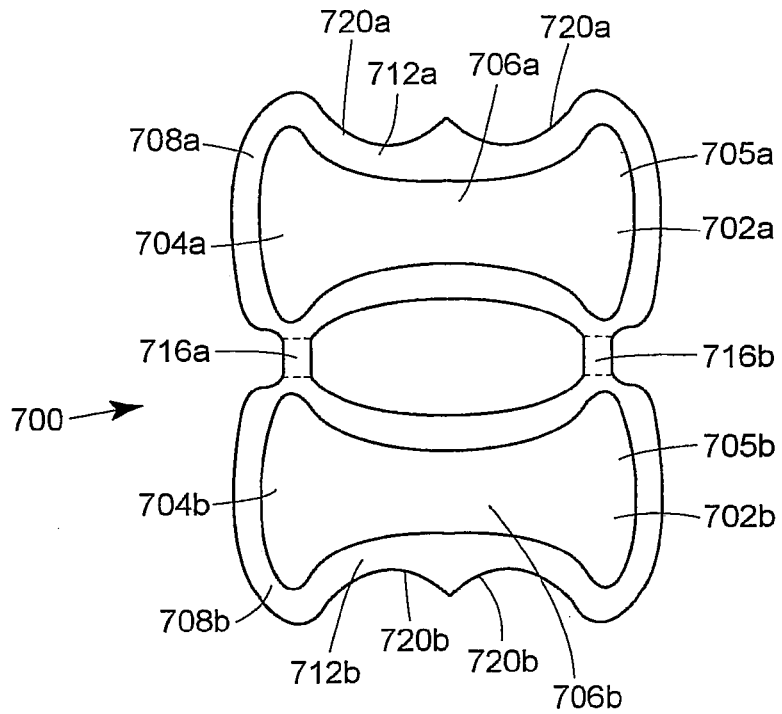
FIG. 32 is a top plan view of an eleventh embodiment of an active material cartridge in an unfolded position.
Figure 33:
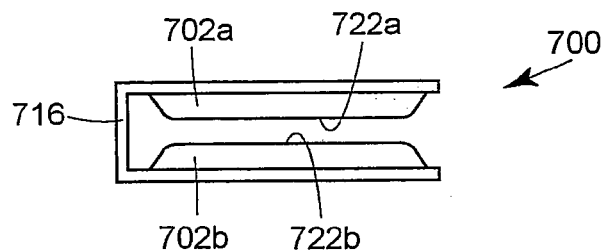
FIG. 33 is a side view of the cartridge of FIG. 32 in a folded position.
Figure 33A:
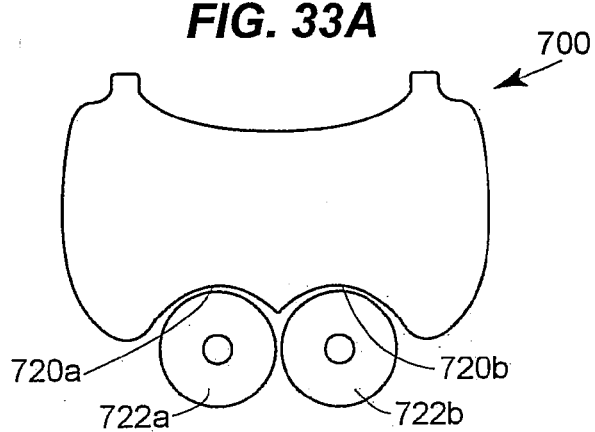
FIG. 33A is a plan view of the cartridge of FIG. 33 surrounding batteries.

As seen in FIGS. 32, 33, and 33A, an eleventh embodiment of a cartridge 700 is depicted, wherein the cartridge 700 includes first and second reservoirs 702a, 702b having active material therein. Each reservoir 702a, 702b includes a first relatively wide section 704a, 704b and a second relatively wide section 705a, 705b of active material connected by a relatively narrow section 706a, 706b of active material. Further, each reservoir 702a, 702b is surrounded by a lip portion 708a, 708b, respectively, wherein the each lip portion 708a, 708b includes a first side 710a, 710b and a second side 712a, 712b opposite the first side 710a, 710b. Flexible connecting portions 716a, 716b preferably connect the first sides 710a, 710b of the lip portions. Optionally, a single connecting portion spanning the first sides 710a, 710b or more than two connecting portions may be utilized. Preferably, although not necessarily, the second sides 712a, 712b of each of the lip portions 708a, 708b include two curved cut-out portions 720a, 720b. The cartridge 700 may be inserted into an active material emitting device by folding the first and second reservoirs 702a, 702b toward one another and about the connecting portions 716a, 716b, as seen in FIG. 33, such that bottom surfaces 722a, 722b of the reservoirs 702a, 702b are in contact with or are slightly spaced from one another. Thereafter, the cartridge 700 may be inserted into the appropriate device, wherein the cut-out portions 720a, 720b may surround batteries 722a, 722b for powering the device, as seen in FIG. 33A.

Figure 34:
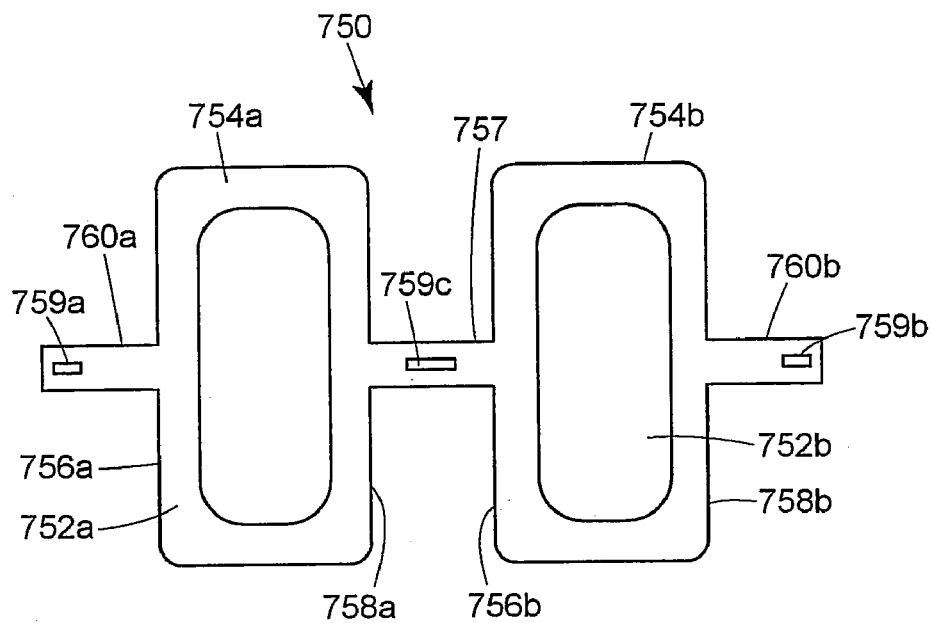
FIG. 34 is a plan view of a twelfth embodiment of an active material cartridge.
Figure 35:
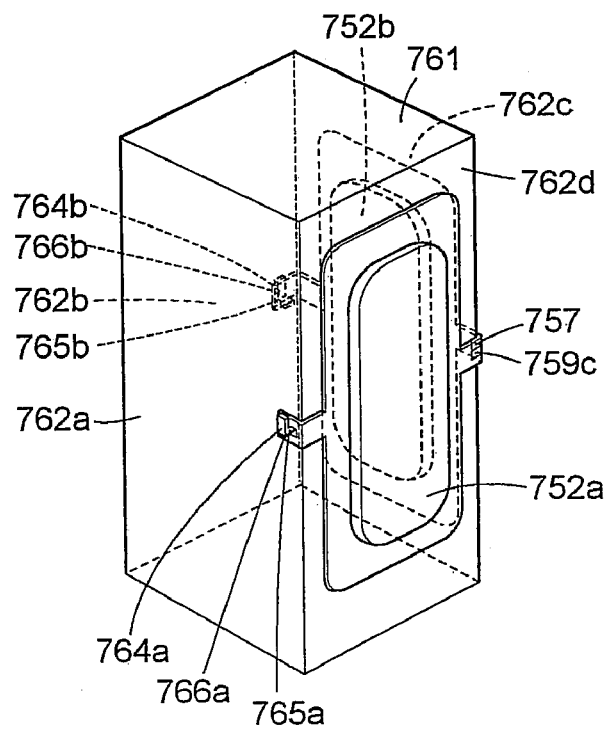
FIG. 35 is a top isometric view of the cartridge of FIG. 34 attached to an active material emitting device.

The present invention may comprise a twelfth embodiment of a cartridge 750 as depicted in FIGS. 34 and 35. The cartridge 750 includes first and second reservoirs 752a, 752b each having active material therein, wherein the reservoirs 752a, 752b include first and second lip portions 754a, 754b surrounding the respective reservoir 752a, 752b. Each of the first and second lip portions 754a, 754b includes a first side 756a, 756b and a second opposing side 758a, 758b, wherein the second side 758a of the first lip portion 754a is connected to the first side 756b of the second lip portion 754b by a connecting portion 757. Additionally, a first attachment portion 760a extends from the first side 756a of the first lip portion 754a and includes a first aperture 759a therethrough and a second attachment portion 760b extends from the second side 758b of the second lip portion 754b and includes a second aperture 759b therethrough. Optionally, a third aperture 759c may be disposed in the connecting portion 756.

Preferably, the cartridge 750 is attached to an active material emitting device 761, as seen in FIG. 35. The device 761 preferably includes first, second, third, and fourth side wall panels 762a-762d, wherein each of the first and second wall panels 762a, 762b includes an anchor 764a, 764b, respectively, extending therefrom. Each of the anchors 764a, 764b includes a first portion 765a, 765b normal to the respective wall panels 762a, 762b and a second portion 766a, 766b perpendicular to and extending upwardly from the respective first portion 765a, 765b. Optionally, any anchors 764 known in the art may be utilized.

In use, the cartridge 750 is attached to the device 761 by positioning the cartridge such that one of the anchors 764a, 764b extends through a respective aperture 759a, 759b, wrapping the reservoirs 752a, 752b around the third and fourth wall panels 762c, 762d, and latching the other of the apertures 759a, 759b onto the respective anchor 764a, 764b to secure the cartridge 750 on the device 761. Optionally, one or more additional anchors 764 may be disposed on the third and/or fourth wall panels 762c, 762d for securing the third aperture 759c thereon. Although the embodiment of FIGS. 34 and 35 includes two reservoirs 752a, 752b with active materials therein, such an embodiment may utilize any number of reservoirs 752.

Figure 36:
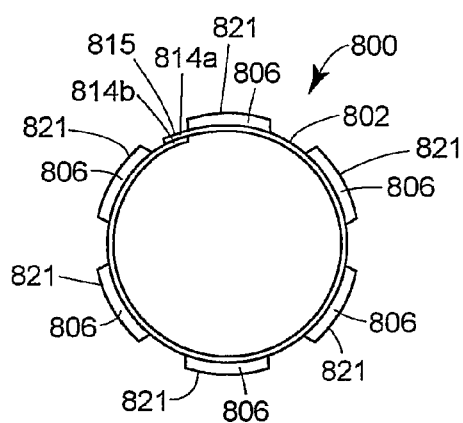
FIG. 36 is a plan view of a thirteenth embodiment of an active material cartridge.
Figure 37:
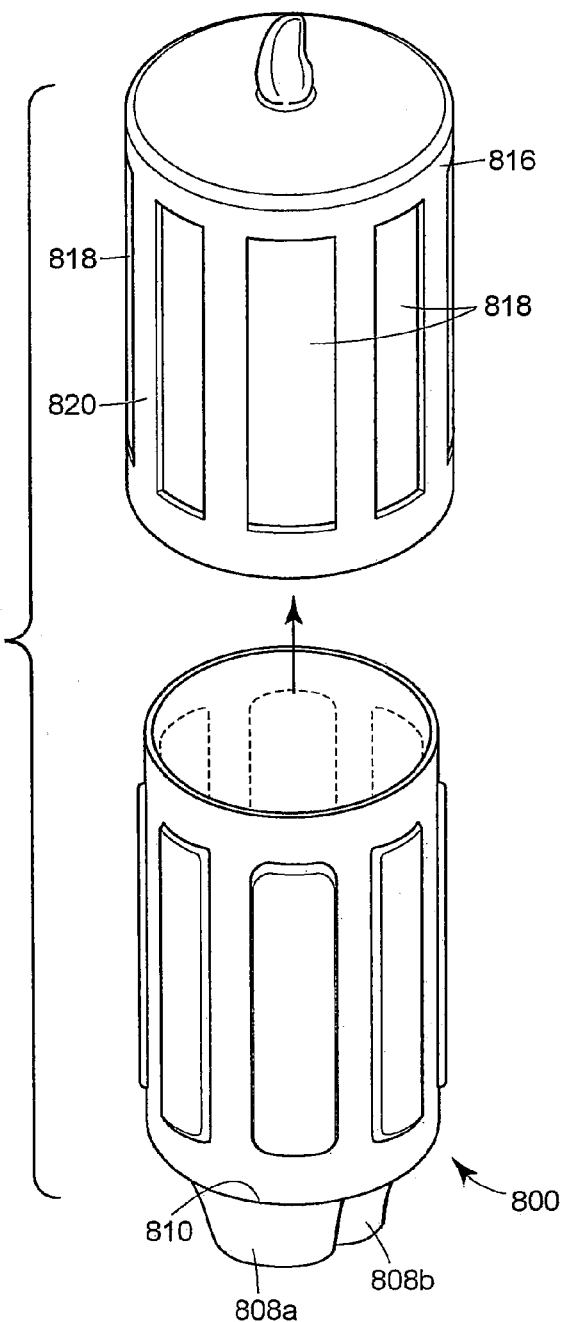
FIG. 37 is a top isometric view of the cartridge of FIG. 36 illustrating insertion of the cartridge into an active material emitting device.

A thirteenth embodiment of an active material cartridge 800 is illustrated in FIGS. 36 and 37, wherein the cartridge 800 includes a hollow cylindrical base portion 802. The base portion 802 includes one or more reservoirs 806 having an active material therein, wherein the reservoirs 806 are spaced around and integral with or separate from the base portion 802. The reservoirs 806 are similar or identical to the reservoirs 216a, 216b as described in detail with respect to the embodiment of FIGS. 8-13. First and second tabs 808a, 808b extend from a bottom portion 810 of the base portion 802. The base portion 802 may be continuous or may be discontinuous, wherein if the base portion 802 is discontinuous, at least first and second edges 814a, 814b of the base portion 802 may be welded or otherwise joined by suitable means as described hereinabove at a portion 815. If the base portion 802 includes two or more sections or portions, edges of the sections or portions may be welded or secured together by any suitable means as described hereinabove.

The cartridge 800 may be used in conjunction with an active material emitting device 816 as seen in FIG. 36. The device 816 optionally includes longitudinal vent holes 818 spaced around a periphery 820 thereof, wherein a number of vent holes 818 preferably (although not necessarily) is the same as a number of reservoirs 806. In one variant the cartridge 800 may be inserted over the device 816 such that the reservoirs 806 are aligned with the vent holes 818 with sufficient space therebetween to allow air flow through the device 816. In another variant, as seen in FIG. 37, the cartridge 800 may be inserted within the device 816 such that the reservoirs 806 extend from an inside of the device 816 through the vent holes 818, thus creating an interference between outer surfaces 821 of the reservoirs 806 and walls defining the vent holes 818. In either case, the cartridge 800 may be grasped by the first and second tabs 808a, 808b to aid in attaching the cartridge 800 to the device 816.

Figure 38:
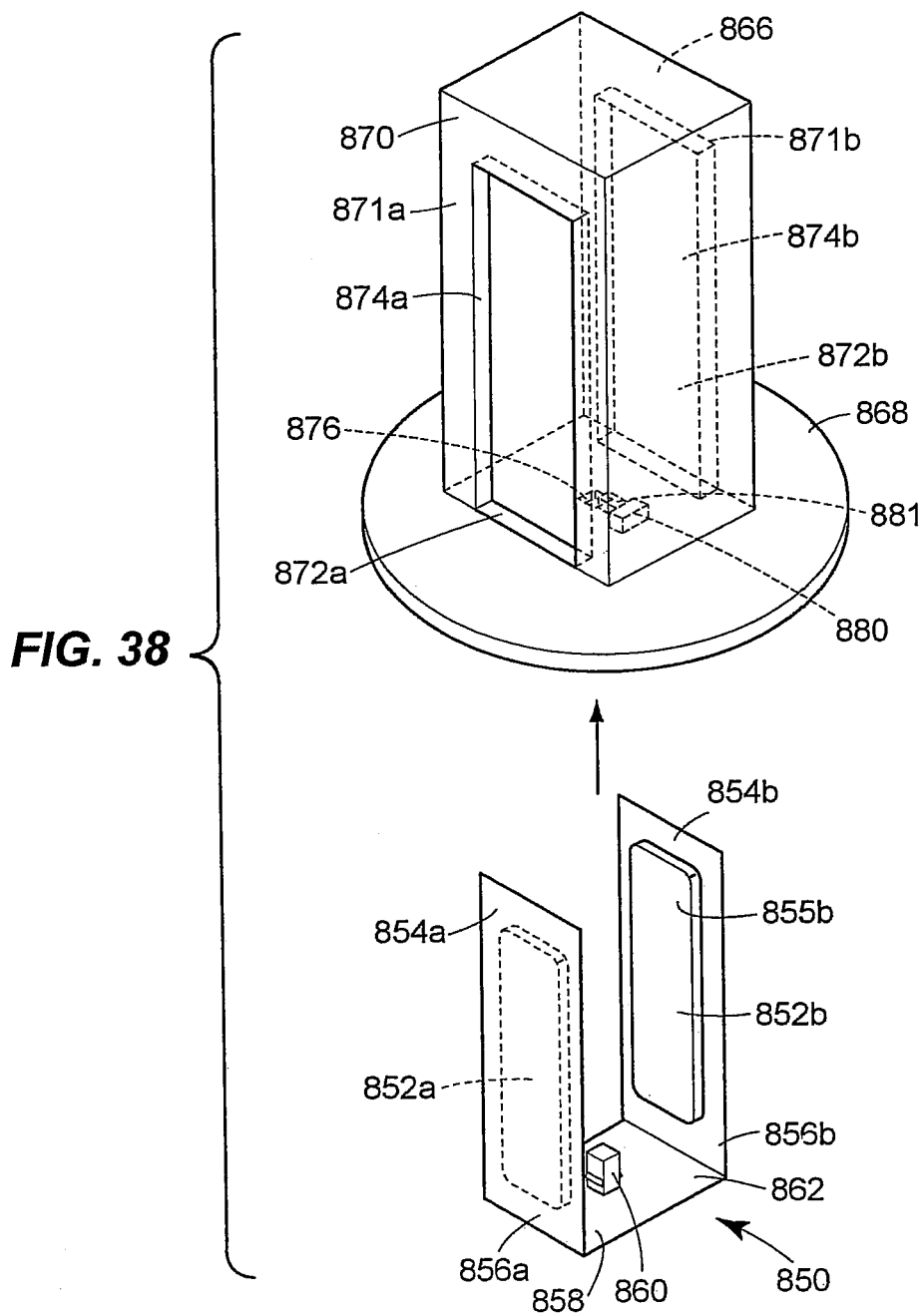
FIG. 38 is a top isometric view of a fourteenth embodiment of an active material cartridge illustrating insertion of the cartridge into an active material emitting device.
Figure 39:
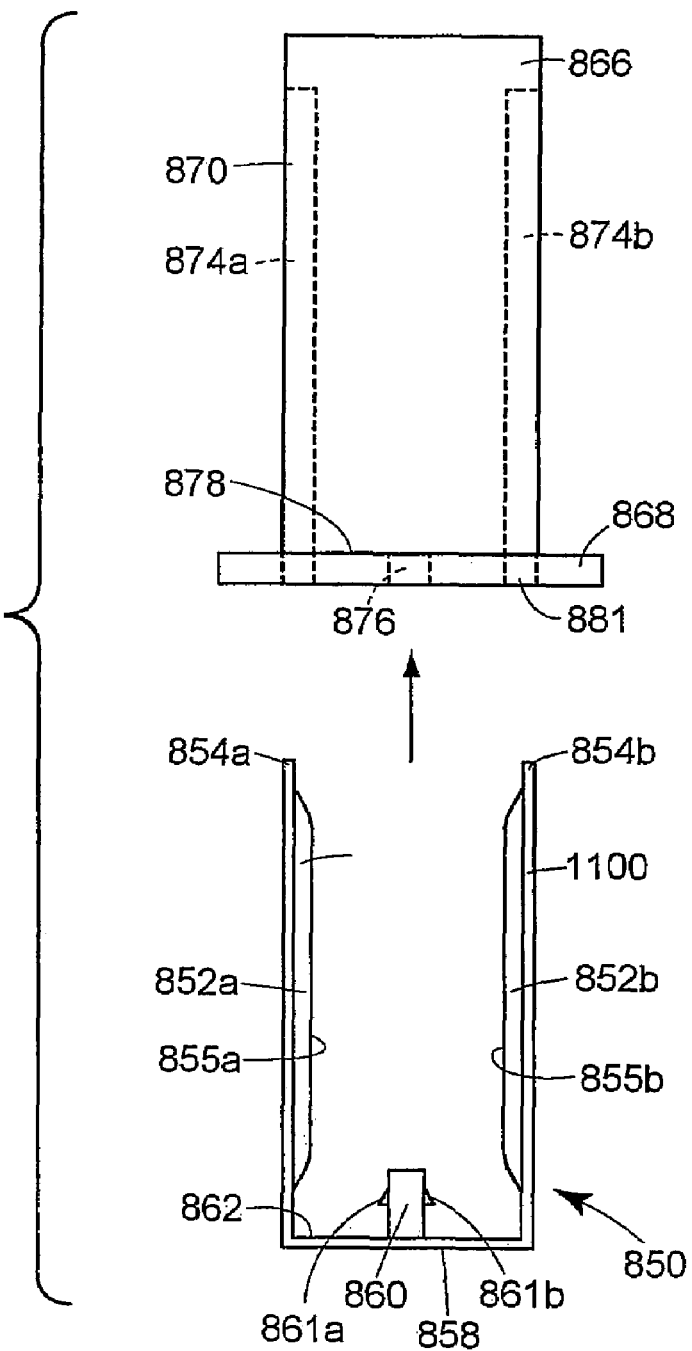
FIG. 39 is a front elevational view of FIG. 38.

An active material cartridge 850 of a fourteenth embodiment is depicted in FIGS. 38 and 39. The active material cartridge 850 includes first and second reservoirs 852a, 852b having active materials therein, wherein each of the reservoirs 852a, 852b includes a lip portion 854a, 854b surrounding the respective reservoir 852a, 852b. The reservoirs 852a, 852b are similar or identical to the reservoirs 216a, 216b as described in detail with respect to the embodiment of FIGS. 8-13. Preferably, although not necessarily, the reservoirs 852a, 852b have inner surfaces 855a, 855b that are directed toward one another. The lip portions 854a, 854b are connected at bottom portions 856a, 856b thereof by a connecting portion 858. Optionally, the connecting portion 858 may include at least one upstanding projection 860 extending from a top surface 862 of the connecting portion 858, wherein each projection 860 includes outwardly extending shoulders 861a, 861b extending from opposite sides thereof.

The cartridge 850 may be inserted into an active material emitting device 866, wherein the device 866 includes a base portion 868 and a body portion 870 integral with and extending upwardly from the base portion 868. The device 866 preferably includes a first aperture 872a in the base portion 868 and a slot 874a disposed in the body portion 870 adjacent the aperture 872a wherein the aperture 872a and the slot 874a are disposed on a first side 871a of the device 866. An aperture 872b and slot 874b identical to the aperture 872a and slot 874a are disposed on a second side 871b of the device 866. The cartridge 850 is inserted into the device 866 such that the reservoirs 852a, 852b are inserted through the respective apertures 872a, 872b and into the respective slots 874a, 874b. As the cartridge 850 is inserted into the device 866, the projection 860 is inserted through an aperture 876 in the base portion 868, and the shoulders 861a, 861b interfere with a top surface 878 of the base portion 868 to retain the cartridge 850 therein. Optionally, if desired, other interferences may be utilized to retain the cartridge 850 within the device 866 in addition to or in place of the shoulders 861a, 861b.

In the case where the cartridge 850 includes a projection 860, a switch 880 with an actuator arm 881 (FIG. 38) may be disposed within the device 866, preferably attached to the top surface 878 of the base portion 868. When the actuator arm 881 is moved by the projection 860, the device 868 may turn on or perform any function.

Figure 40:
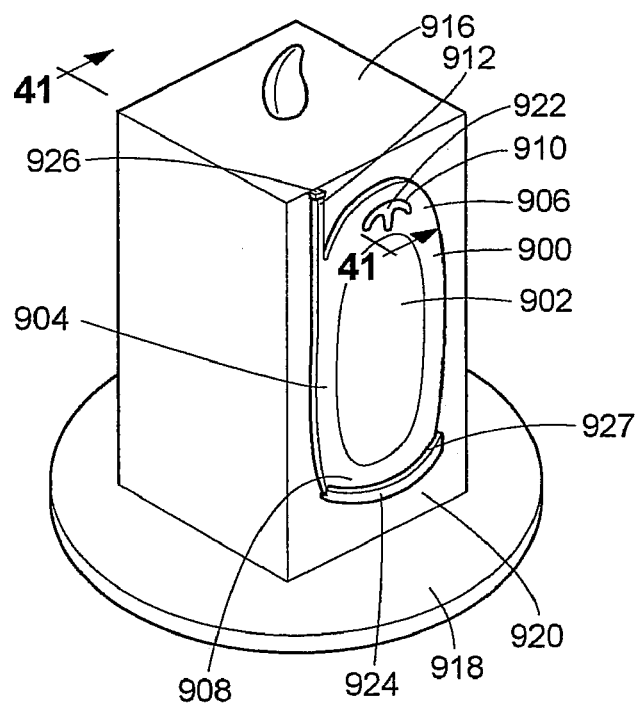
FIG. 40 is a top isometric view of a fifteenth embodiment of an active material cartridge disposed on an active material emitting device.
Figure 41:
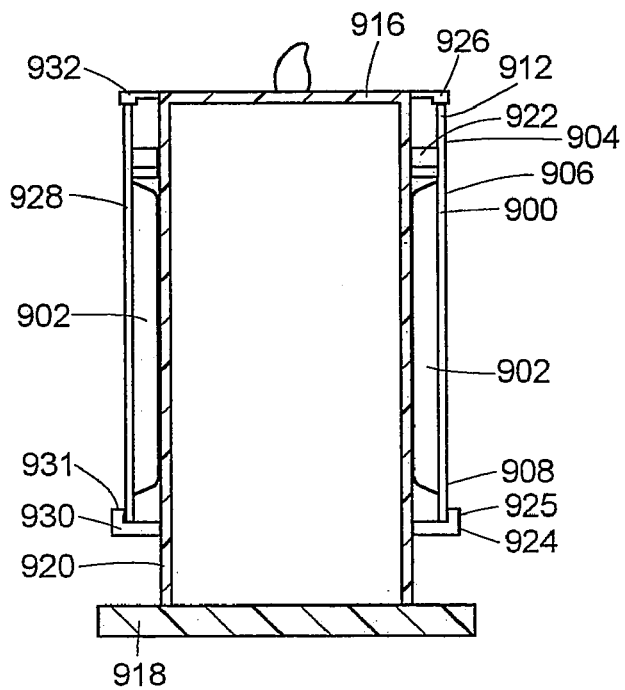
FIG. 41 is a cross-sectional view taken generally along the lines 41-41 of FIG. 40 illustrating a dual cartridge device.

The present invention may comprise a fifteenth embodiment of an active material cartridge 900 as shown in FIGS. 40 and 41. The cartridge 900 includes a reservoir 902 having an active material therein, wherein the reservoir 902 includes a lip portion 904 surrounding the reservoir 902. The lip portion 904 has a top portion 906 and a bottom portion 908, wherein in the illustrated embodiment the top portion 906 includes a generally T-shaped aperture 910 therein. It should be noted that the aperture 910 may alternatively have any shape or size. The top portion 906 may also include an actuator portion in the form of a projection 912 extending outwardly from the lip portion 904.

The cartridge 900 may be positioned on an active material emitting device 916, wherein the device 916 includes a base portion 918 and a body portion 920 integral with and extending upwardly from the base portion 918. The body portion 920 includes a first protrusion 922 having a shape that is complementary to the shape of at least a portion of the aperture 910 and a ledge 924 with an upwardly projecting lip 925. Preferably, the ledge 924 has a shape complementary to the shape of a bottom edge 927 of the lip portion 904 of the cartridge 900. The cartridge 900 is positioned such that the bottom portion 908 of the lip portion 904 rests atop the ledge 924 behind the lip 925 and, thereafter, the cartridge 900 is pivoted toward the device 916 until walls defining at least a portion of the aperture 910 engage and are secured in position by the first protrusion 922. The device 916 may also include a switch having an actuator arm 926 extending therefrom, wherein as the walls defining the aperture 910 engage the first protrusion 922, the projection 912 cams the switch 926 upwardly, thereby indicating a cartridge 900 is disposed on the device 916 and/or triggering some other action. As seen in FIG. 41, the device 916 may further include a third protrusion 928 similar to the first protrusion 922, a second ledge 930 having an upward projecting lip 931 similar to the ledge 924, and a second switch with an actuator arm 932, to accommodate an optional second cartridge 932 that is similar to the cartridge 900. In such an embodiment, the device 916 may not function and/or an action may not be triggered unless both switches 926, 932 are actuated or may function and/or trigger an action when only one switch is actuated. Optionally, no matter how many cartridges 900 are utilized, the device 916 may only include a single switch and arm actuable by a projection of a cartridge.

Although FIG. 41 is depicted as having two cartridges 902, 932 on opposing walls, any number of cartridges may be utilized and may be removably attached to any of the walls of the body portion 920.

Figure 42:
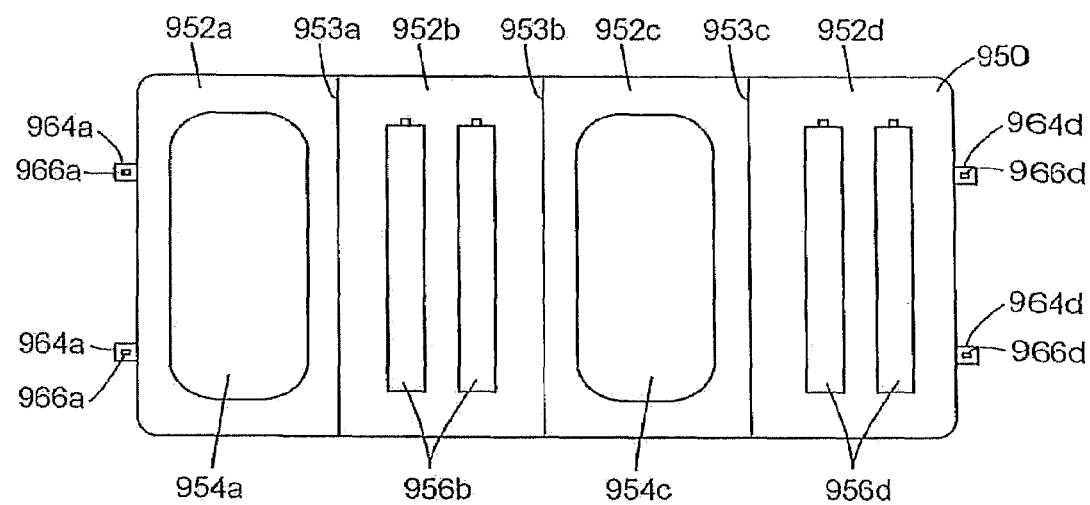
FIG. 42 is a plan view of a sixteenth embodiment of an active material cartridge.
Figure 43:
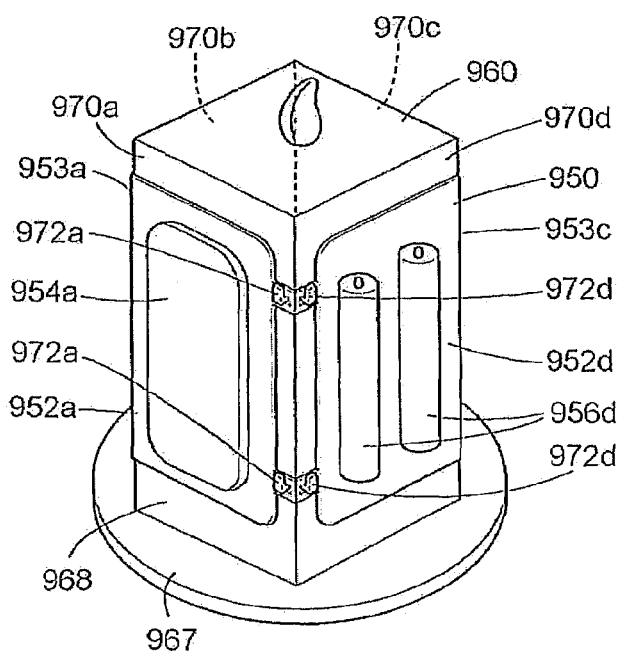
FIG. 43 is a top isometric view illustrating the cartridge of FIG. 42 attached to an active material emitting device.

As seen in FIGS. 42 and 43, a sixteenth embodiment of an active material cartridge 950 is depicted. The cartridge 950 includes first, second, third, and fourth sections 952a-952d that are integral with one another and include flexible portions 953a-953c between the sections 952a-952d. Each of the first and third sections 952a, 952c includes a reservoir 954a, 954c having active material therein and each of the second and fourth sections 952b, 952d may include one or more batteries 956b, 956d for powering an active material emitting device 960 to which the cartridge 950 may be attached. Preferably, the second and fourth sections 952b, 952d have apertures 961b, 961d, respectively, therein to retain the batteries 956b, 956d therein. The batteries 956b, 956d are inserted through the respective apertures 961b, 961d such that a portion of each battery 956b, 956d is behind the respective section 952b, 952d and a portion of each battery 956b, 956d is in front of the respective section 952b, 952d. Optionally, the cartridge 950 may only include a single section 952a-952d with a reservoir and a single section 952a-952d with one or more batteries 956. Each of the first and fourth sections 952a, 952d includes one or more tabs 964a, 964d, respectively, extending from ends thereof, wherein each of the tabs 964a, 964d includes an aperture 966a, 966d therein.

As seen in FIG. 43, the cartridge 950 is preferably attached to the active material emitting device 960. The device 960 includes a base portion 967 and a body portion 968 integral with and extending upwardly from the base portion 967. Further, the device 960 includes first, second, third, and fourth walls 970a-970d, wherein each of the first and fourth walls 970a, 970d includes one or more anchors 972a, 972d disposed thereon, which are similar to the anchors 764a, 764b of FIGS. 34 and 35.

The cartridge 950 is attached to the device 960 by positioning the cartridge 950 such that one set of anchors 972a, 972d extends through respective apertures 966a, 966d, wrapping the sections 952a-952d around the walls 970a-970b by bending the flexible portions 953a-953c, and latching the other set of apertures 966a, 966d onto the respective set of anchors 972a, 972d to secure the cartridge 950 on the device 960. Optionally, one set of apertures 966a, 966d may be omitted from the respective tabs 964a, 964d and replaced with securing means such that the first and fourth sections 952a, 952d may be attached to one another instead of to the first and fourth walls 970a, 970d of the device 960. Preferably, the batteries 956b, 956d are positioned such that the contacts 974b, 974d of the respective batteries 956b, 956d are behind the respective section 952b, 952*d* such that the batteries 956*b*, 956*d* may be inserted into recesses defining positive and negative terminals for powering the device 960. Also preferably, securement of the cartridge 950 on the device 960 retains the batteries 956*b*, 956*d* within the cartridge 950. The cartridge 950 may be removed to replace batteries 956 or replace the entire cartridge 950 by unlatching the apertures 966*a*, 966*d* from the respective anchors 972*a*, 972*d* and removing the cartridge 950.

Figure 44:
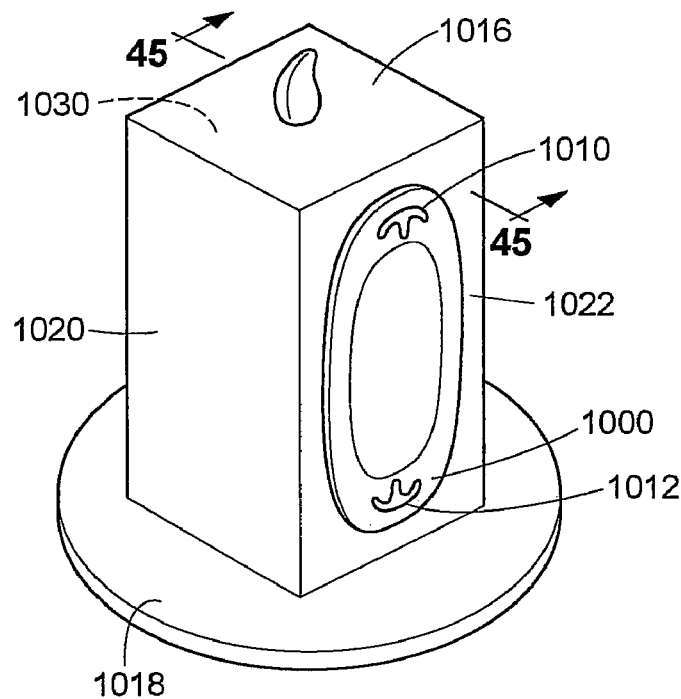
FIG. 44 is a top isometric view of a seventeenth embodiment of an active material cartridge disposed on an active material emitting device.
Figure 45:
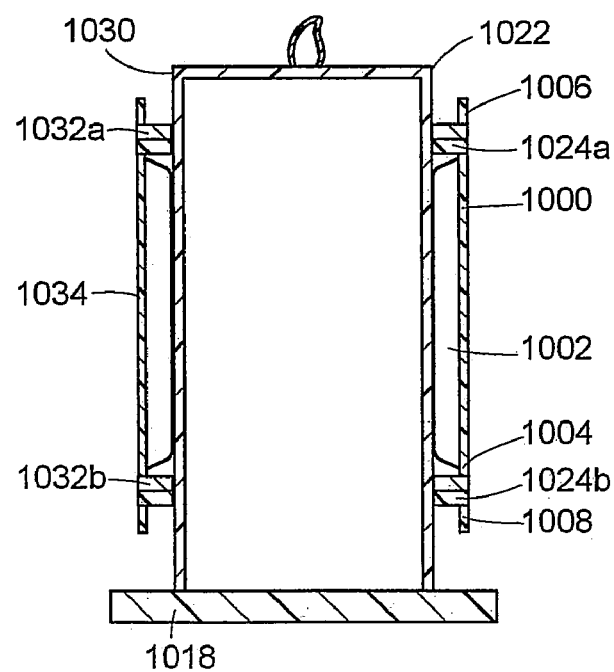
FIG. 45 is a cross-sectional view taken generally along the lines 45-45 of FIG. 44.

A seventeenth embodiment of an active material cartridge 1000 is illustrated in FIGS. 44 and 45, wherein the cartridge 1000 includes a reservoir 1002 having an active material therein and a lip portion 1004 surrounding the reservoir 1002. The lip portion 1004 includes a top portion 1006 and a bottom portion 1008, wherein the top portion 1006 includes a first generally T-shaped aperture 1010 and the bottom portion includes a second generally T-shaped aperture 1012. Although the apertures 1010, 1012 are shown as having similar sizes and shapes, the sizes and shapes may optionally be different, and/or may be any possible shape or size.

The cartridge 1000 may be attached to an active material emitting device 1016. An exemplary device 1016 includes a base portion 1018 and a body portion 1020 integral with and extending upwardly from the base portion 1018. A first wall 1022 of the body portion 1020 includes first and second spaced protrusions 1024*a*, 1024*b* extending therefrom, wherein the protrusions 1024*a*, 1024*b* have shapes that are complementary to the shapes of at least a portion of the respective apertures 1010, 1012 in the cartridge 1000. The cartridge 1000 may be positioned on the device 1016 such that the protrusions 1024*a*, 1024*b* engage walls that define the apertures 1010, 1012, respectively, thereby retaining the cartridge 1000 on the first wall 1022. As seen in FIG. 45, the device 1016 includes a second wall 1030 opposite the first wall 1022, wherein the second wall 1030 may include third and fourth protrusions 1032*a*, 1032*b* to secure and retain an optional second cartridge 1034 similar to the cartridge 1000. Optionally, any number of cartridges may be utilized in the embodiment of FIGS. 44 and 45, wherein the cartridges may be arranged on any wall of the body portion 1020.

Figure 46:
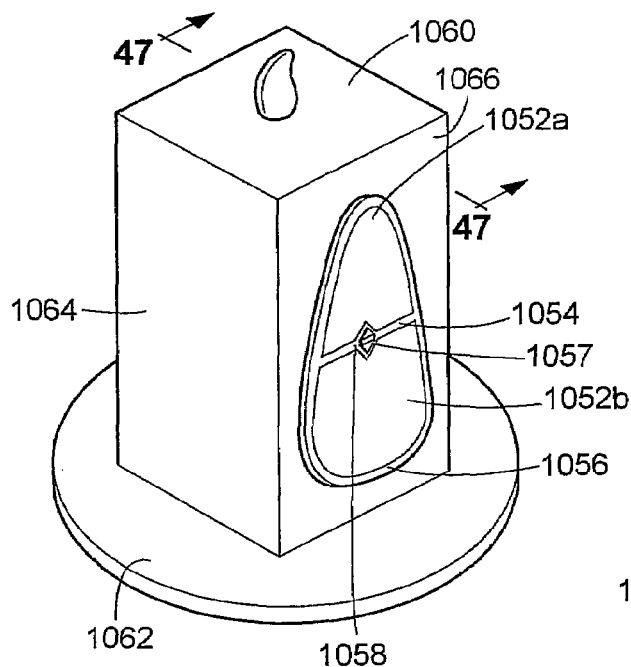
FIG. 46 is a top isometric view of an eighteenth embodiment of an active material cartridge disposed on an active material emitting device.
Figure 46A:
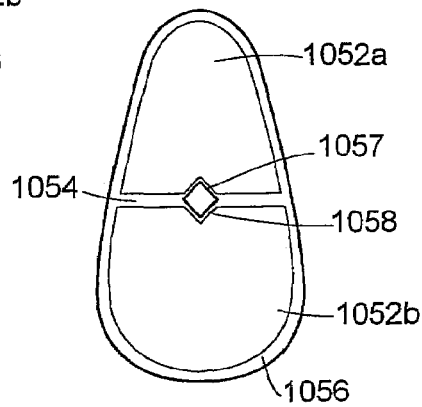
FIG. 46A is a front elevational view of the cartridge of FIG. 46.
Figure 47:
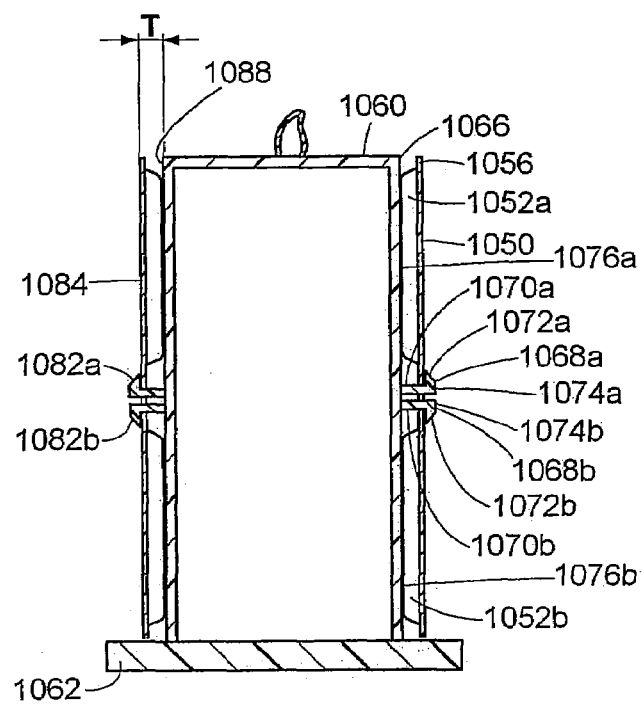
FIG. 47 is a cross-sectional view taken generally along the lines 47-47 of FIG. 46 illustrating a dual cartridge device.

The present invention may comprise an eighteenth embodiment of an active material cartridge 1050 as depicted in FIGS. 46, 46A, and 47. The cartridge 1050 includes first and second reservoirs 1052*a*, 1052*b* separated by a baffle 1054, wherein the reservoirs 1052*a*, 1052*b* are surrounded by a lip portion 1056 that is contiguous with the baffle 1054. The baffle 1054 preferably includes a triangular-shaped aperture 1057 in a central portion 1058 thereof.

The cartridge 1050 is preferably attached to an active material emitting device 1060, wherein the device 1060 includes a base portion 1062 and a body portion 1064 integral with the base portion 1062 and extending upwardly therefrom. A first wall 1066 of the device 1060 includes first and second flexible protrusions 1068*a*, 1068*b* (FIG. 47) extending from a central portion thereof, wherein each protrusion 1068*a*, 1068*b* includes a stem portion 1070*a*, 1070*b*, and a hook portion 1072*a*, 1072*b*, respectively, extending from the stem portion 1070*a*, 1070*b*. The cartridge 1050 is preferably attached to the device 1060, wherein the protrusions 1068*a*, 1068*b* extending from the first wall 1066 engage walls defining the aperture 1057. The walls defining the aperture 1057 preferably slide over the tip portions 1074*a*, 1074*b* of the hook portions 1072*a*, 1072*b* during installation of the cartridge 1050, such that the walls defining the aperture 1057 are disposed behind and adjacent the stem portions 1070*a*, 1070*b*. Preferably, the length of each stem portion 1070 is selected relative to the depth T of the cartridge at the reservoirs 1052 such that one or both of rear surfaces 1076*a*, 1076*b* of the reservoirs 1052*a*, 1052*b*, respectively, contact the wall 1066 when the walls defining at least a portion of the aperture 1057 are disposed behind and adjacent the stem portions 1070*a*, 1070*b*. The cartridge 1050 is removed by pressing the protrusions 1068*a*, 1068*b* toward one another and pulling the cartridge 1050 away from the device 1060 in a direction transverse to the pressure exerted on the protrusions 1068*a*, 1068*b*. As will be understood by one skilled in the art, any number of cartridges 1050 may be utilized and capable of attachment to any of the walls of the body portion 1064.

Optionally, as seen in FIG. 47, the device 1060 may include a second wall 1080 opposite the first wall 1066 including third and fourth protrusions 1082*a*, 1082*b* similar to the protrusions 1068*a*, 1068*b*, to secure and retain an optional second cartridge 1084, which is similar to the cartridge 1050. Still optionally, the cartridge(s) 1050 and/or 1084 may have a thickness T that is between about 4 mm and about 6 mm. In such an arrangement, a cartridge with a thickness 1 or 2 mm greater than T will not fit within the device 1060.

Figure 48:
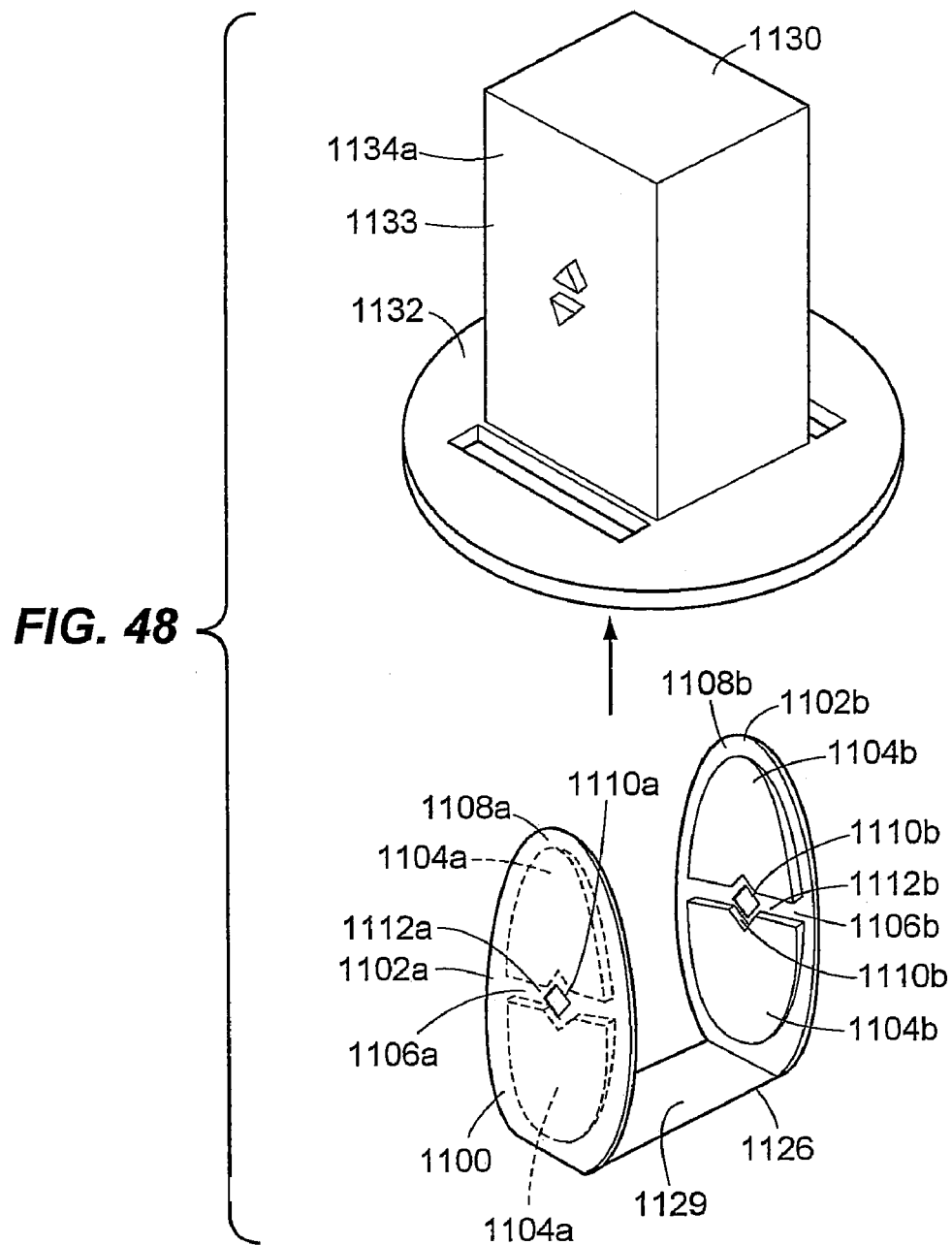
FIG. 48 is a top isometric view of a nineteenth embodiment of an active material cartridge illustrating insertion of the cartridge into an active material emitting device.
Figure 49:
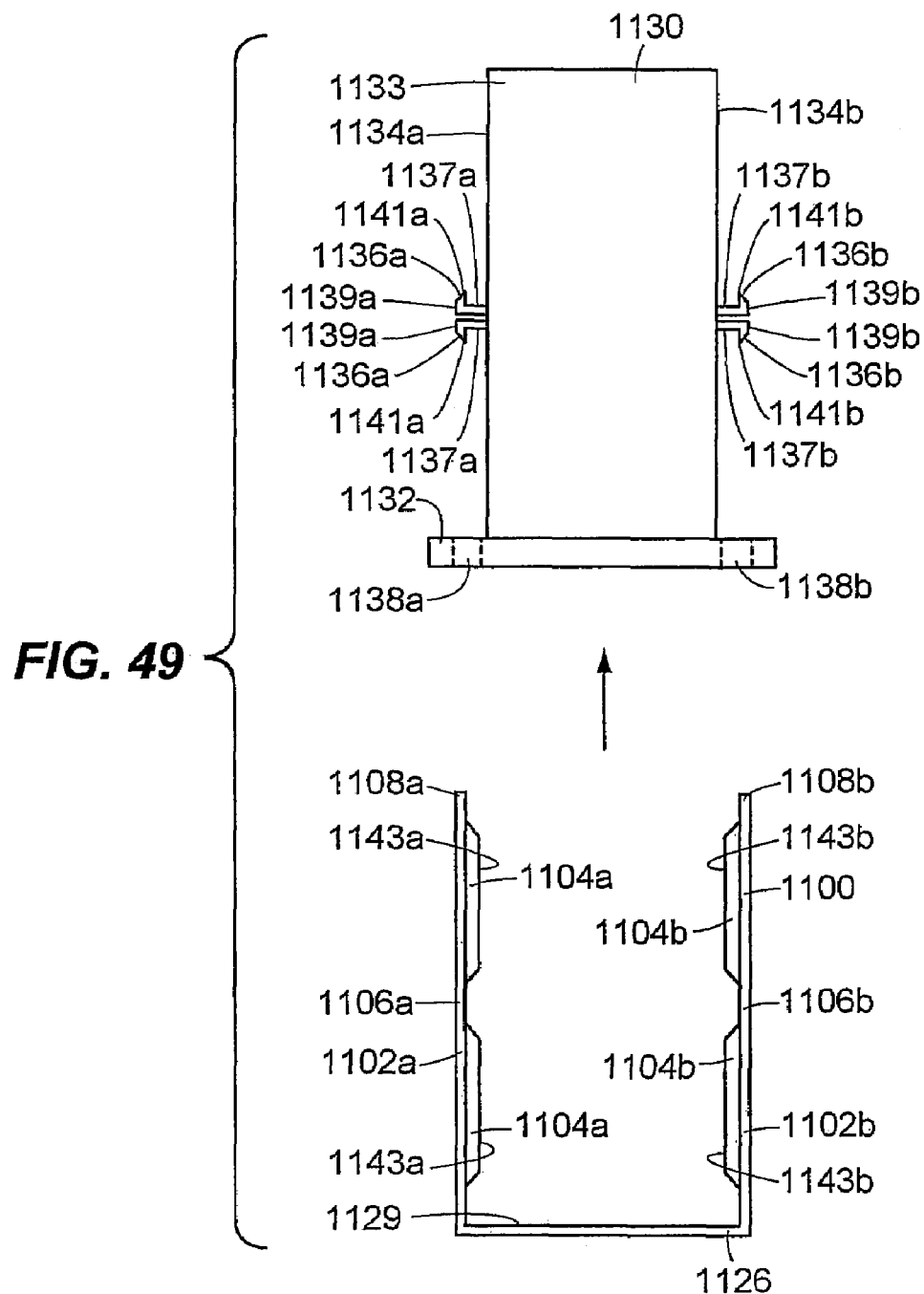
FIG. 49 is a front view of FIG. 48.

A nineteenth embodiment of an active material cartridge 1100 is shown in FIGS. 48 and 49. The cartridge 1100 includes first and second cartridge portions 1102*a*, 1102*b*. Each of the cartridge portions 1102*a*, 1102*b* includes two reservoirs 1104*a*, 1104*b* separated by baffles 1106*a*, 1106*b*, wherein each of the baffles 1106*a*, 1106*b* includes a lip portion 1108*a*, 1108*b* surrounding the respective reservoirs 1104*a*, 1104*b* and contiguous with the respective baffle 1106*a*, 1106*b*. Each of respective central portions 1112*a*, 1112*b* includes a triangular aperture 110*a*, 1110*b* formed therethrough. A connecting portion 1126 joins the lip portions 1108*a*, 1108*b* of the two cartridge portions 1102*a*, 1102*b*, respectively, thereby forming the unitary cartridge 1100. Optionally, the cartridge 1100 may include an upstanding projection extending from a top surface 1129 of the connecting portion 1126, wherein the upstanding projection may be similar to that described in connection with FIGS. 38 and 39.

The cartridge 1100 of FIGS. 48 and 49 is preferably attached to an active material emitting device 1130, wherein the device 1130 includes a base portion 1132 and a body portion 1133 integral with the base portion 1132 and extending upwardly therefrom. The device 1130 includes first and second opposing walls 1134*a*, 1134*b*, wherein each of the walls 1134*a*, 1134*b* includes two flexible protrusions 1136*a*, 1136*b*, respectively extending therefrom and spaced from one another. Each of the protrusions 1136*a*, 1136*b* includes a stem portion 1137*a*, 1137*b* and a hook portion 1139*a*, 1139*b*, respectively, extending from the stem portion 1137*a*, 1137*b*. First and second holes 1138*a*, 1138*b* are formed in the base portion 1132 adjacent the first and second walls 1134*a*, 1134*b*, respectively. Optionally, the device 1130 may include a switch and an actuator arm as described in detail with respect to the embodiment of FIGS. 38 and 39.

The cartridge 1100 is inserted into the device 1130 by inserting the cartridge portions 1102*a*, 1102*b* through the holes 1138*a*, 1138*b*, respectively, in the base portion 1132. Once the cartridge portions 1102*a*, 1102*b* have been fully inserted through the holes 1138*a*, 1138*b*, the protrusions 1136*a*, 1136*b* engage walls defining the apertures 110*a*, 1110*b*, to secure and retain the cartridge portions 1102*a*, 1102*b*. The walls defining the apertures 1110*a*, 1110*b* preferably slide over tip portions 1141*a*, 1141*b* of the hook portions 1139*a*, 1139*b* during installation of the cartridge 1100, such that the walls defining the apertures 110a, 1110b are disposed behind and adjacent the respective stem portions 1137a, 1137b. Preferably, the length of each stem portion 1137a, 1137b is selected relative to the depth T1 of the cartridge 1100 at the reservoirs 1104a, 1104b such that one or both of rear surfaces 1143a, 1143b of the respective reservoirs 1104a, 1104b contact the respective wall 1134a, 1134b when the walls defining at least a portion of the apertures 110a, 1110b are disposed behind and adjacent the stem portions 1137a, 1137b.

The present invention may comprise yet a twentieth embodiment of an active material cartridge 1150 as illustrated in FIGS. 50, 50A, 51, and 51A. The active material cartridge 1150 includes a frame 1152 with a reservoir 1154 having active material therein disposed in a front portion 1156 of the frame 1152 and surrounded entirely by the frame 1152. The frame 1152 further includes a flexible band 1158 attached to a lower portion 1160 of the frame 1152 between a first side 1161a and a second side 1161b thereof. The band 1158 and the frame 1152 form a hollow half-cylinder therebetween.

Figure 50:
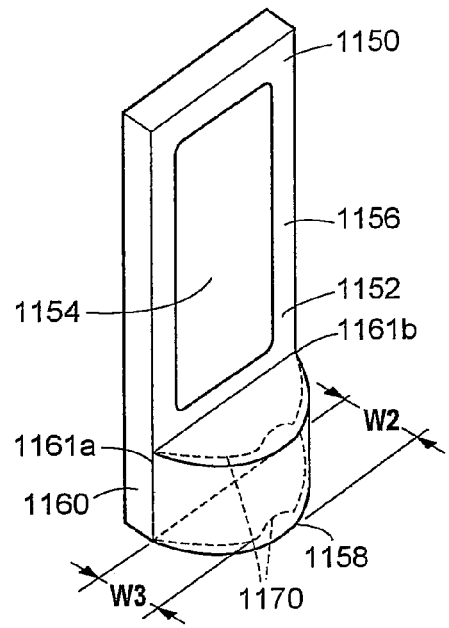
FIG. 50 is a top isometric view of a twentieth embodiment of an active material cartridge.
Figure 51:
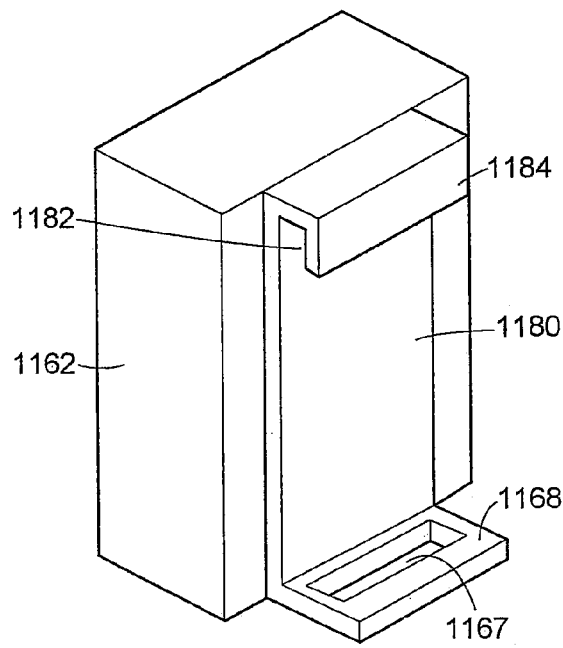
FIG. 51 is a top isometric view of an active material emitting device for use with the cartridges of FIGS. 50 and 50A.
Figure 51A:
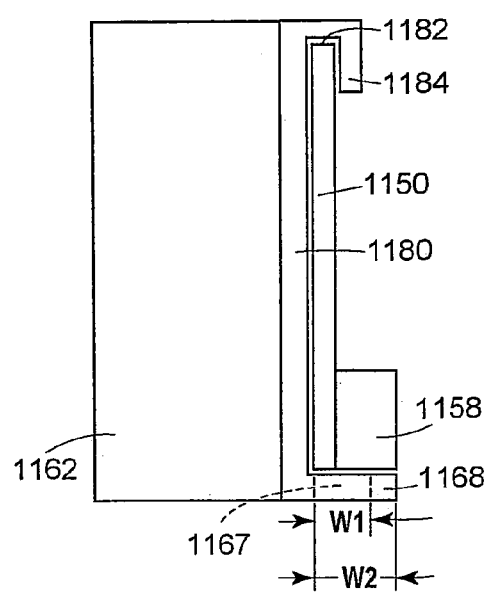
FIG. 51A is side view of the device of FIG. 51 with the cartridge of FIG. 50 inserted therein.

As seen in FIG. 51, the cartridge 1150 may be inserted into an active material emitting device 1162, wherein the device 1162 includes a base portion 1164 and a body portion 1166 integral with and extending upwardly from the base portion 1164. The base portion 1164 comprises an aperture 1167 therein, wherein a width W1 of the aperture 1167 is less than a width W2 of the cartridge 1150 as a whole. The cartridge 1150 is inserted through the aperture 1167 in the base portion 1164 of the device 1162 by flexing the band 1158 inwardly toward the frame 1152 to a flexed position 1170, as seen in FIG. 50. Once the band 1158 has been flexed inwardly, a width W3 of the cartridge 1150 as a whole is less than the width W1 of the aperture 1167, thereby allowing insertion of the cartridge 1150 through the aperture 1167. As the cartridge 1150 is inserted into the device 1162, the cartridge 1150 is guided along a wall 1180 of the device 1162 and into a slot 1182. After the cartridge 1150 has been fully inserted, the band 1158 flexes back to its original position, wherein upward movement of the cartridge 1150 is prevented by an interference between the cartridge 1150 and a flange 1184 that forms the slot 1182 and downward movement of the cartridge 1150 is prevented by an interference between the band 1158 and the base 1164. In this position, air may flow through the aperture 1167 in the base 1164 and through the band 1158 past the reservoir 1154 to aid in emission of the active material therein.

Figure 50A:
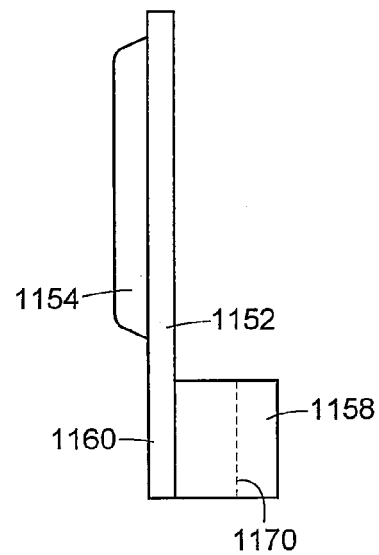
FIG. 50A is a side view of a cartridge similar to the cartridge of FIG. 50, wherein a frame does not completely surround a reservoir of active material.

Optionally, as seen in FIG. 50A, the frame 1152 may not surround the entire reservoir 1154 as in FIG. 50, but instead, may simply connect the reservoir 1154 and band 1158. In such case, insertion of the cartridge 1150 would be performed in the same manner as described with respect to FIG. 51.

Figure 52:
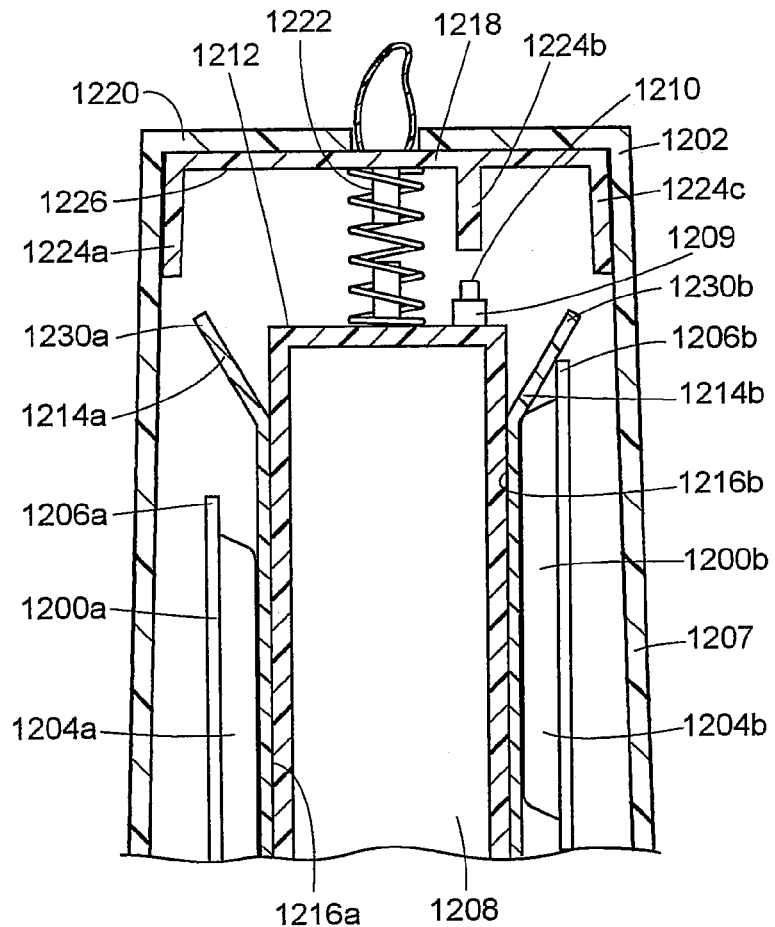
FIG. 52 is a front fragmentary cross-sectional view of a twenty-first embodiment of a cartridge disposed in an active material emitting device.
Figure 53:
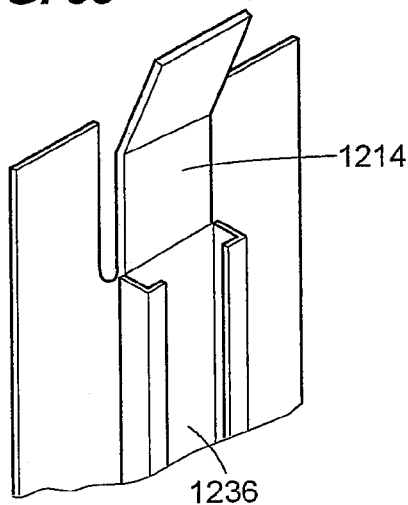
FIG. 53 is a fragmentary isometric view of a flexible finger of FIG. 52.

A twenty-first embodiment of one or more active material cartridges 1200a, 1200b for insertion into an active material emitting device 1202 is depicted in FIGS. 52 and 53. Each of the cartridges 1200a, 1200b includes a reservoir 1204a, 1204b having a lip portion 1206a, 1206b surrounding the respective reservoir 1204a, 1204b. Preferably, the lip portions 1206a, 1206b are semi-rigid. The device 1202 is similar to the device 100 described in detail with respect to the embodiment of FIGS. 1-7.

The device 1202 includes a body 1207 that holds the components of the device 1202. In particular, a chassis 1208 is disposed within the device 1202, wherein the chassis 1208 includes a switch 1209 with an actuator arm 1210 extending therefrom, wherein the switch 1209 extends from a top surface 1212 of the chassis 1208. First and second flexible fingers 1214a, 1214b are secured to side portions 1216a, 1216b, respectively, of the chassis 1208. The device 1202 further includes a vent portion 1218 disposed adjacent a top wall 1220 of the body 1207, wherein a spring 1222 is disposed between the chassis 1208 and the vent portion 1218 to provide spring-loaded movement to the vent portion 1218. The vent portion 1218 also includes first, second, and third projections 1224a-1224c extending from a bottom surface 1226 thereof.

When cartridges 1200a, 1200b are not inserted into the device 1202, the flexible fingers 1214a, 1214b abut the first and third projections 1224a, 1224c, thereby preventing the vent portion 1218 from moving downwardly. When the cartridges 1200a, 1200b are inserted into the device 1202 along the flexible fingers 1214a, 1214b, respectively, the cartridges 1200a, 1200b cause top portions 1230a, 1230b of the flexible fingers 1214a, 1214b to flex inwardly thereby allowing the vent portion 1218 to move downwardly. In order for the vent portion 1218 to work properly and move downwardly, both cartridges 1200a, 1200b must be inserted into the device 1202. Once the vent portion 1218 is allowed to move downwardly, the second projection 1224b may, with the downward motion of the vent portion 1218, contact the actuator arm 1210 of the switch 1209 to actuate a light 1232 or any other component within the device 1202. Preferably, each of the flexible fingers 1214a, 1214b includes a means for securing the respective cartridge 1200a, 1200b adjacent the respective flexible finger 1214a, 1214b. FIG. 53 depicts the means for securing in the form of a slot 1236, wherein each cartridge 1200a, 1200b is inserted into the respective slot 1236 and moved along the respective flexible finger 1214a, 1214b. Optionally, any other means for securing may be utilized.

Figure 54:
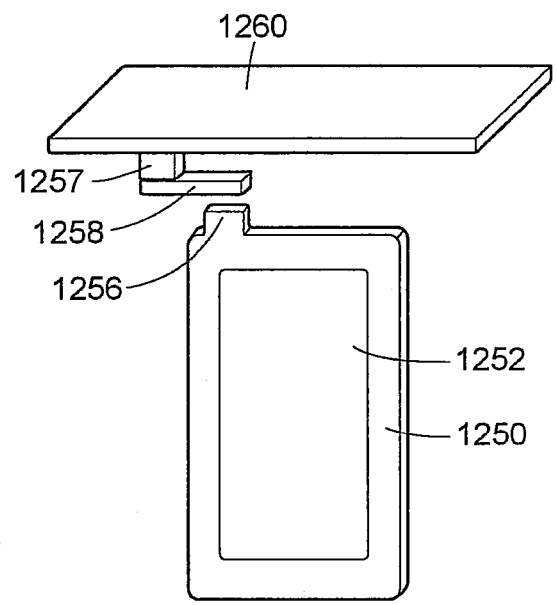
FIG. 54 is a top isometric view of a twenty-second embodiment of a cartridge.
Figure 55:
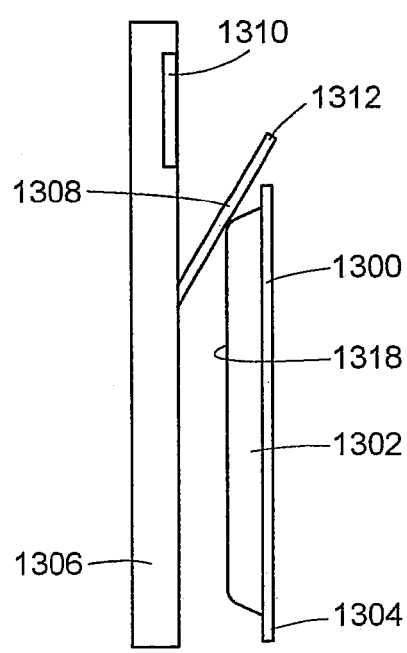
FIG. 55 is a side view of a twenty-third embodiment of a cartridge.
Figure 56:
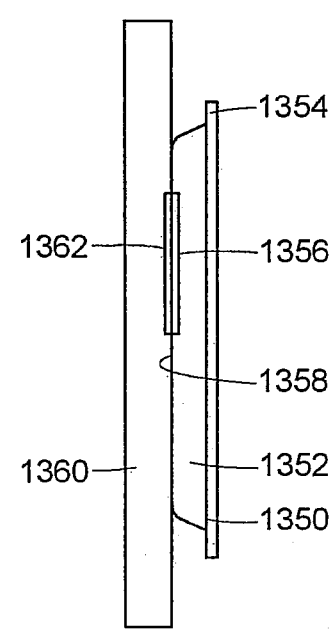
FIG. 56 is a side view of a twenty-fourth embodiment of a cartridge.
Figure 57:
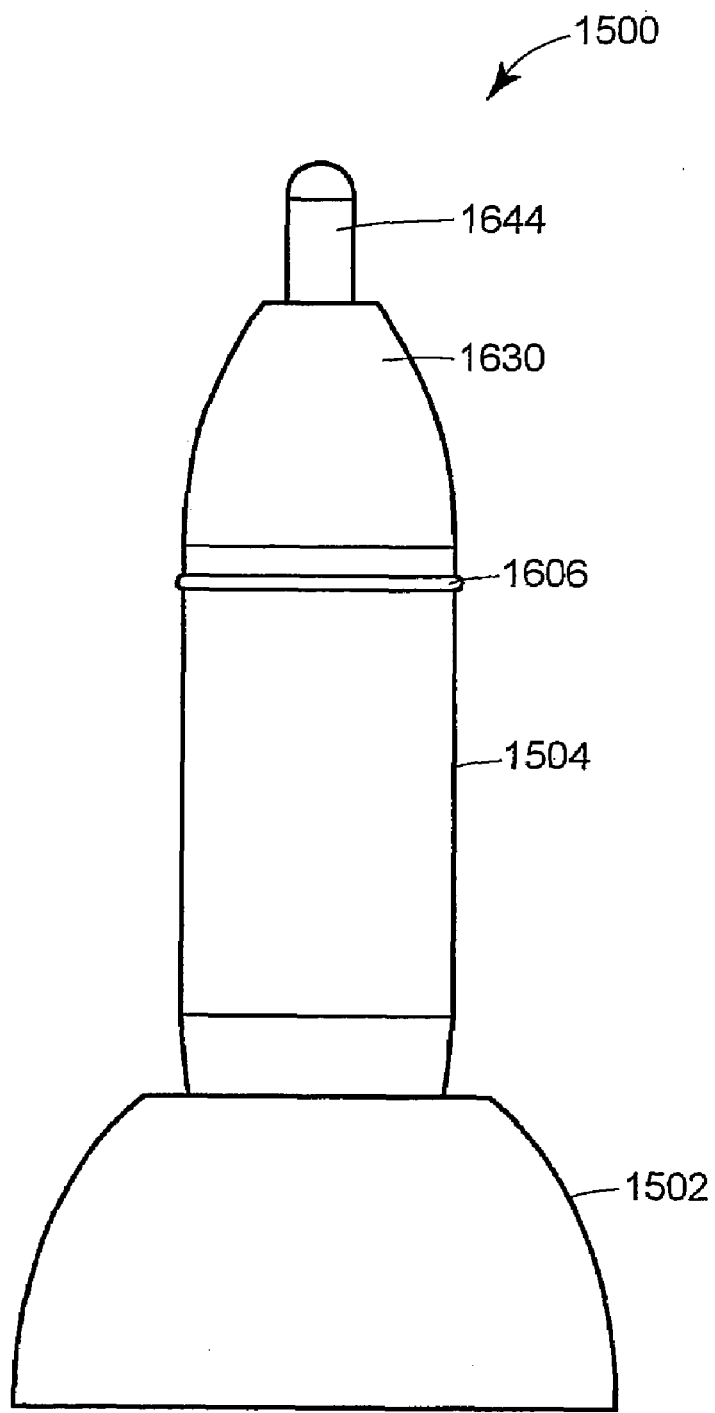
FIG. 57 is a front elevational view of a twenty-fifth embodiment of an active material cartridge in a closed position.
Figure 58:
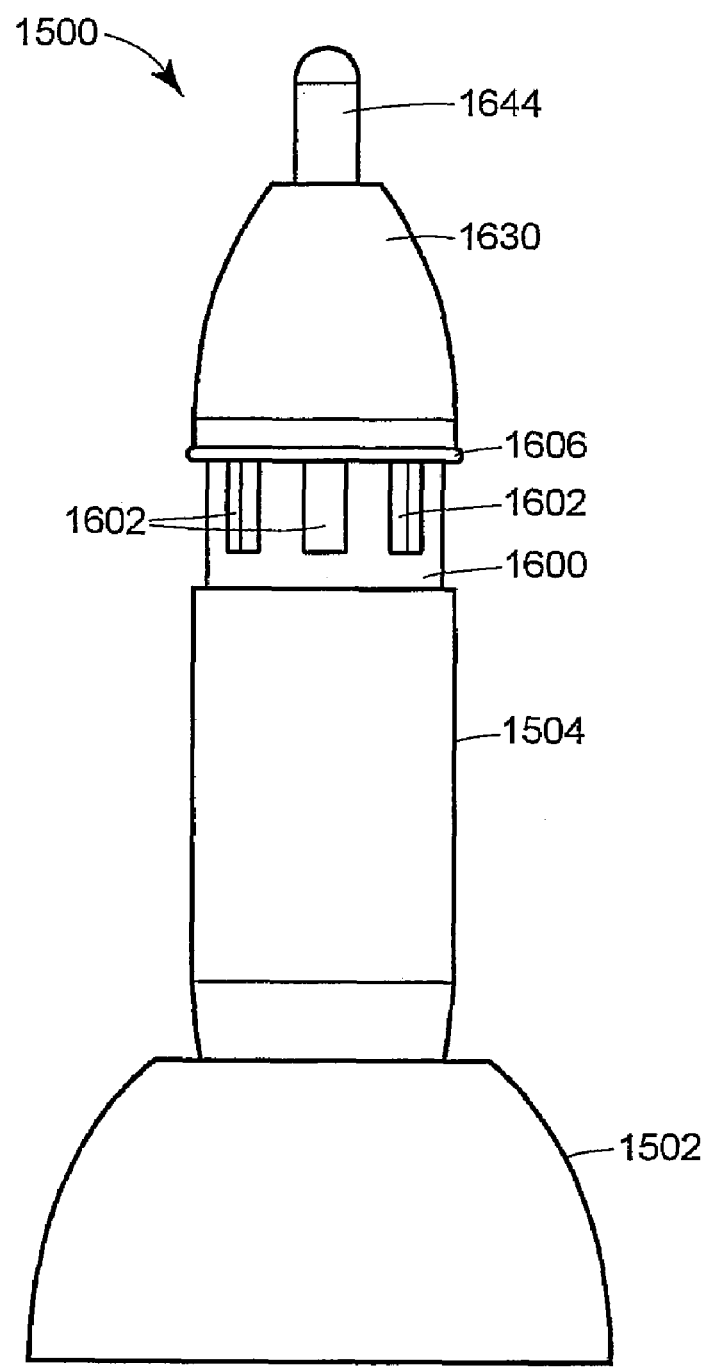
FIG. 58 is a front elevational view of the embodiment of FIG. 57 in an open position.

The present invention may comprise further embodiments of an active material cartridge as illustrated in FIGS. 54-56 that utilize various mechanical and electrical switches in combination with one or more active material cartridge(s) to notify a device that the cartridge(s) is in position. FIG. 54 depicts a twenty-second embodiment of an active material cartridge 1250 comprising a reservoir 1252 having an active material therein, a lip portion 1254 surrounding the reservoir 1252, and a projection 1256 integral with and extending outwardly from the lip portion 1254. The cartridge 1250 may be inserted into an active material emitting device such as the device 100 of FIGS. 1-7 such that the projection 1256 contacts and depresses or activates an actuator arm 1258 of a mechanical switch 1257 that is operatively connected to a circuit board 1260. Once the actuator arm 1258 is depressed, the device 100 may detect that the cartridge 1250 has been inserted. Optionally, the mechanical switch 1258 may be replaced with an electrical contact and the projection 1256 may be conductive, so as to create an electrical switch.

A twenty-third embodiment of a cartridge 1300 is depicted in FIG. 55, wherein the cartridge 1300 includes a reservoir 1302 having an active material therein and a lip portion 1304 surrounding the reservoir 1302. The cartridge 1300 is preferably inserted into an active material emitting device such as the device 100 of FIGS. 1-7 for use thereof. The device 100 includes a component 1306, such as a wall, surface, circuit board, or any other component, having a spring finger 1308, preferably made of a conductive material, protruding therefrom and a contact 1310 spaced from an end 1312 of the spring finger 1308. As the cartridge 1300 is inserted, a bottom surface 1318 of the cartridge 1300 depresses the spring finger 1308, thereby moving the end 1312 of the spring finger 1308 into electrical connection with the contact 1310. Optionally, the switch of FIG. 55 may be a mechanical switch where the contact 1310 is replaced by a mechanical switch and the mechanical switch is actuated by contact with the spring finger 1308.

FIG. 56 illustrates still a twenty-fourth embodiment of a cartridge 1350. The cartridge 1350 comprises a reservoir 1352 having active material therein and a lip portion 1354 surrounding the reservoir 1352, wherein a first circuit-forming element 1356 is disposed on a bottom surface 1358 of the reservoir 1352. Preferably, the cartridge 1350 is inserted into an active material emitting device such as the device 100 of FIGS. 1-7 that comprises a component 1360, such as a wall, surface, circuit board, or any other component, having a second circuit-forming element 1362 disposed thereon. After the cartridge 1350 is inserted into the device 100, the first circuit-forming element 1356 on the cartridge 1350 is adapted to be disposed adjacent the second circuit-forming element 1362, thereby forming a circuit and alerting the device 100 that a cartridge 1350 is disposed within the device 100. The first and second circuit-forming elements 1356, 1362 may be any type of circuit-forming elements, including, but not limited to, conductive inks, foil hot stamping, conductive metal components, resistors, electrical elements, or any other known circuit-forming elements. Optionally, the reservoir 1352 may be made from a conductive material and the active material therein may also be conductive, thereby making the entire cartridge 1350 conductive.

Figure 59:
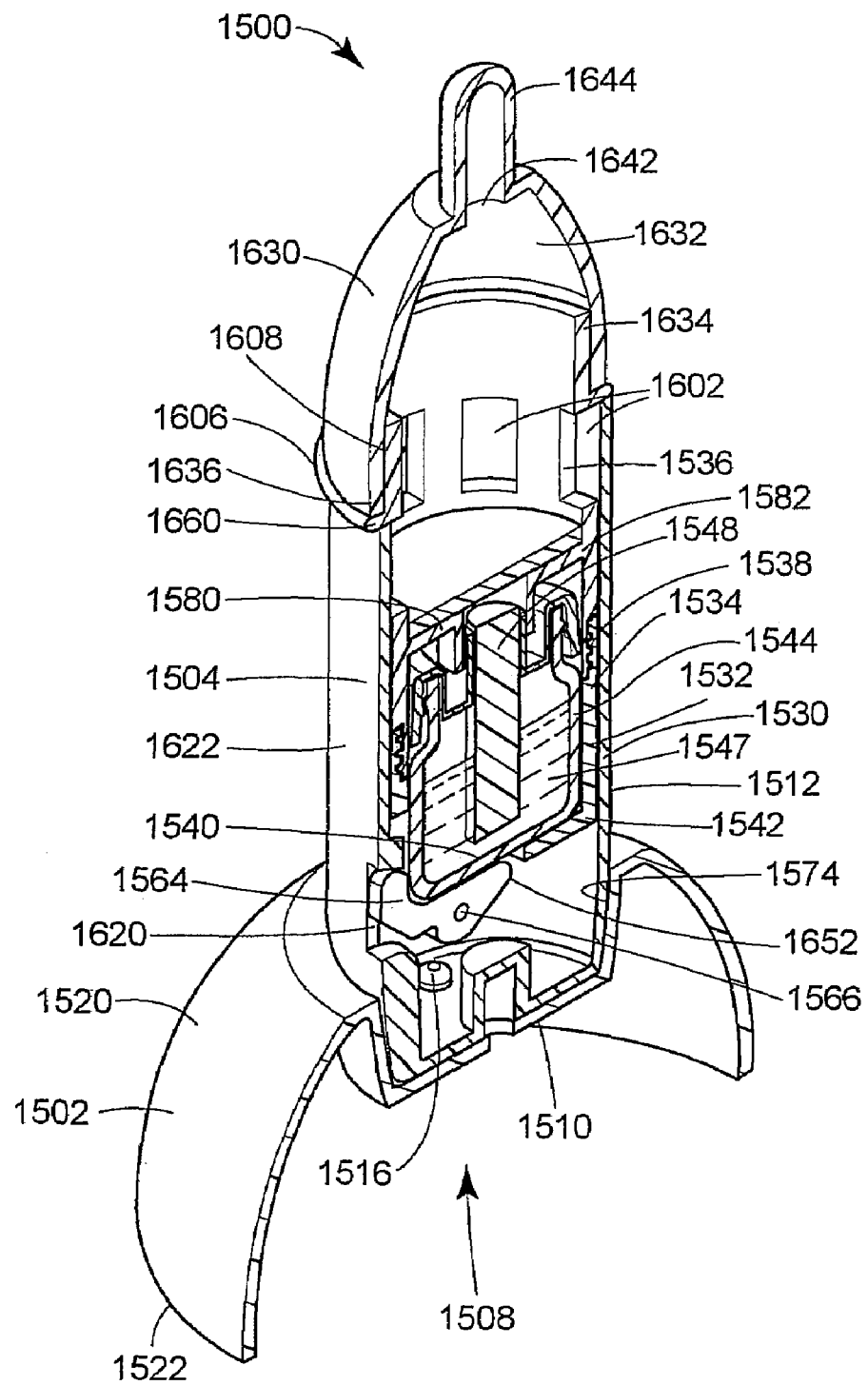
FIG. 59 is an isometric view of the embodiment as shown in FIG. 57 with portions cut away and in cross-section.
Figure 60:
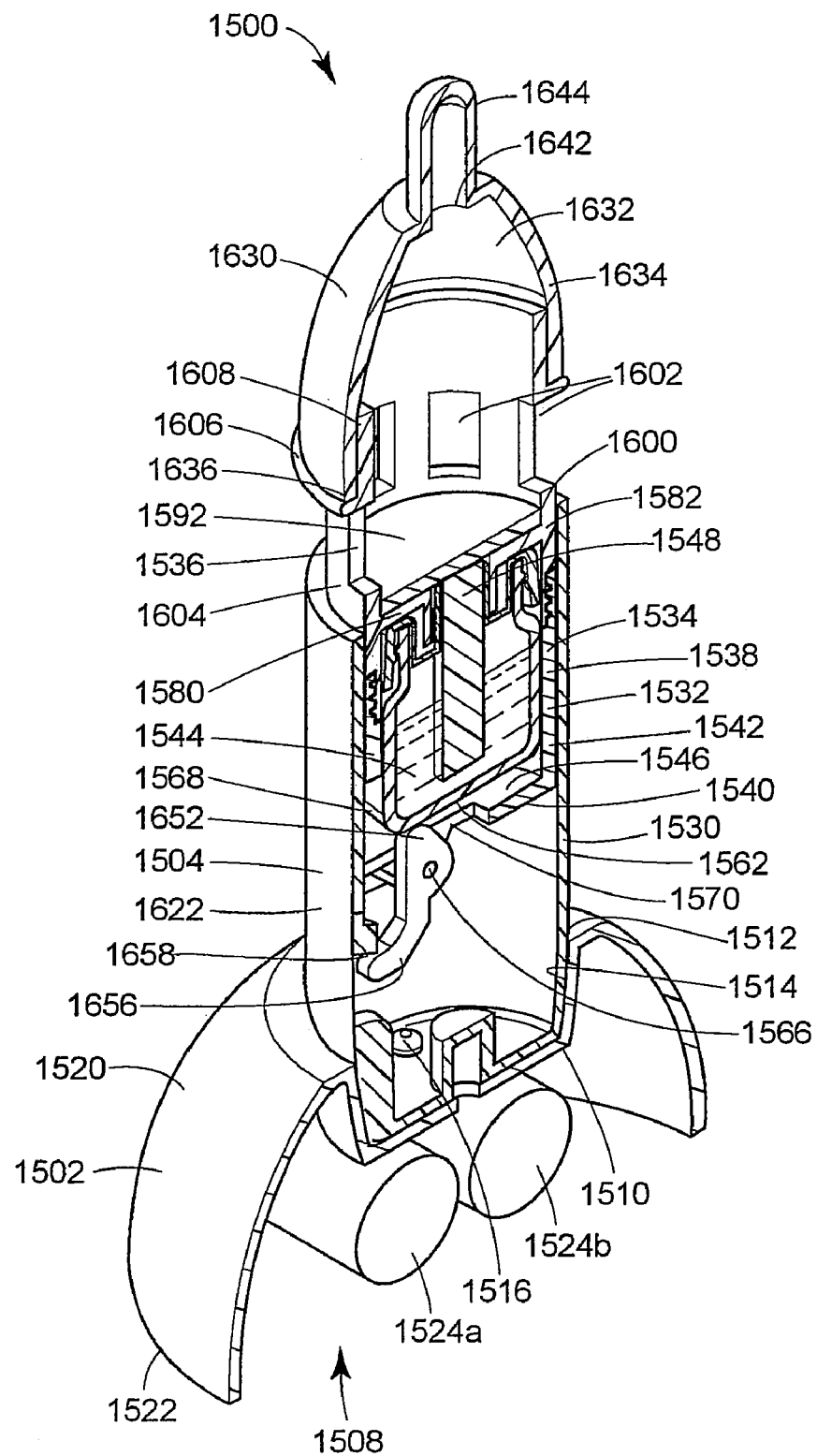
FIG. 60 is an isometric view of the embodiment as shown in FIG. 58 with portions cut away and in cross-section.

A twenty-fifth embodiment of an active material cartridge 1500 is illustrated in FIGS. 57-62. Referring to FIGS. 59 and 60, the cartridge 1500 includes a base portion 1502 and a cylindrical body portion 1504, wherein the base portion 1502 preferably includes a cylindrical cavity 1508 in a central portion 1510 thereof. The body portion 1504 is removably inserted into the cavity 1508 of the base portion 1502 such that an outer surface 1512 of the cylindrical body portion 1504 engages an inner surface 1514 of the cavity 1508. Preferably, the body portion 1504 is secured in the cavity 1508 by one or more screws 1516. Optionally, any other means may be used to secured the body portion 1504 within the cavity 1508, such as an interference fit arrangement, a snap fit arrangement, adhesive, fasteners, and the like, and combinations thereof. Also optionally, any other attachment means may be utilized, including permanent attachment means.

The base portion 1502 is hollow and comprises a hollow half sphere-shaped wall 1520, wherein a bottom edge 1522 of the wall 1520 is adapted to be positioned on a surface for use thereof. Preferably, although not necessarily, the base portion 1502 may accommodate one or more batteries 1524a, 1524b (FIG. 60) that provide power to the cartridge 1500.

Referring again to FIGS. 59 and 60, The cartridge 1500 includes an outer sleeve 1530 and an inner sleeve 1532 that is disposed adjacent and in sliding engagement with the outer sleeve 1530. The inner sleeve 1532 includes a bottom portion 1534 and a top portion 1536 disposed above and integral with the bottom portion 1534. The bottom portion 1534 includes a first cylindrical wall 1538 and a circular bottom wall 1540 connecting a bottom periphery 1542 of the first cylindrical wall 1538. In a closed position (FIG. 59), a container 1544 rests upon a top surface 1546 of the bottom wall 1540. The container 1544 comprises an active material 1547, preferably a liquid active material, disposed therein and a wick 1548 extending upwardly therefrom.

Figure 62:
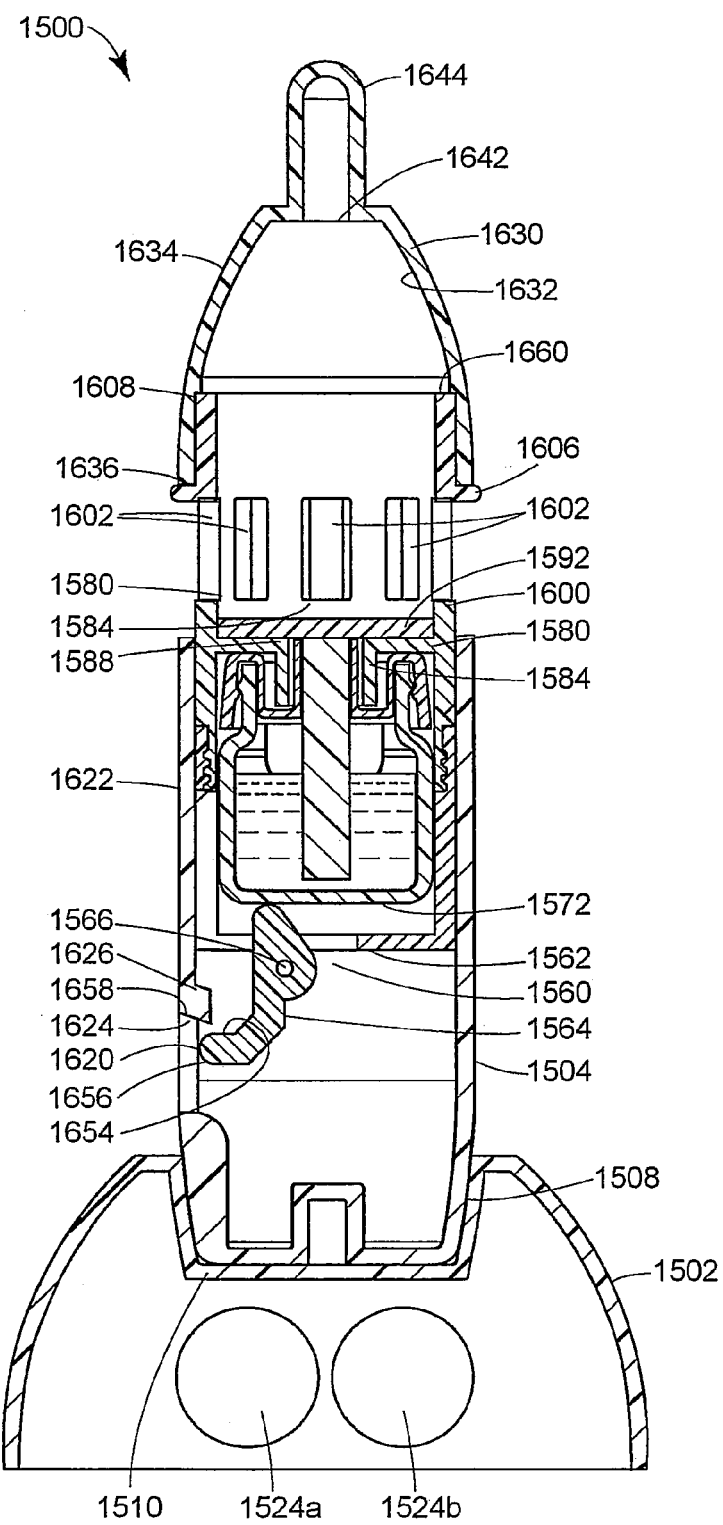
FIG. 62 is a front elevational view of the embodiment as shown in FIG. 60.

Referring to FIG. 62, a protrusion 1560 extends from a bottom surface 1562 of the bottom wall 1540. A rotatable lever 1564 is secured to the protrusion 1560 at a pivot point 1566 such that the rotatable lever 1564 may move about the pivot point 1566. As further seen in FIG. 60, a portion 1568 of the first cylindrical wall 1538 and a portion 1570 of the bottom wall 1540 are removed to allow the lever 1564 to rest against a bottom surface 1572 of the container 1544 in a closed position (FIG. 59).

Figure 61:
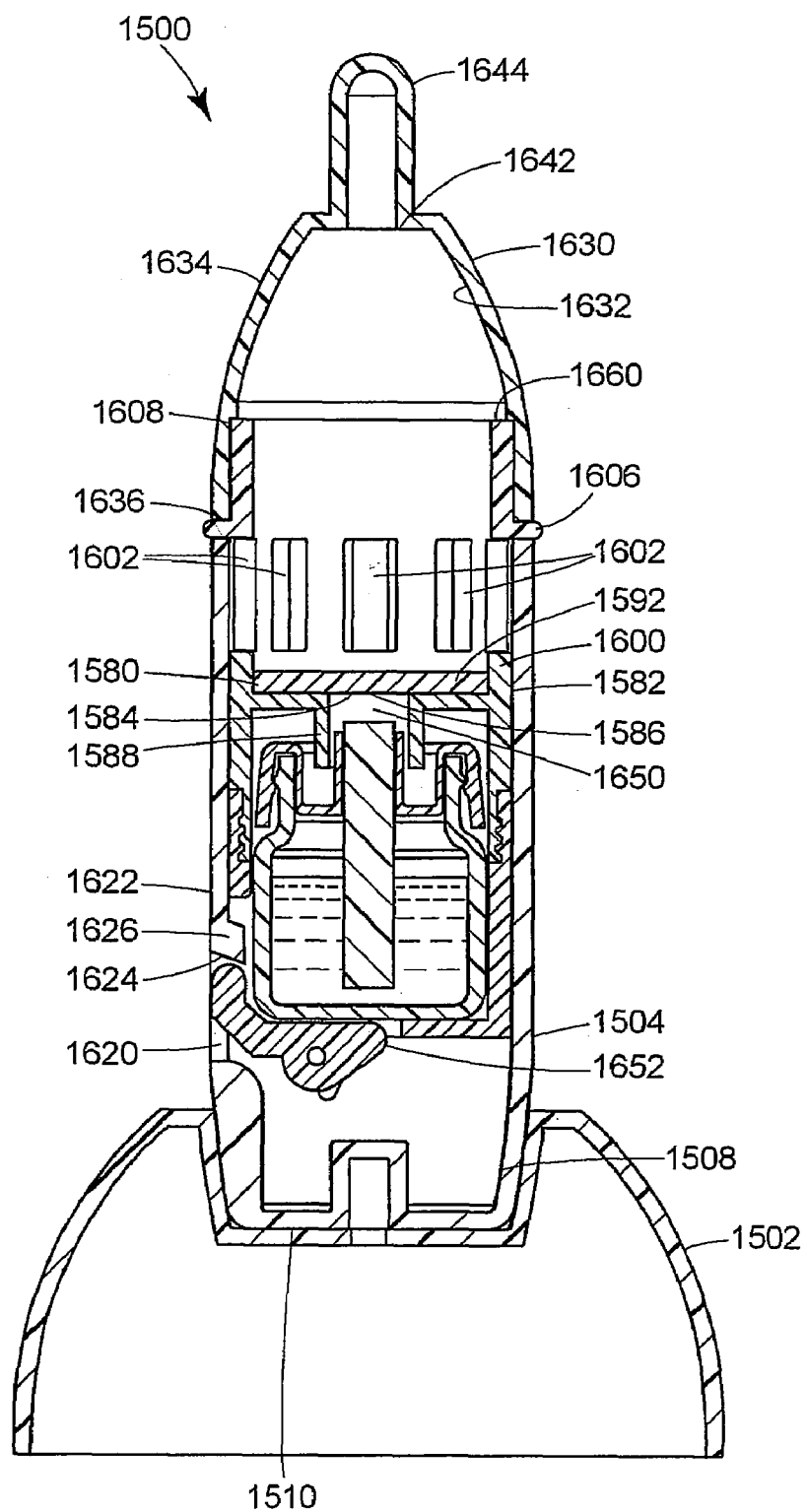
FIG. 61 is a front elevational view of the embodiment as shown in FIG. 59.

As seen in FIG. 61, a circular top wall 1580 extends across a top periphery 1582 of the first cylindrical wall 1538. The top wall 1580 has a circular aperture 1584 extending through a central portion 1586 thereof and a second cylindrical wall 1588 extending from the top wall 1580 and surrounding the circular aperture 1584. Preferably, a circular porous pad 1592 that acts as an emanator and has a minimal thickness is disposed atop the top wall 1580.

Referring to FIGS. 59 and 60, the top portion 1536 of the inner sleeve 1532 includes a third cylindrical wall 1600 integral with and extending upwardly from the first cylindrical wall 1538. The third cylindrical wall 1600 includes a plurality of apertures 1602 disposed about a periphery 1604 thereof. The apertures 1602 provide venting to the cartridge 1500, thus allowing circulation of the active material 1547. The third cylindrical wall 1600 also includes a circular flange portion 1606 about the periphery 1604 thereof, wherein the flange portion 1606 is disposed above the apertures 1602, but below a top periphery 1608 of the third cylindrical wall 1600.

A semi-cylindrical cap 1630 is secured to the third cylindrical wall 1600 such that an inner surface 1632 of the cap 1630 engages an outer surface 1634 of the third cylindrical wall 1600 and bottom periphery 1636 of the cap 1630 rests upon the flange portion 1606 of the third cylindrical wall 1600. Preferably, the cap 1630 is removably secured to the third cylindrical wall 1600 by a snap-fit arrangement, an interference fit arrangement, fasteners, combinations thereof, or any other known means for securing. Optionally, the cap 1630 may be permanently attached to the third cylindrical wall 1600 by molding and the like. The cap 1630 tapers into a point at a top portion 1642 thereof, wherein a lens 1644 is disposed in the top portion 1642. Optionally, one or more LED's may be disposed in the lens 1644 for emitting light therefrom.

Still referring to FIGS. 59-62, the outer sleeve 1530 includes a slot-like longitudinal aperture 1620 in a periphery 1622 thereof, wherein a top wall 1624 defining the aperture 1620 has a tab 1626 protruding therefrom, wherein the tab 1626 extends inwardly into the portion 1568 of the first cylindrical wall 1538 that has been removed. In a closed position, as seen in FIGS. 59 and 61, the lever 1564 extending from the bottom wall 1540 of the inner sleeve 1532 is disposed in the slot adjacent the tab 1626.

As seen in FIGS. 59 and 61, the cartridge 1500 is in a closed position. In this closed position, the container 1544 and wick 1548 disposed therein are spaced from the porous pad 1592, thus creating an air gap 1650 (FIG. 61) therebetween. The air gap 1650 prevents liquid active material 1547 from being transferred from the wick 1548 to the porous pad 1592, thus lowering the amount of active material 1547 emitted from the cartridge 1500. Also in the closed position, the outer sleeve 1530 is disposed around the inner sleeve 1532 such that the outer sleeve 1530 extends to a lower limit defined by the outer sleeve 1530 contacting the flange portion 1606. In such position, the apertures 1602 in the third cylindrical wall 1600 are concealed by the outer sleeve 1530, thereby preventing circulation of fresh air into the cartridge 1500 and fragranced air out of the cartridge 1500.

When a user desires to emit the active material 1547 into the surrounding environment, the cap 1630 may be grasped and moved upwardly. When such motion occurs, the cap 1630 and the entire inner sleeve 1532 also move upwardly. As the inner sleeve 1532 moves upwardly, so does the protrusion 1560 extending from the bottom surface 1562 of the inner sleeve 1532. The upward movement of the protrusion 1560 causes the lever 1564 to bear against the tab 1626, wherein the tab 1626 prevents the lever 1564 from moving upwardly. Since the lever 1564 cannot move upwardly, it begins to rotate about the pivot point 1566. As the lever 1564 rotates, an end 1652 of the lever 1564 rotates through the portion 1562 of the bottom wall 1540 that has been removed, thereby camming against the container 1554 and moving the container 1554 upwardly away from the bottom wall 1540 of the inner sleeve 1532.

The upward movement of the inner sleeve 1532 allows the third cylindrical wall 1600 to extend above the outer sleeve 1530, thus exposing the apertures 1602 in the third cylindrical wall 1600. Further, the upward movement of the container 1544 within the bottom portion 1534 of the inner sleeve 1532 moves the wick 1548 extending from the container 1544 into communication with the porous pad 1592. This communication allows the wick 1594 to transfer active material 1547 to the porous pad 1594, wherein active material 1547 emitted from the porous pad 1594 may be circulated out of the cartridge 1500 through the apertures 1602 in the third cylindrical wall 1600.

As best seen in FIG. 62, an upper limit of movement of the inner sleeve 1532 is defined by a side surface 1654 of a finger portion 1656 of the lever 1564 bearing against and being stopped by a bottom wall 1658 of the tab 1626, thereby preventing further upward movement of the inner sleeve 1532. When a user desires to close the cartridge 1500, downward pressure is exerted on the cap 1630 to move the inner sleeve 1532 downwardly within the outer sleeve 1530. As this occurs, the lever 1564 rotates back to its original position, wherein the lower limit is defined by the flange portion 1606 of the third cylindrical wall 1600 abutting an upper edge 1660 of the outer sleeve 1530 (FIGS. 59 and 61). In this position, the finger portion 1656 of the lever 1564 resides fully in the slot-like aperture 1620. Although the cartridge 1500 allows up and down movement of the inner sleeve 1532 within the outer sleeve 1530, the cartridge 1500 prevents rotational movement of the inner sleeve 1532 within the outer sleeve 1530. Specifically, the outer sleeve 1530 surrounding the finger portion 1656 of the lever 1564 creates an interference with the finger portion 1656 upon attempted rotational movement of the inner sleeve 1532.

Figure 63:
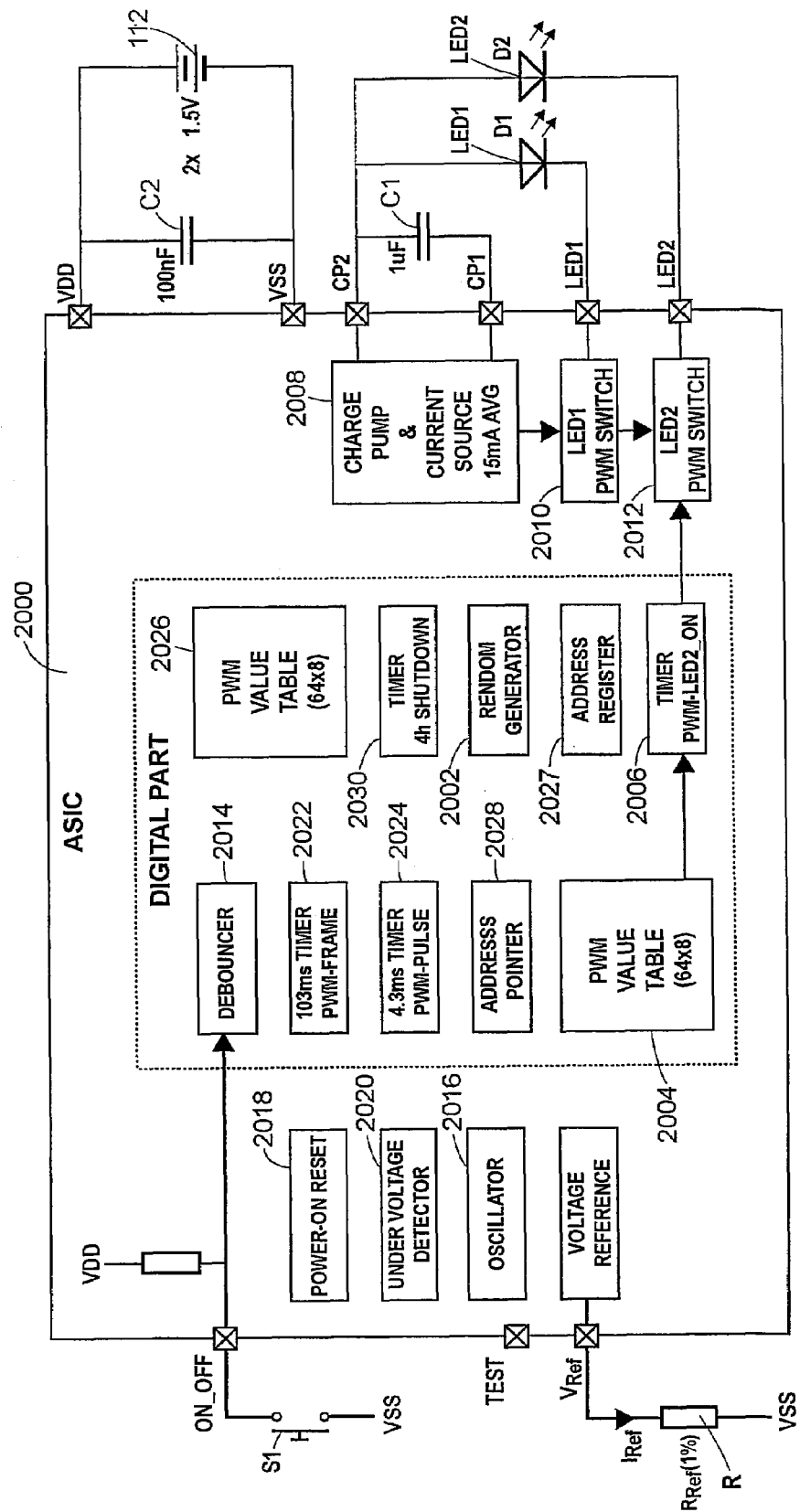
FIG. 63 is a block diagram of a programmable device in the form of an application specific integrated circuit (ASIC) that may be used to control LED1 and LED2 of FIG. 4.

FIG. 63 illustrates a device in the form of an application specific integrated circuit (ASIC) 2000 that operates in conjunction with further electrical components to control the energization of LED1 138a and LED2 138b. If desired, the ASIC 2000 may be replaced by a microcontroller, any other programmable device or a series of discrete logic and electronic devices. In general, the ASIC 2000 operates LED1 138a and LED2 138b such that LED1 138a appears to be continuously energized and LED2 138b appears to flicker. If desired, the ASIC 2000 could alternatively cause LED1 138a to appear to flicker and LED2 138b to appear to be continuously energized or both of LED1 138a and LED2 138b could be caused to appear to flicker or appear to be continuously energized. In the preferred embodiment, as described in greater detail hereinafter, the LED1 138a is, in fact, pulsed at a high frequency wherein the frequency is sufficient to create the appearance that the LED1 138a is continuously energized. This conserves battery power.

Figure 66:
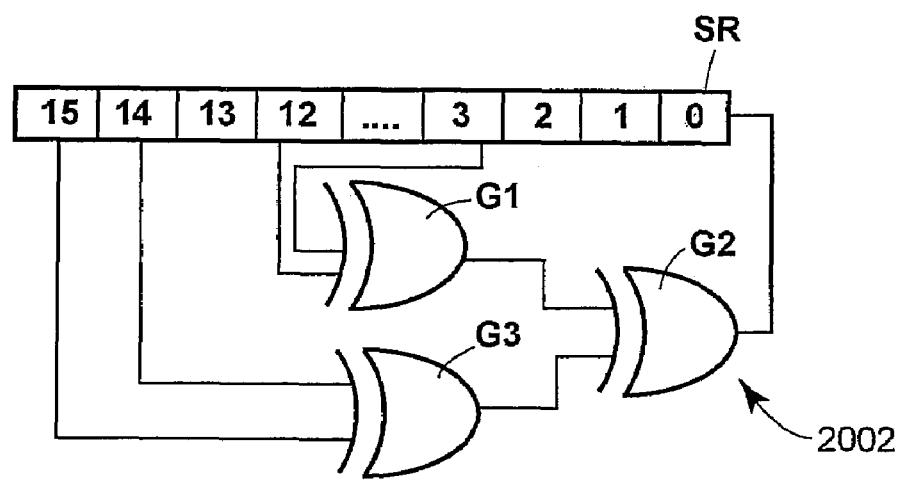
FIG. 66 is a block diagram illustrating the functionality of the pseudo random number generator of FIG. 63.

Also in the preferred embodiment, the LED2 138b is energized to obtain the flickering effect by utilizing a pseudo random number generator 2002 in conjunction with a pulse width modulation (PWM) value table 2004 and a timer 2006 to establish a duty cycle for operation of the LED2 138b. The pseudo random number generator 2002 is functionally shown in the block diagram of FIG. 66 as a series of three NOR gates G1, G2, and G3 coupled to particular bit positions of a sixteen-bit shift register SR. The initial value of the generator 2002 is 3045 (hexadecimal).

A charge pump and average current source 2008 is provided in conjunction with PWM switches 2010 and 2012 for LED1 138a and LED2 138b, respectively, to properly operate the LED's 138a, 138b. A capacitor C1 stores charge from the charge pump to permit continued operation of LED1 and LED2 even when the output voltage of the batteries 112a, 112b falls below the voltage required to turn on LED1 138a and LED2 138b.

The ASIC 2000 receives power from the batteries 112a, 112b, which may be a pair of series-connected conventional AA 1.5 v cells. A capacitor C2 is coupled across voltages VDD and VSS of the ASIC 2000 for filtering purposes. Preferably, the voltage VSS is ground potential. The ASIC 2000 further receives an ON_OFF signal from a switch S1 that is in turn coupled to the voltage VSS. The ASIC 2000 includes a debouncer 2014 that debounces the signal developed by the switch S1.

The ASIC 2000 includes an oscillator 2016 that serves as an internal clock for the ASIC 2000, a power-on reset circuit 2018 that resets various parameters upon energization of the ASIC 2000 and an under voltage detector 2020 that disables the ASIC 2000 when the battery voltage drops below a particular level. A resistor R is coupled to the voltage VSS and a capacitor (not shown) that is internal to the ASIC 2000 and establishes the frequency of the oscillator 2016.

Still further in the preferred embodiment, the ASIC 2000 includes a pair of timers 2022 and 2024, a system controller 2026 that executes programming to control LED1 138a and LED2 138b in conjunction with eight-bit address register 2027, a six-bit address pointer register 2028, and a shutdown timer 2030. As noted in greater detail hereinafter, the value developed by the address pointer register 2028 at any particular time is equal to the value developed by the address register 2027 at that time with the second and third least significant bits removed from the eight-bit value developed by the register 2027 and the remaining more significant bits shifted toward the least significant bit. For example, if the value developed by the address register 2027 at a particular time is 01101100, then the output value of the address pointer register 2028 at that time is 011010. Similarly, if the current output value of the address register 2027 is 10101001, 00001110, or 10011111, then the current output value of the address pointer register is 101011, 000010, or 100111, respectively.

Figure 64:
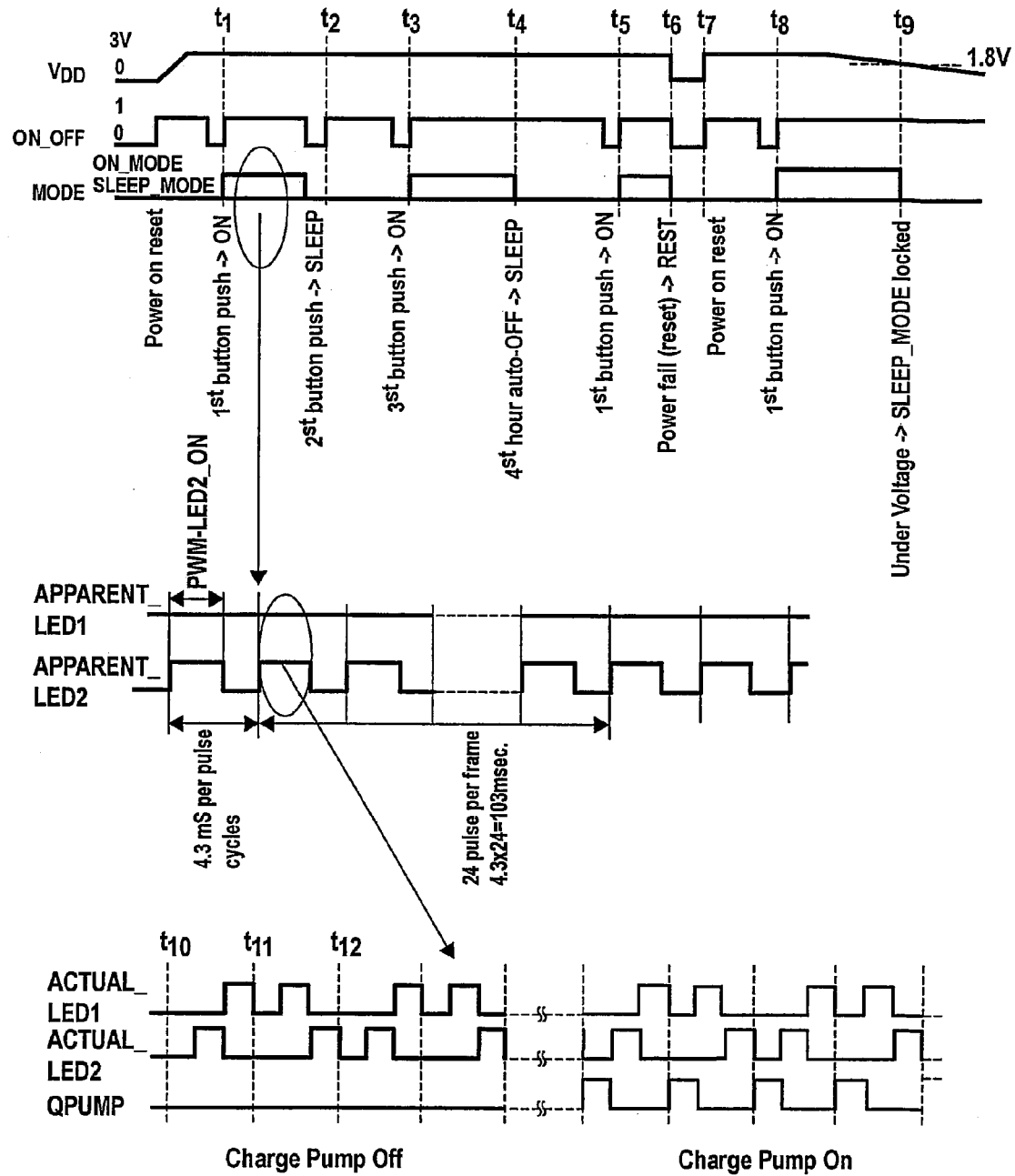
FIG. 64 is a series of waveform diagrams illustrating operation of the ASIC of FIG. 63.

Referring next to FIG. 64, a series of waveform diagrams illustrate operation of the circuitry of FIG. 63. The waveform diagram labeled MODE reflects the operation of the ASIC 2000 in response to various conditions including the state of the switch S1 and the voltage VDD developed by the batteries 112a, 112b. When the switch S1 is open, as seen in FIG. 63, the voltage VDD is supplied to the debouncer 2014. When the switch S1 of FIG. 63 is closed, a low state signal in the form of the voltage VSS is supplied to the debouncer 2014, as reflected in the transition between one and zero states in the ON_OFF signal illustrated in FIG. 64. Upon release of the switch S1 a transition occurs from the zero to one states of the ON_OFF signal, and the ASIC 2000 enters an on mode at a time $t_1$. During operation in the on mode, the LED1 138*a* and the LED2 138*b* are lit, as note din greater detail hereinafter. When the switch S1 is momentarily closed then opened at a time $t_2$, the ASIC 2000 enters a sleep mode of operation, during which only the debouncer 2014 is active so as to retain the capability of detecting momentary closure of the switch S1 for at least a particular period of time, such as 8 milliseconds. Thereafter, closure and opening of the switch S1 at a time $t_3$ for at least the particular period of time causes the ASIC 2000 to reenter the on mode.

Following the time $t_3$, if the switch S1 is not actuated within a predetermined delay period, such as four hours, the ASIC 2000 automatically enters the sleep mode, as represented at time $t_4$. A subsequent momentary closure and opening of the switch S1 at a time $t_5$ causes the ASIC 2000 to again enter the on mode.

At a time $t_6$ the power provided to the ASIC 2000 is interrupted, such as by removal of one or more of the batteries 112. Upon reapplication of power to the ASIC 2000 at a time $t_7$, a power-on reset mode is entered wherein values used by the ASIC 2000 are initialized. Thereafter, the ASIC 2000 enters the sleep mode until the switch S1 is again momentarily closed and opened at time $t_8$. Following the time $t_8$, the ASIC 2000 remains in the on mode until the four-hour auto shut-off delay period has expired, or until the switch S1 is momentarily closed, or until the voltage developed by the batteries 112 drops below a particular level, such as 1.8 volts, as illustrated at time $t_9$.

As seen in the waveform diagrams illustrated as APPARENT_LED1 and APPARENT_LED2, the LED1 138*a* is operated such that it appears to be continuously on whereas the LED2 138*b* is operated such that it appears to flicker with a pseudo random flicker pattern. With regard to LED2 138*b*, a number of frames of equal duration are established wherein each frame includes a number of pulse cycles therein. Preferably, although not necessarily, each pulse cycle is 4.3 milliseconds in length and 24 pulses are included per frame. Accordingly, each frame is 103 milliseconds in duration. Also preferably, the pulse on-times for a particular frame are all equal in duration, resulting in a particular average current magnitude for that frame. Also preferably, although not necessarily, the pulse widths in adjacent frames are different so as to provide an average current different from the particular average current magnitude to provide the flickering effect. The choice of the pulse widths for the frames is controlled by the pseudo random generator 2002 and entries in the PWM value table 2004.

As illustrated in the bottom three waveforms of FIG. 64, the waveforms ACTUAL_LED1 and ACTUAL_LED2 indicate the drive waveforms applied to LED1 138*a* and LED2 138*b*, respectively. (The scale of the waveforms ACTUAL_LED1 and ACTUAL_LED2 is greatly expanded relative to the scale of the waveforms APPARENT_LED1 and APPARENT_LED2.) In general, the LED1 138*a* and LED2 138*b* are operated intermittently at a high frequency so as to provide the appearance that the LED's are being operated at a constant intensity level at any particular instant of time. More particularly, between a time $t_{10}$ and a time $t_{12}$, the LED1 138*a* receives two pulses of current, as does the LED2 138*b*. Specifically, in a first one-sixth of a total of two cycles between the times $t_{10}$ and $t_{12}$, neither LED1 138*a* nor LED2 138*b* receives a current pulse. In a second one-sixth of the two cycles the LED2 138*b* receives a pulse of current whereas the LED1 138*a* does not. In a third one-sixth of the two cycles the LED1 138*a* receives a current pulse whereas the LED2 138*b* does not. In a fourth one-sixth of the two cycles (wherein the second cycle begins at a time $t_{11}$) neither the LED1 138*a* nor the LED2 138*b* receives a current pulse while in a fifth one-sixth of the two cycles LED1 138*a* receives a current pulse whereas the LED2 138*b* does not. Finally, in a sixth one-sixth of the two cycles the LED2 138*b* receives a current pulse whereas the LED1 138*a* does not.

Thereafter, the above-described cycle pairs repeat until the combined voltage developed by the batteries 112 drops below the voltage required to adequately energize the LED1 138*a* and LED2 138*b*. At this point, the charge pump 2008 is actuated to provide sufficient forward voltage to the LED1 138*a* and the LED2 138*b*. Specifically, the LED1 138*a* and the LED2 138*b* receive the current pulses as described previously and the charge pump 2008 is turned on during the first one-sixth and fourth one-sixth of cycle pair to charge the capacitor $C_1$ of FIG. 63. The capacitor $C_1$ thereafter provides sufficient voltage to the LED1 138*a* and the LED2 138*b* to maintain adequate drive thereto. Preferably, although not necessarily, the drive pulses for LED1 138*a* and LED2 138*b* have a 45 milliamp peak current and a typical pulse width of about 4.2 microseconds. If desired, these values may be changed to obtain different LED intensities.

Figure 65A:
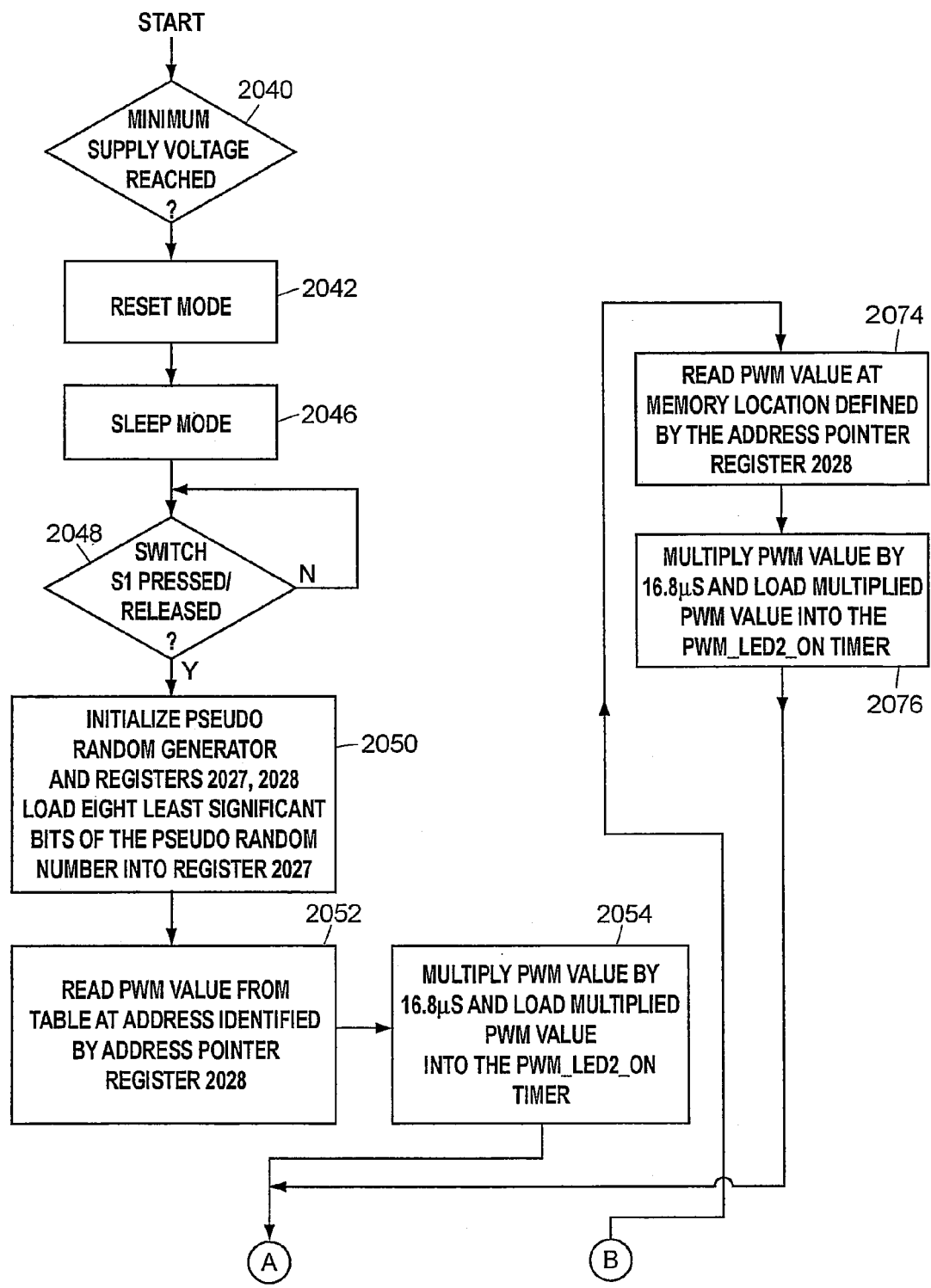
FIGS. 65A and 65B, when joined along the similarly lettered lines, together comprise a flowchart of programming executed by the ASIC 2000 to control the LED1 and the LED2.
Figure 65B:
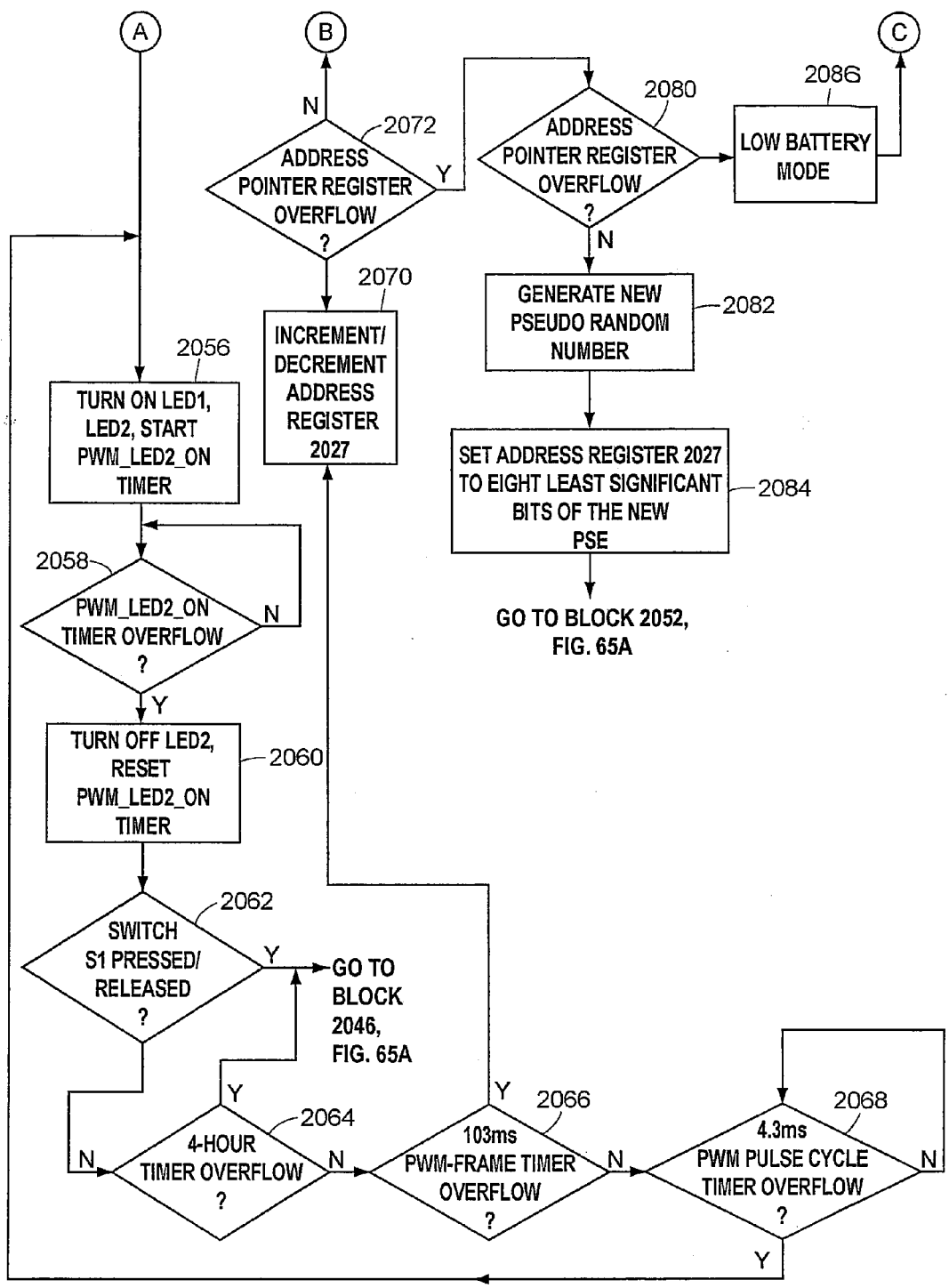

Referring next to the flowchart of FIGS. 65A and 65B, which illustrate the overall operation of the ASIC 2000 in accordance with the waveforms of FIG. 64 (with the exception of the bottom three waveforms thereof), control begins at a block 2040, which checks to determine when a POWER-ON RESET signal has been developed. This signal is generated when batteries are first placed into the active material emitting device, or when dead batteries are replaced with charged batteries, or when charged batteries are removed from the device and are returned to the device and a minimum supply voltage has been reached.

Control then passes to a block 2042, which implements a reset mode of operation whereby all internal registers are set to define start-up values and all timers are reset. A block 2046 then implements a sleep mode of operation. During operation in the sleep mode, all internal components of the ASIC 2000 are deactuated, with the exception of the debouncer 2014, which remains active to determine when the switch S1 is momentarily depressed for greater than the particular period of time.

Following the block 2046, control pauses at a block 2048 until a determination has been made that the switch S1 has been momentarily depressed and released. When this action is detected, a block 2050 initializes the pseudo random generator 2002 of FIG. 63 and causes the pseudo random generator 2002 to develop a sixteen-bit pseudo random number at the output of the shift register SR of FIG. 66, of which the eight least significant bits are loaded into the address register 2027 of FIG. 63. This loading, in turn, causes the address pointer register 2028 to develop a six-bit number corresponding to the eight-bit pseudo random number loaded into the register 2027 as described above.

Following the block 2050, a block 2052 reads one of 64 PWM values stored in the PWM value table 2004 of FIG. 63. In general, the PWM values stored in the table 2004 define duty cycles for the LED2 138*b*. Preferably, PWM values that are stored in adjacent locations in the table 2004 have no particular relationship with one another (i.e., the PWM values in adjacent storage locations vary in a random or pseudo random manner from one another), although this need not be the case. In any event, the block 2052 reads the PWM value from the table 2004 stored at the address identified by the six-bit current output value of the address pointer register 2028. A block 2054 then multiplies the PWM value read by the block 2052 by a particular length of time, such as 16.8 microseconds, and loads the multiplied PWM value read by the block 2052 into the PWM-LED2_ON timer 2006.

Following the block 2054, a block 2056, FIG. 65B, turns on the LED1 138a and the LED2 138b and starts the PWM-LED2_ON timer 2006. Assuming at this point that the batteries 112 are fully charged, the charge pump portion of the circuit 2008 is inactive. Control then pauses at a block 2058 until the PWM-LED2_ON timer 2006 experiences an overflow condition. When this overflow condition occurs, a block 2060 turns off the LED2 138b for the balance of the 4.3 milliseconds pulse cycle and resets the PWM-LED_ON timer 2006. Control then passes through a block 2062 which determines whether the switch S1 has been momentarily pressed and released. If not, a block 2064 determines whether the four-hour timer has experienced an overflow condition. If this is also not the case, a block 2066 checks to determine whether the 103 millisecond PWM-frame timer has experienced an overflow condition. If this is further not the case, control remains with a block 2068 until the 4.3 millisecond PWM pulse cycle timer experiences an overflow condition, whereupon control returns to the block 2056 to begin the next 4.3 millisecond PWM pulse cycle.

If the block 2062 determines that the switch S1 has been momentarily pressed and released, or if the block 2064 determines that the four-hour timer has experienced an overflow condition, control returns to the block 2046 of FIG. 65A whereupon the sleep mode is entered.

If the block 2066 determines that the 103 millisecond PWM-frame timer has overflowed, control passes through a block 2070 which either increments or decrements the address register 2027. The decision to increment or decrement the address pointer is determined by the most significant bit of the sixteen-bit pseudo random number developed by the pseudo random generator 2002. A zero as the most significant bit causes the block 2070 to decrement the address register 2027, whereas a one as the most significant bit causes the block 2070 to increment the address register 2027. If desired, the decision to increment or decrement may be based upon another bit of the pseudo random number, or a zero in a particular bit position may cause the block 2070 to increment the address register 2027 while a one in the particular bit position may cause the block 2070 to decrement the address register 2027. As a still further alternative, the block may only decrement or only increment the address register 2027 for each pseudo random number developed by the generator 2002 regardless of the values of the bits of the pseudo random number. Still further, the particular bit that determines whether to increment or decrement preferably may vary from number-to-number developed by the generator 2002. In any event, the address pointer may be incremented when a particular pseudo random number has been developed by the generator 2002 and the address pointer may be decremented (or incremented, for that matter) when a subsequent pseudo random number is developed by the generator 2002.

Following the block 2070, a block 2072 checks to determine whether the address pointer register 2028 has experienced an overflow condition. Specifically, because 64 values are stored in the table 2004, the block 2072 checks to determine whether the incrementing or decrementing of the address pointer 2070 has caused the address pointer register 2028 to decrement to a value of 000000 or to increment to a value of 111111. If this is not the case, a block 2074 reads the PWM value at the next memory location (either above or below the previous memory location) defined by the current value of the address pointer register 2028. A block 2076 multiplies the PWM value stored at the memory location with the particular length of time (i.e., 16.8 microseconds) and loads the multiplied value into the PWM-LED2_ON timer 2006 and control passes to the block 2056 of FIG. 65B to start a new 4.3 millisecond pulse cycle.

If the block 2072 determines that the address pointer register 2028 has experienced an overflow condition, a block 2080 checks to determine whether an under voltage condition has been detected whereby the battery voltage has fallen below a particular level of, for example, 1.8 volts. If this is found to be the case, control passes to a block 2086 that causes the ASIC 2000 to enter a low battery mode of operation. The block 2086 maintains the ASIC 2000 in the low battery mode until a power-on reset condition again occurs, for example, by replacing the discharged batteries with fully charged batteries. This action prevents the discharged batteries from being further discharged to a point where they may leak and damage the device.

If the block 2080 determines that the under voltage condition has not been detected, a block 2082 causes the pseudo random generator 2002 of FIG. 63 to generate a new sixteen-bit psuedo random number and the address register 2027 is loaded with the eight least significant bits of this new number by a block 2084. Control then passes to the block 2052 FIG. 65A.

The foregoing methodology of ignoring two of the eight bits of the pseudo random number when addressing the table 2004 results in a pattern of repetitively addressing two consecutive memory locations in the table 2004 a total of four times. That is, in the example where the pseudo random number is 00000000 and the block 2070 is to increment, the memory location addressing scheme will proceed as follows:

| | | |
|---|---|---|
| 000000 | 000010 | 000100 |
| 000001 | 000011 | 000101 |
| 000000 | 000010 | 000100 |
| 000001 | 000011 | 000101 |
| 000000 | 000010 | 000110 |
| 000001 | 000011 | 000111 |
| 000000 | 000100 | . |
| 000001 | 000101 | . |
| 000010 | 000100 | . |
| 000011 | 000101 | |

The foregoing addressing scheme results in a flickering effect that is visually pleasing while allowing the use of a relatively small table 2004. This, in turn, reduces the cost of the ASIC 2000.

Although some of the embodiments as disclosed herein include a light emitter and an active material emitter, this should not be limiting. In fact, a device as disclosed herein may include one or both of a light emitter and active material emitter. An active material emission accelerator, such as a heater or a fan, may be incorporated into the embodiment of FIGS. 59-62 or any of the embodiments as disclosed herein.

In any of the embodiments disclosed herein that utilize a switch actuated by insertion of a cartridge into an active material emitting device, or where insertion of a cartridge completes a circuit or otherwise alters an electrical characteristic of a component, such action may cause a visual and/or audible indication to be generated. Alternatively or in addition, such action may enable or alter operation of the device itself or one or more features of the device. In general, it is contemplated any effect may be caused by insertion of a cartridge into an active material emitting device.

Additionally, in the embodiments utilizing mechanical and electrical switches and circuit-forming elements, if the switch has not been depressed or contacted and/or a circuit has not been formed, the device preferably will not function properly. Specifically, if the device includes a heater, a fan, a light, or any other component, such components may not function if a cartridge has not be inserted into the device.

Optionally, an active material emission accelerator, such as a heater or a fan, may be incorporated into the embodiment of FIGS. 59-62 or any of the embodiments as disclosed herein.

Although active material emitting devices are depicted for most of the embodiments as disclosed herein, these devices are illustrative of the operation necessary and non-limiting with respect to the type of devices that may be utilized with the cartridges as described herein.

Any of the active material cartridges as disclosed herein may be removed from an active material emitting device and a new cartridge may be inserted into the device. Optionally, all of the cartridges herein may be removed and reinserted, as needed, to check the use-up of the active material or any other feature of the respective cartridge.

Optionally, any of the features of any of the embodiments as discussed herein may be combined to form even further embodiments.

Preferably, the active materials as described herein are in a gel-like or liquid form. Optionally, the active materials may also take the form of a semi-solid, a solid, or combinations thereof.

INDUSTRIAL APPLICABILITY

The present invention comprises a device for light and/or active material emission. The device provides an overall desired aesthetic ambience in an area, such as a room by simulating a real candle. The candle simulation includes creating a flameless flickering light which simulates a real candle flame.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. An active material cartridge, comprising:
    a frame; and
    an active material refill comprising first and second reservoirs having active materials therein and joined to one another by a flexible connecting portion, wherein the refill is attached to the frame by flexing the refill about the connecting portion;
    wherein the first frame includes first and second frame portions having first and second sets of tabs extending inwardly from first and second flanges, respectively, such that lip portions of the reservoirs are retained between the respective ledge and the respective tabs.

2. The active material cartridge of claim 1, wherein the refill further includes first and second lip portions surrounding the first and second reservoirs, respectively, and wherein the connecting portion joins the first and second lip portions to form the refill.

3. The active material cartridge of claim 2, wherein the first and second reservoirs include first and second non-removable vapor permeable sealing layers, respectively, disposed in first and second top surfaces, respectively, thereof and further include first and second removable vapor impermeable layers disposed above the non-removable vapor permeable sealing layers, respectively, and wherein one or more of the vapor impermeable layers may be removed to transmit active material from the respective reservoir.

4. The active material cartridge of claim 1, wherein the first and second frame portions include first and second ledges respectively extending inwardly therefrom, thereby forming first and second apertures, respectively, and wherein the first and second reservoirs are aligned with the first and second apertures, respectively, when the cartridge is assembled.

5. The active material cartridge of claim 4, wherein the first frame portion includes a first plurality of posts extending from a back surface of the first ledge, respectively, and the second frame portion includes a second plurality of posts extending from a back surface of the second ledge, respectively, and wherein the first plurality and the second plurality of posts are joined to one another to form the frame.

6. The active material cartridge of claim 5, wherein the frame includes a protrusion extending from a first end of the frame.

7. The active material cartridge of claim 6, wherein the connecting portion includes an aperture therein such that the connecting portion extends over the first end of the frame and wherein the protrusion extends through the aperture.

8. The active material cartridge of claim 6, wherein the protrusion includes a U-shaped opening wherein the opening is adapted to snappingly engaged a post disposed within an active material emitting device and the protrusion is adapted to actuate a switch in the active material device when the active material cartridge is inserted therein.

9. An active material cartridge, comprising:
    a frame; and
    an active material refill comprising first and second reservoirs having active materials therein and joined to one another by a flexible connecting portion, wherein the refill is attached to the frame by flexing the refill about the connecting portion;
    wherein the frame includes first and second frame portions having first and second ledges respectively extending inwardly therefrom, thereby forming first and second apertures, respectively, and wherein the first and second reservoirs are aligned with the first and second apertures, respectively, when the cartridge is assembled; and
    wherein the first frame portion includes a first plurality of posts extending from a back surface of the first ledge, respectively, and the second frame portion includes a second plurality of posts extending from a back surface of the second ledge, respectively, and wherein the first plurality and the second plurality of posts are joined to one another to form the frame.

10. An active material cartridge, comprising:
    a frame; and
    an active material refill comprising first and second reservoirs having active materials therein and joined to one another by a flexible connecting portion, wherein the refill is attached to the frame by flexing the refill about the connecting portion;
    wherein the frame includes a protrusion extending from a first end of the frame; and wherein the connecting portion includes an aperture therein such that the connecting portion extends over the first end of the frame and wherein the protrusion extends through the aperture.

11. The active material cartridge of claim 10, wherein the protrusion includes an opening that is adapted to engage snappingly a post disposed within an active material emitting device and the protrusion is adapted to actuate a switch in the active material emitting device when the active material cartridge is inserted therein.

12. The active material cartridge of claim 10, wherein the frame includes an aperture in a side thereof and wherein the refill is disposed within the aperture.

13. The active material cartridge of claim 12, wherein the frame further includes at least one tab for securing the refill to the frame.

14. The active material cartridge of claim 13, wherein the reservoir further includes a lip portion surrounding the reservoir and wherein the at least one tab secures the refill by the lip portion thereof to retain the refill within the frame.

15. The active material cartridge of claim 1, wherein the reservoir includes a non-removable vapor permeable sealing layer disposed in a top surface thereof and further includes a removable vapor impermeable layer disposed above the non-removable vapor permeable sealing layer, such that the vapor impermeable layer may be removed to transmit active material from the reservoir.

* * * * *

UNITED STATES PATENT AND TRADEMARK OFFICE
CERTIFICATE OF CORRECTION

| | | |
|---|---|---|
| PATENT NO. | : 7,350,720 B2 | Page 1 of 1 |
| APPLICATION NO. | : 11/140329 | |
| DATED | : April 1, 2008 | |
| INVENTOR(S) | : Thomas Jaworski et al. | |

It is certified that error appears in the above-identified patent and that said Letters Patent is hereby corrected as shown below:

Column 44, Line 7: replace "claim 1" with --claim 10--

Signed and Sealed this

Fourth Day of November, 2008

JON W. DUDAS
*Director of the United States Patent and Trademark Office*